US011583525B2

(12) United States Patent
Sebti et al.

(10) Patent No.: US 11,583,525 B2
(45) Date of Patent: Feb. 21, 2023

(54) GERANYLGERANYLTRANSFERASE I INHIBITOR FOR TREATMENT OF A PTEN DEFECTIVE CANCER

(71) Applicants: H. LEE MOFFITT CANCER CENTER AND RESEARCH INSTITUTE, INC., Tampa, FL (US); NEW YORK UNIVERSITY, New York, NY (US)

(72) Inventors: Said M. Sebti, Tampa, FL (US); Michele Pagano, New York, NY (US); Shafi Kuchay, New York, NY (US)

(73) Assignees: H. LEE MOFFITT CANCER CENTER AND RESEARCH INSTITUTE, INC., Tampa, FL (US); NEW YORK UNIVERSITY, New York, NY (US)

( * ) Notice: Subject to any disclaimer, the term of this patent is extended or adjusted under 35 U.S.C. 154(b) by 153 days.

(21) Appl. No.: 16/619,994

(22) PCT Filed: Jun. 6, 2018

(86) PCT No.: PCT/US2018/036206
§ 371 (c)(1),
(2) Date: Dec. 6, 2019

(87) PCT Pub. No.: WO2018/226791
PCT Pub. Date: Dec. 13, 2018

(65) Prior Publication Data
US 2021/0093632 A1 Apr. 1, 2021

Related U.S. Application Data

(60) Provisional application No. 62/671,717, filed on May 15, 2018, provisional application No. 62/519,001, filed on Jun. 13, 2017, provisional application No. 62/515,990, filed on Jun. 6, 2017.

(51) Int. Cl.
*A61K 31/496* (2006.01)
*A61K 31/4985* (2006.01)
*G01N 33/574* (2006.01)

(52) U.S. Cl.
CPC ........ *A61K 31/496* (2013.01); *A61K 31/4985* (2013.01); *G01N 33/57484* (2013.01)

(58) Field of Classification Search
CPC ............................ A61K 31/496; C07D 403/06
USPC ...................... 514/254.04; 544/316
See application file for complete search history.

(56) References Cited

U.S. PATENT DOCUMENTS

| 6,960,648 | B2 | 11/2005 | Bonny |
| 8,828,451 | B2 | 9/2014 | Sebti et al. |
| 9,498,492 | B2 | 11/2016 | Cheng et al. |
| 9,511,084 | B2 | 12/2016 | Cheng et al. |
| 2002/0035243 | A1 | 3/2002 | Imfeld et al. |
| 2002/0120100 | A1 | 8/2002 | Bonny |
| 2003/0032594 | A1 | 2/2003 | Bonny |
| 2008/0131526 | A1 | 6/2008 | Sebti et al. |
| 2011/0059994 | A1 | 3/2011 | Lee et al. |
| 2012/0035184 | A1 | 2/2012 | Sebti et al. |
| 2013/0281493 | A1 | 10/2013 | Freed-Pastor et al. |

FOREIGN PATENT DOCUMENTS

WO 2017007634 A1 1/2017

OTHER PUBLICATIONS

Chen, BB et al. Skp-cullin-F box E3 ligase component FBXL2 ubiquitinates Aurora B to inhibit tumorigenedid. Aug. 8, 2013.
International Search Report and Written Opinion in PCT/US2018/036206, dated Aug. 3, 2018. 9 pages.
Alzayady, K. J. et al. Functional inositol 1,4,5-trisphosphate receptors assembled from concatenated homo- and heteromeric subunits. J. Biol. Chem. 288, 29772-29784 (2013).
Alzayady, K. J., Panning, M. M., Kelley, G. G. & Wojcikiewicz, R. J. Involvement of the p97-Ufd1-Npl4 complex in the regulated endoplasmic reticulum-associated degradation of inositol 1,4,5-trisphosphate receptors. J. Biol. Chem. 280, 34530-34537 (2005).
Barber, A. G. et al. Characterization of desmoglein expression in the normal prostatic gland. Desmoglein 2 is an independent prognostic factor for aggressive prostate cancer. PLoS One 9, e98786 (2014).
Berndt, Norbert, and Saïd M. Sebti. Measurement of protein farnesylation and geranylgeranylation in vitro, in cultured cells and in biopsies, and the effects of prenyl transferase inhibitors, nature protocols 6.11 (2011): 1775.
Berndt, Norbert, Andrew D. Hamilton, and Saïd M. Sebti. "Targeting protein prenylation for cancer therapy." Nature Reviews Cancer 11.11 (2011): 775-791.
Bittremieux, M., Parys, J. B., Pinton, P. & Bultynck, G. ER functions of oncogenes and tumor suppressors: Modulators of intracellular Ca(2+) signaling. Biochim. Biophys. Acta 1863 (6 Pt B), 1364-1378 (2016).
Bokkala, S. & Joseph, S. K. Angiotensin II-induced down-regulation of inositol trisphosphate receptors in WB rat liver epithelial cells. Evidence for involvement of the proteasome pathway. J. Biol. Chem. 272, 12454-12461 (1997).
Bononi, A. et al. Identifi of PTEN at the ER and MAMs and its regulation of Ca(2+) signaling and apoptosis in a protein phosphatase-dependent manner. Cell Death Diff. 20, 1631-1643 (2013).
Brown, S. B., Brown, E. A. & Walker, I. The present and future role of photodynamic therapy in cancer treatment. Lancet Oncol. 5, 497-508 (2004).
Castillo-Martin, M., Thin, T. H., Collazo Lorduy, A. & Cordon-Cardo, C. Immunopathologic assessment of PTEN expression. Methods Mol. Biol. 1388, 23-37 (2016).

(Continued)

Primary Examiner — Jeffrey H Murray
(74) Attorney, Agent, or Firm — Meunier Carlin & Curfman LLC

(57) ABSTRACT

A method is disclosed for treating a cancer in a subject that involves administering to the subject a therapeutically affective amount of a geranylgeranyltransferase I (GGTase I) inhibitor, such as GGTI-2418, wherein the cancer comprises a defective PTEN, a hyperactivated FBXL2, or a low level of IP3R3. In some embodiments, the method further involves administering to the subject a therapeutically affective amount of an Akt inhibitor.

13 Claims, 73 Drawing Sheets

(56) References Cited

OTHER PUBLICATIONS

Chen, R. et al. Bcl-2 functionally interacts with inositol 1,4,5-trisphosphate receptors to regulate calcium release from the ER in response to inositol 1,4,5-trisphosphate. J. Cell Biol. 166, 193-203 (2004).

Clapham, D. E. Calcium signaling. Cell 131, 1047-1058 (2007).

D'Angiolella, V. et al. Cyclin F-mediated degradation of ribonucleotide reductase M2 controls genome integrity and DNA repair. Cell 149, 1023-1034 (2012).

Dankert, J. F. et al. Cyclin F-mediated degradation of SLBP limits H2A.X accumulation and apoptosis upon genotoxic stress in G2. Mol. Cell 64, 507-519 (2016).

Deshaies, R. J. Proteotoxic crisis, the ubiquitin-proteasome system, and cancer therapy. BMC Biol. 12, 94 (2014).

Duan, S. et al. FBXO11 targets BCL6 for degradation and is inactivated in diff large B-cell lymphomas. Nature 481, 90-93 (2012).

Duan, S. et al. mTOR generates an auto-amplifi loop by triggering the βTrCP- and CK1α-dependent degradation of DEPTOR. Mol. Cell 44, 317-324 (2011).

Falsetti SC, et al. Geranylgeranyltransferase I Inhibitors Target Ra1B to Inhibit Anchorage-Dependent Growth and Induce Apoptosis and Ra1A to Inhibit Anchorage-Independent Growth. Mol Cell Biol 2007 27:8003-8014.

Fan, G. et al. Gating machinery of InsP3R channels revealed by electron cryomicroscopy. Nature 527, 336-341 (2015).

Giorgi, C. et al. Intravital imaging reveals p53-dependent cancer cell death induced by phototherapy via calcium signaling. Oncotarget 6, 1435-1445 (2015).

Giorgi, C. et al. PML regulates apoptosis at endoplasmic reticulum by modulating calcium release. Science 330, 1247-1251 (2010).

Giorgi, C., Bonora, M. & Pinton, P. Inside the tumor: p53 modulates calcium homeostasis. Cell Cycle 14, 933-934 (2015).

Grynkiewicz, G., Poenie, M. & Tsien, R. Y. A new generation of Ca2+ indicators with greatly improved fluorescence properties. J. Biol. Chem. 260, 3440-3450 (1985).

Hollander, M. C., Blumenthal, G. M. & Dennis, P. A. PTEN loss in the continuum of common cancers, rare syndromes and mouse models. Nat. Rev. Cancer 11, 289-301 (2011).

Joseph, S. K., Lin, C., Pierson, S., Thomas, A. P. & Maranto, A. R. Heteroligomers of type-I and type-III inositol trisphosphate receptors in WB rat liver epithelial cells. J. Biol. Chem. 270, 23310-23316 (1995).

Kazi, A. et al. Blockade of protein geranylgeranylation inhibits Cdk2-dependent p27Kip1 phosphorylation on Thr187 and accumulates p27Kip1 in the nucleus: implications for breast cancer therapy. Mol. Cell. Biol. 29, 2254-2263 (2009).

Khan, M. T., Wagner, L., II, Yule, D. I., Bhanumathy, C. & Joseph, S. K. Akt kinase phosphorylation of inositol 1,4,5-trisphosphate receptors. J. Biol. Chem. 281, 3731-3737 (2006).

Kuchay, S. et al. FBXT2- and PTPL1-mediated degradation of p110-free p85β regulatory subunit controls the PI(3)K signalling cascade. Nat. Cell Biol. 15, 472-480 (2013).

Lin, C. C., Baek, K. & Lu, Z. Apo and InsP3-bound crystal structures of the ligand-binding domain of an InsP3 receptor. Nat. Struct. Mol. Biol. 18, 1172-1174 (2011).

Marchi, S. et al. Akt kinase reducing endoplasmic reticulum Ca2+ release protects cells from Ca2+-dependent apoptotic stimuli. Biochem. Biophys. Res. Commun. 375, 501-505 (2008).

Marchi, S. et al. Selective modulation of subtype III IP3R by Akt regulates ER Ca2+ release and apoptosis. Cell Death Dis. 3, e304 (2012).

Mikoshiba, K. IP3 receptor/Ca2+ channel: from discovery to new signaling concepts. J. Neurochem. 102, 1426-1446 (2007).

Oakes, S. A. et al. Proapoptotic BAX and BAK regulate the type 1 inositol trisphosphate receptor and calcium leak from the endoplasmic reticulum. Proc. Natl Acad. Sci. USA 102, 105-110 (2005).

Oberdorf, J., Webster, J. M., Zhu, C. C., Luo, S. G. & Wojcikiewicz, R. J. Down-regulation of types I, II and III inositol 1,4,5-trisphosphate receptors is mediated by the ubiquitin/proteasome pathway. Biochem. J. 339, 453-461 (1999).

Orrenius, S., Zhivotovsky, B. & Nicotera, P. Regulation of cell death: the calcium-apoptosis link. Nat. Rev. Mol. Cell Biol. 4, 552-565 (2003).

Puc, J. et al. Lack of PTEN sequesters CHK1 and initiates genetic instability. Cancer Cell 7, 193-204 (2005).

Ran, F. A. et al. Genome engineering using the CRISPR-Cas9 system. Nat. Protocols 8, 2281-2308 (2013).

Sebti, Saïd M., and Andrew D. Hamilton. "Farnesyltransferase and geranylgeranyltransferase I inhibitors and cancer therapy: lessons from mechanism and bench-to-bedside translational studies." Oncogene 19.56 (2000): 6584-6593.

Seo, M. D. et al. Structural and functional conservation of key domains in InsP3 and ryanodine receptors. Nature 483, 108-112 (2012).

Skaar, J. R., Pagan, J. K. & Pagano, M. Mechanisms and function of substrate recruitment by F-box proteins. Nat. Rev. Mol. Cell Biol. 14, 369-381 (2013).

Sung, P. J. et al. Phosphorylated K-Ras limits cell survival by blocking Bcl-xL sensitization of inositol trisphosphate receptors. Proc. Natl Acad. Sci. USA 110, 20593-20598 (2013).

Tan, M. K., Lim, H. J., Bennett, E. J., Shi, Y. & Harper, J. W. Parallel SCF adaptor capture proteomics reveals a role for SCFFBXL17 in NRF2 activation via BACH1 repressor turnover. Mol. Cell 52, 9-24 (2013).

Wang, C. et al. Identifi of FBL2 as a geranylgeranylated cellular protein required for hepatitis C virus RNA replication. Mol. Cell 18, 425-434 (2005).

Wieckowski, M. R., Giorgi, C., Lebiedzinska, M., Duszynski, J. & Pinton, P. Isolation of mitochondria-associated membranes and mitochondria from animal tissues and cells. Nat. Protocols 4, 1582-1590 (2009).

Wojcikiewicz, R. J. & He, Y. Type I, II and III inositol 1,4,5-trisphosphate receptor co-immunoprecipitation as evidence for the existence of heterotetrameric receptor complexes. Biochem. Biophys. Res. Commun. 213, 334-341 (1995).

Wright, F. A. & Wojcikiewicz, R. J. Chapter 4—inositol 1,4,5-trisphosphate receptor ubiquitination. Prog. Mol. Biol. Transl. Sci. 141, 141-159 (2016).

Yoshida, Y. et al. A comprehensive method for detecting ubiquitinated substrates using TR-TUBE. Proc. Natl Acad. Sci. USA 112, 4630-4635 (2015).

Zhang, Fang L., and Patrick J. Casey. "Protein prenylation: molecular mechanisms and functional consequences." Annual review of biochemistry 65.1 (1996): 241-269.

International Preliminary Report on Patentability issued for Application No. PCT/US2018/036206, dated Dec. 19, 2019.

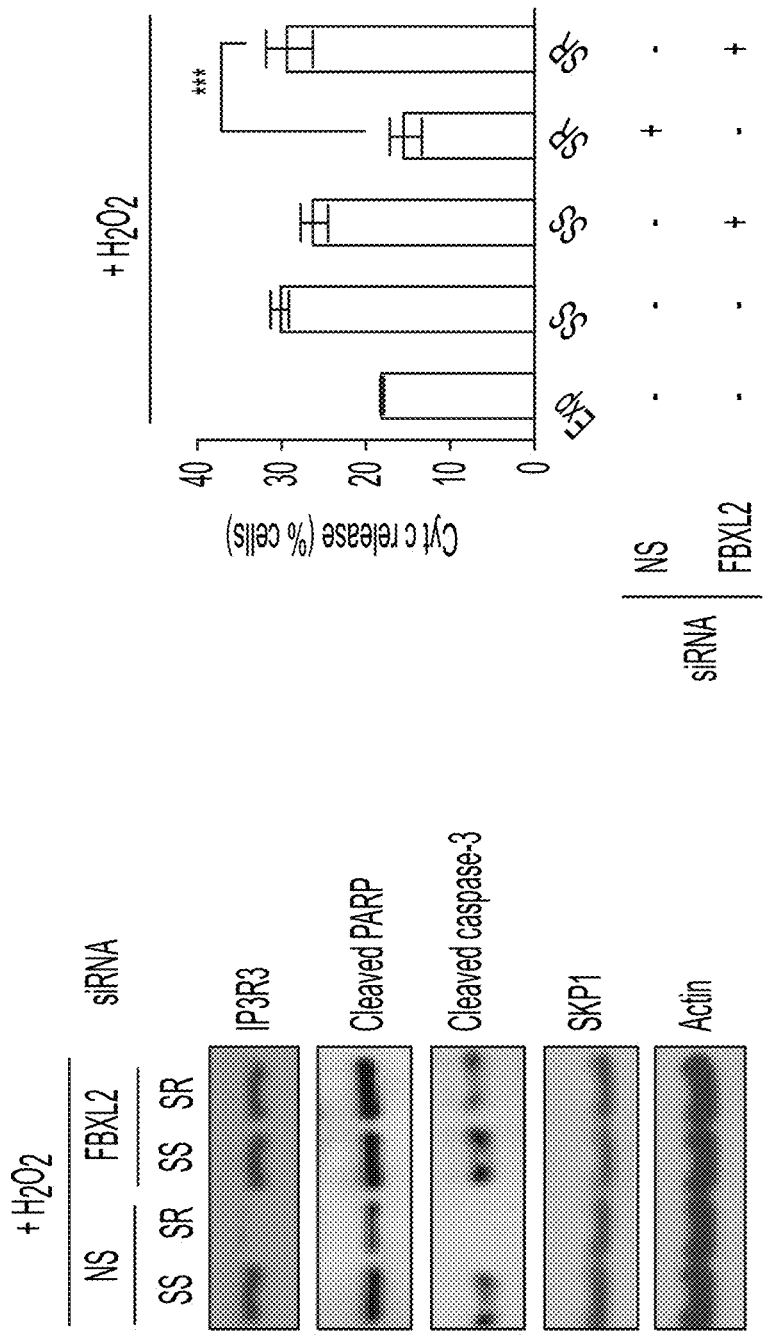

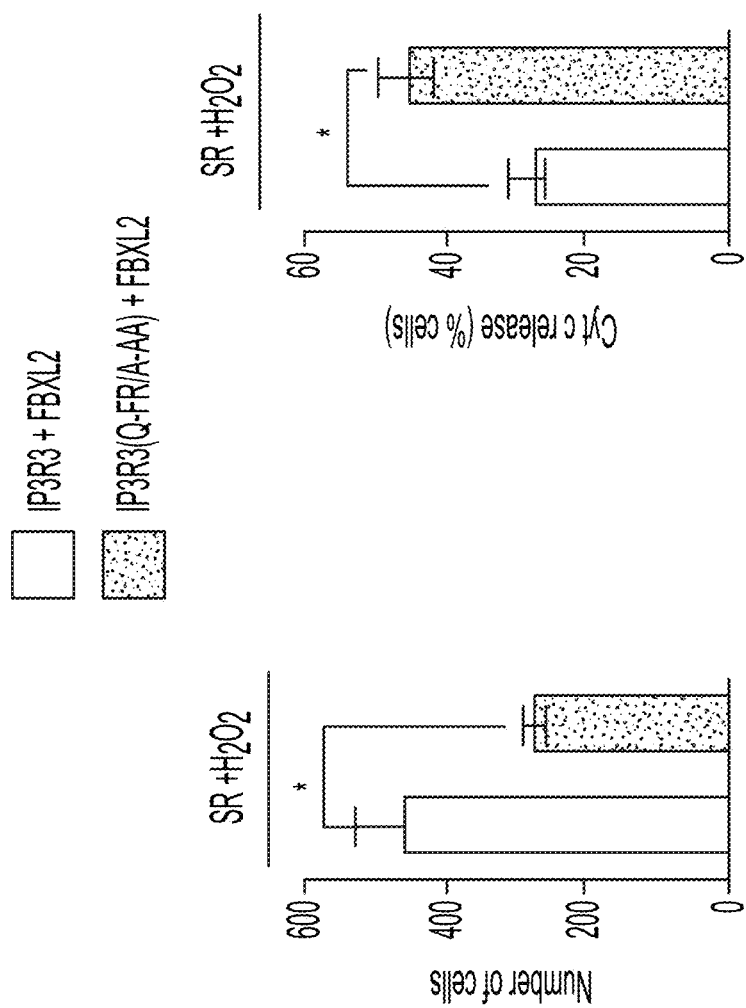

FIG. 2B

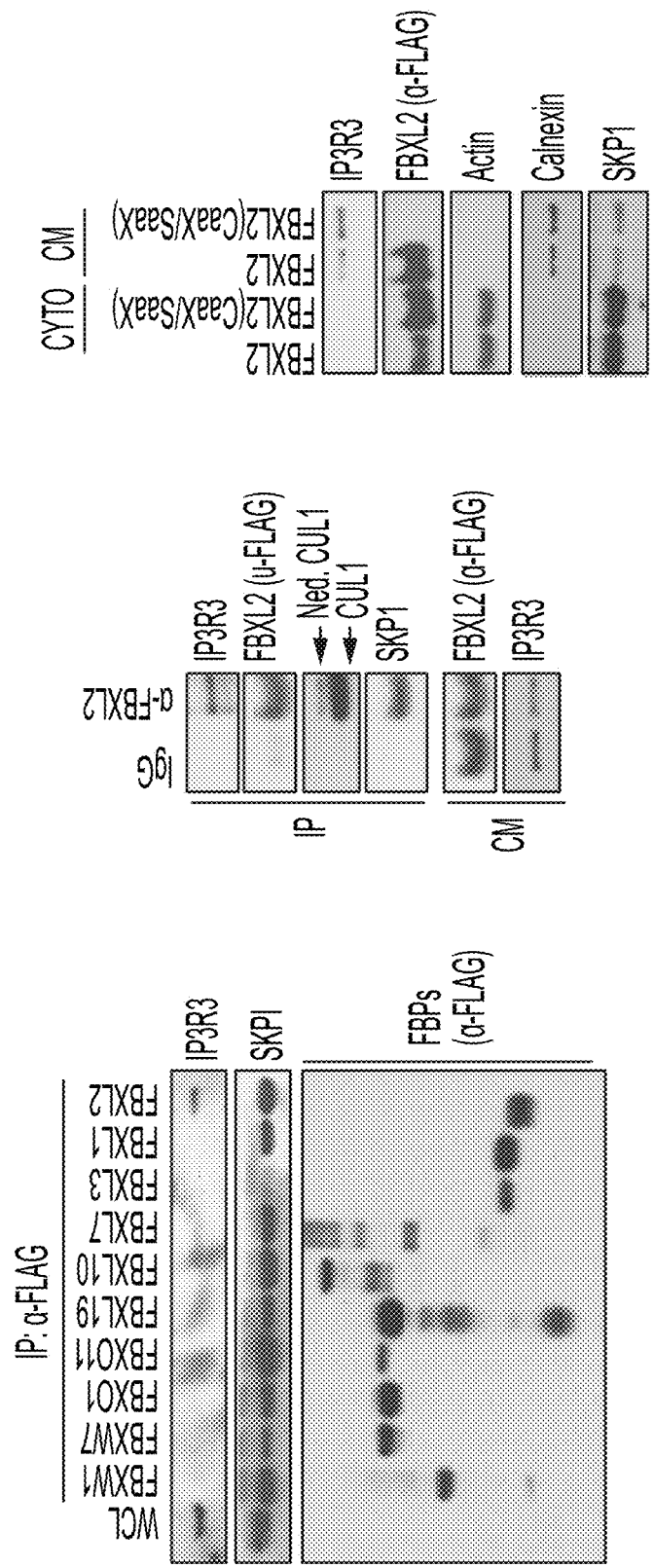

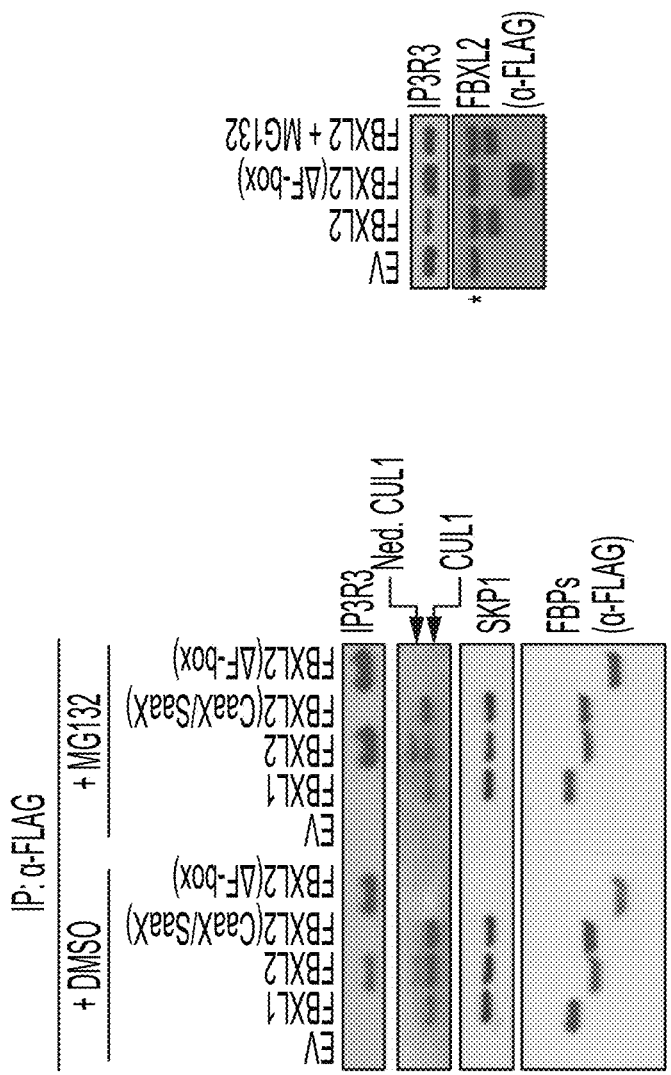

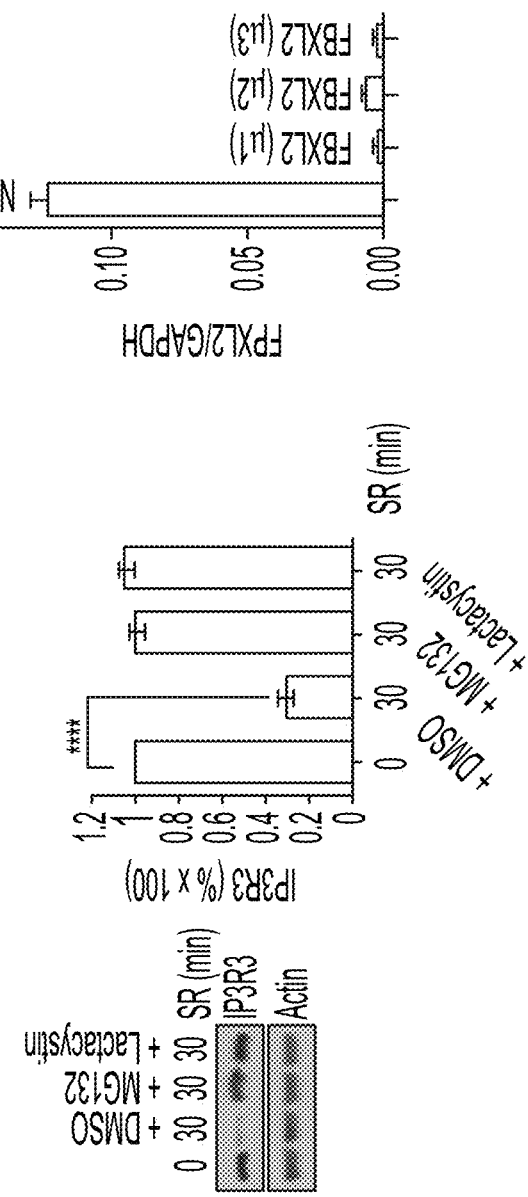

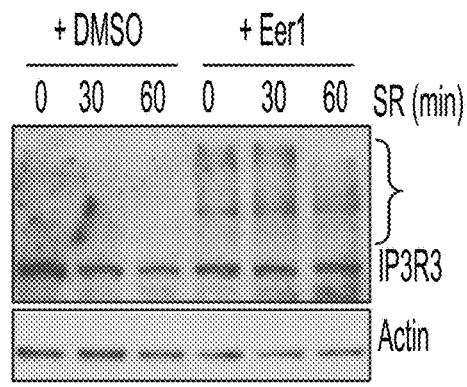
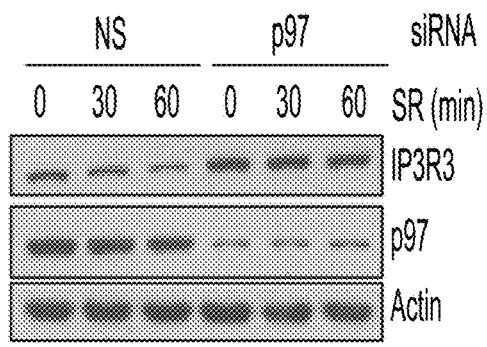
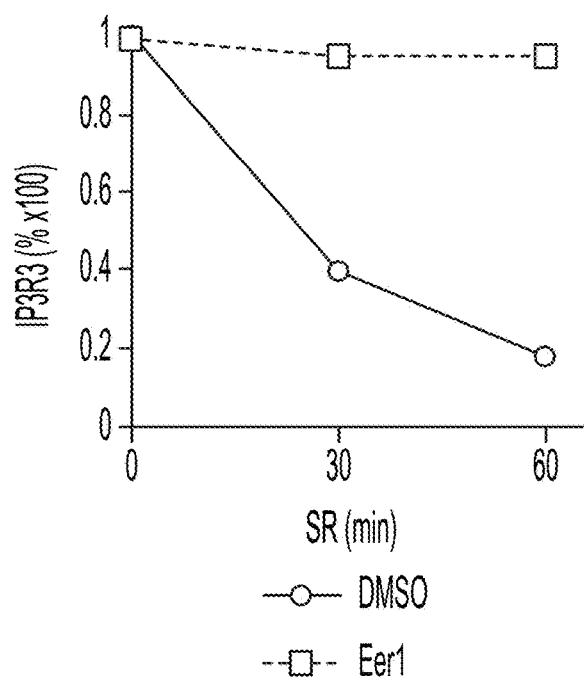
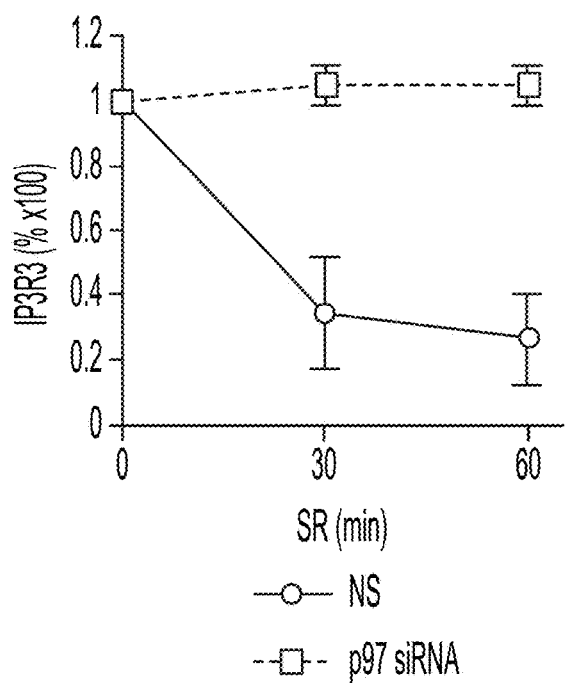
FIG. 6D
FIG. 6E

```
QKNAPYQHM FRLCYRVLRHSQEDY ------ Human
QKNAPYQHM FRLCYRVLRHSQEDY ------ Pig
QKNAPYQHM FRLCYRVLRHSQEDY ------ Bovine
QKNAPYQHM FRLCYRVLRHSQEDY ------ Dog
QKNAPYQHM FRLCYRVLRHSQEDY ------ Horse
QKNAPYQYM FRLCYRVLRHSQEDY ------ Rat
QKNAPYQYM FRLCYRVLRHSQEDY ------ Mouse
QKNAPYQYM FRLCYRVLRHSQEDY ------ Chicken
QKNAPYQYM FRLCYRVLRHSQEDY ------ Hamester
PKNSPYKNI FRLCYRILRLSQQDY ------ Drosophila
DSRNEIFKTM FQLCYCLLKYSQVSY ------ C. elegans
```

FIG. 8H

```
LEELSDQKNAPYQHMFRLCYRVLRHSQEDYRKNQEHIAKQF ------ IP3R3
LEDLGDQRYAPYKYMLRLCYRVLRHSQQDYRKNQEYIAKNF ------ IP3R2
LEELGDQRHAPFRHICRLCYRVLRHSQQDYRKNQEYIAKQF ------ IP3R1
```

FIG. 8I

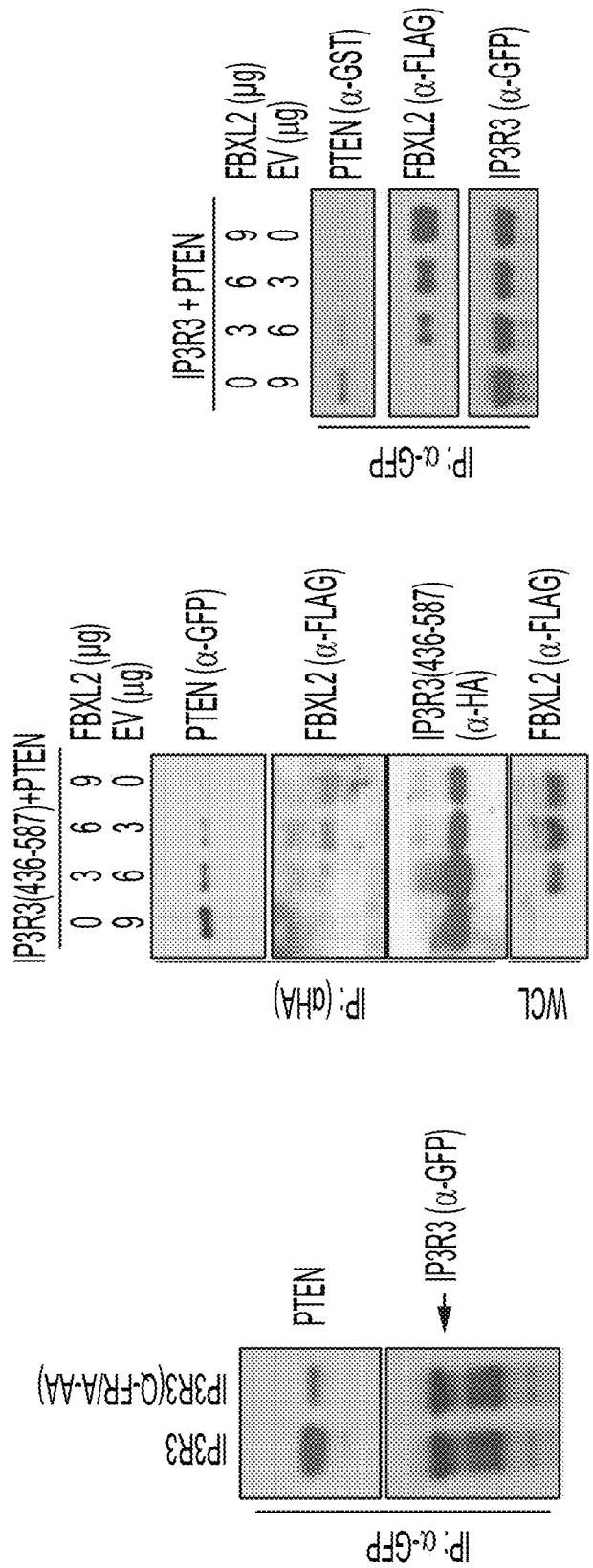

FIG. 13A

|  | A548* |
|---|---|
| TOT No. of clones screened | 10 |
| No. of ITPR3 Heterozygous Knock-in clones | 0 |
| No. of ITPR3 Homozygous Knock-in clones | 10 |
| No. of ITPR3 Wild-Type clones | 0 |

* ITPR3 Copy Number = 2

|  | PC-3* |
|---|---|
| TOT No. of clones screened | 10 |
| No. of ITPR3 Heterozygous Knock-in clones | 3 |
| No. of ITPR3 Homozygous Knock-in clones | 6 |
| No. of ITPR3 Wild-Type clones | 1 |

* ITPR3 Copy Number = 4

FIG. 13C

GERANYLGERANYLTRANSFERASE I INHIBITOR FOR TREATMENT OF A PTEN DEFECTIVE CANCER

CROSS REFERENCE TO RELATED APPLICATIONS

This application is a national stage application filed under 35 U.S.C. § 371 of International PCT Application No. PCT/US2018/036206, filed on Jun. 6, 2018, which claims the benefit of U.S. Provisional Application No. 62/515,990, filed on Jun. 6, 2017; U.S. Provisional Application No. 62/519,001, filed on Jun. 13, 2017; and U.S. Provisional Application No. 62/671,717, filed on May 15, 2018; applications which are incorporated herein by reference in their entirety.

STATEMENT REGARDING FEDERALLY SPONSORED RESEARCH

This invention was made with Government Support under Grant No. CA76584 awarded by the National Institutes of Health. The Government has certain rights to the invention.

BACKGROUND

The phosphatase and tensin homologue (PTEN) gene is frequently mutated or lost in human tumours and syndromes that predispose individuals to cancer. What is needed are new methods for treating cancers with PTEN mutations or cancers where the PTEN pathway is affected.

The compositions and methods disclosed herein address these and other needs.

SUMMARY

In one aspect, disclosed herein is a method of treating a cancer in a subject, the method comprising administering to the subject a therapeutically affective amount of a geranylgeranyltransferase I (GGTase I) inhibitor; wherein the cancer comprises a defective PTEN, a hyperactivated FBXL2, or a low level of IP3R3.

In some embodiments, the GGTase inhibitor comprises the compound GGTI-2418, or a pharmaceutically acceptable salt or hydrate thereof.

In some embodiments, the cancer comprises a defective PTEN. In some embodiments, the defective PTEN is a mutant PTEN. In some embodiments, the defective PTEN is due to low levels of PTEN gene expression.

In some embodiments, the cancer comprises a hyperactivated FBXL2. In some embodiments, the cancer comprises a low level of IP3R3.

In some embodiments, the method further comprises administering to the subject photodynamic therapy (PDT).

In some embodiments, the method further comprises administering to the subject a pharmaceutically effective amount of an Akt inhibitor. In some embodiments, the method further comprises administering to the subject a pharmaceutically effective amount of TCN-P (an Akt inhibitor).

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The accompanying figures, which are incorporated in and constitute a part of this specification, illustrate several aspects described below.

FIGS. 1A, 1B, 1C, 1D, 1E, 1F, 1G, and 1H show FBXL2-mediated degradation of IP3R3 controls Ca2+ flux and sensitivity to apoptosis. FIG. 1A shows concentrations of cytosolic Ca2+ ([Ca2+]c) were measured with aequorin in response to agonist stimulation (ATP) in NHFs exponentially growing (Exp), serum-starved (SS), or re-stimulated with serum (SR) (passage 2 or 3), which were transfected with an siRNA targeting FBXL2 or a non-silencing (n.s.) siRNA. Left, two representative traces. Right, quantification of three independent experiments. P values were calculated by one-way ANOVA and multiple-comparisons test. Error bars indicate s.e.m. 1b, 1c, and 1d, Apoptosis evaluated after treatment with H2O2 using automated nuclei count analysis of twenty randomly chosen fields following a 16 h treatment (1b), immunoblot detection of cleaved PARP and cleaved caspase-3 following a 3 h treatment (1c), and automated analysis of cells with released cytochrome c (Cyt c) from 80 randomly chosen fields following a 3 h treatment (1d). NHFs were transfected with the indicated siRNAs. Where indicated, cells were pre-treated for 30 min with cyclosporin A (CsA). P values were calculated by one-way ANOVA and multiple-comparisons test. Error bars indicate s.e.m. FIG. 1E shows that COS-7 cells were transfected with either GFP-tagged IP3R3 or GFP-tagged IP3R3(Q-FR/A-AA). 16 h post-transfection, cells were serum-starved for 48 h, and then re-stimulated with serum for the indicated times. Cells were harvested, and whole-cell lysates (WCLs) were immunoblotted as indicated. The graph shows the quantification of IP3R3 levels from two independent experiments. Figure if shows that COS-7 cells transfected with the indicated constructs were serum-starved for 20 h and then re-stimulated with serum for 4 h. WCLs were immunoblotted as indicated. FIG. 1g shows that COS-7 cells transfected with the indicated constructs were serum-starved for 20 h, re-stimulated for 4 h with or without MG132, and treated with ATP. Left, representative traces show concentrations of cytosolic Ca2+ measured with aequorin. Right, quantification of three independent experiments. P values were calculated by one-way ANOVA and multiple-comparisons test. Error bars indicate s.e.m. 1h and 1i, COS-7 cells transfected with the indicated constructs were serum-starved for 20 h, re-stimulated with serum for 4 h, and then treated with H2O2. Apoptosis shown in 1h was evaluated as in 1b, except that H2O2 treatment was for 5 h. Analysis of cytochrome c release shown in 1i was evaluated as in 1d. P values were calculated by unpaired t-test. Error bars indicate s.e.m. Unless otherwise noted, experiments were performed at least three times.

FIGS. 2A, 2B, 2C, and 2D show that PTEN loss promotes IP3R3 degradation via FBXL2, and the expression of IP3R3 and PTEN directly correlate in human prostate cancer. FIG. 2A shows that during 72 h of serum starvation, Pten+/+ and Pten−/− MEFs were transfected with the indicated siRNAs, re-stimulated with serum, and harvested at the indicated times for immunoblotting. l.e., long exposure; s.e., short exposure. The graph shows the quantification of IP3R3 levels from three independent experiments. Error bars indicate s.e.m. FIG. 2B shows that Pten−/− MEFs were transfected with the indicated siRNAs and, after 48 h, with the indicated constructs. After 24 h, cells were harvested and WCLs were immunoblotted as indicated. FIG. 2C shows that Pten−/− MEFs were transfected with the indicated siRNAs and, after 48 h, with the indicated constructs.

Concentrations of cytosolic Ca2+ were measured with aequorin in response to ATP. Left, representative traces. Right, quantification of three independent experiments. P values were calculated by one-way ANOVA and multiple-comparisons test. Error bars indicate s.e.m. FIG. 2d shows the percentage of prostate tumours with no, low or high PTEN expression that have low or high IP3R3 expression. Linear regression was determined using $\chi 2$ test r2=0.04041, P=0.0136. Unless otherwise noted, experiments were performed at least three times.

FIG. 3A shows that A549 cells were transfected with the indicated siRNAs and, after 48 h, treated with phthalocyanine, a photosensitizer used for PDT in patients with cancer. Top, cytosolic Ca2+ concentrations measured with Fura-2. Bottom (left and middle panels), mitochondrial Ca2+ mobilization in cells expressing the Ca2+-sensitive probe 4mtD3cpv. Left panels show representative traces, and panels on their right show quantifications of areas under the curve represented as percentage change compared to empty-vector-transfected cells, which were set as 100%. Bottom (right panel), immunoblots of a representative experiment. P values were calculated by one-way ANOVA and multiple-comparisons test. Error bars indicate s.e.m. FIG. 3b shows that parental A459 and two IP3R3(Q-FR/A-AA) A549 knock-in clones (1 and 3) were processed and analysed as in a. Unless otherwise noted, experiments were performed at least three times.

FIG. 4A shows NOD/SCID gamma mice were subcutaneously inoculated with 2×106 A549 cells stably transfected with either an empty vector or IP3R3(Q-FR/A-AA). Implanted xenotransplanted mice, chosen randomly, were subjected to two rounds of PDT (see arrows) or left untreated (UT); n=4-6 mice per group. Left panel, tumour growth kinetics at the indicated time points. Middle panel, representative tumours imaged with IRDye 2-DG at the end of the experiment. Top right panel, representative excised tumours imaged 60 days post-injection. Bottom right panel, quantification of tumour weights. P values for the tumour volume and weight at day 60 were calculated by one-way ANOVA and multiple-comparisons test. Error bars indicate s.e.m. FIG. 4B shows Left panel, representative images of tumour sections from mice, which were injected with SR-FLIVO fluorescent probes to measure apoptosis. Middle panel, quantification of apoptosis. Right panel, corresponding immunoblots from homogenized tumours. AFU, arbitrary fluorescence units. P values were calculated by one-way ANOVA and multiple-comparisons test. Error bars indicate s.e.m. FIG. 4C shows NOD/SCID gamma mice were subcutaneously injected with A549 cells. Implanted xenotransplanted mice, chosen randomly, were treated with GGTi-2418 alone or in combination with PDT; n=5-6 mice per group. Left panel, tumour growth kinetics for the indicated time points. Top right panel, representative excised tumours imaged 60 days post-injection. Bottom right panel, quantification of tumour weights. P values for the tumour volume and weight at day 60 were calculated by one-way ANOVA and multiple-comparisons test. Error bars indicate s.e.m. FIG. 4D shows Left panel, PDT-induced apoptosis detected by NIR-FLIVO fluorescently labelled probes in the subcutaneous tumour masses of mice treated with or without GGTi-2418. Middle panel, quantification of apoptosis. Right panel, corresponding immunoblots from homogenized tumours. P values were calculated by one-way ANOVA and multiple-comparisons test. Error bars indicate s.e.m. Unless otherwise noted, experiments were performed at least three times.

FIGS. 5A, 5B, 5C, 5D, 5E, 5F, 5G, 5H, 5I, 5J, 5K, and 5L show that IP3R3 is targeted for proteasomal degradation by SCF (that is, Skp1-Cul1-FBXL2). FIG. 5A shows that HEK293T cells were transfected with the indicated Flag-tagged F-box proteins (FBPs). 24 h post-transfection, cells were treated with MG132 for 3 h before harvesting for immunoprecipitation and immunoblotting as indicated. WCL, whole-cell lysate from untransfected cells. FIG. 5B shows that flag-tagged FBXL2 was stably expressed in HeLa cells. After harvesting, cells were lysed, and cell membranes (CM) were isolated and immunoprecipitated with either a normal mouse IgG or an anti-Flag antibody. Subsequently, immunoprecipitates were analysed by immunoblotting as indicated. The results of these experiments (n=2) indicate that FBXL2 is incorporated into a complete SCF ligase that binds its substrate(s) at cellular membranes. FIG. 5C shows that flag-tagged FBXL2 or Flag-tagged FBXL2(CaaX/SaaX) were transiently expressed in HeLa cells. After harvesting, cells were lysed and cytoplasmic (CYTO) and cell membrane (CM) fractions were isolated and analysed by immunoblotting as indicated. Actin and calnexin are used as markers for cytoplasmic and cell membrane fractions, respectively. This experiment was performed twice. FIG. 5D shows that HEK293T cells were transfected with either an empty vector (EV) or the indicated Flag-tagged proteins. 24 h post-transfection, where indicated, cells were treated with MG132 for 3 h before harvesting for immunoprecipitation and immunoblotting. Ned. CUL1, neddylated CUL1. This experiment shows that FBXL2, but not FBXL2(CaaX/SaaX), interacts with endogenous, neddylated CUL1. Since the covalent linkage of NEDD8 to CUL1 stimulates the ubiquitin ligase activity of SCFs and is promoted by the binding of the substrate to the F-box protein subunit, this result suggests that FBXL2 localization to cell membranes is required for substrate binding, which in turn stimulates CUL1 neddylation and SCF activation. Moreover, FBXL2($\Delta$F-box) bound more IP3R3 than wild-type FBXL2, and this difference could be abolished by treatment with MG132, supporting the hypothesis that FBXL2($\Delta$F-box) cannot mediate the degradation of IP3R3 since it does not form an active SCF complex. FIG. 5E shows that HEK293T cells were transfected with either an empty vector or the indicated Flag-tagged proteins. The experiment was performed in the presence or absence of MG132 as indicated. Whole-cell lysates were immunoblotted as indicated. The asterisk indicates a non-specific band. This experiment was performed twice. The fact that proteasome inhibitors prevented the decrease of IP3R3 levels upon re-addition of serum suggests that IP3R3 is degraded by the proteasome in response to mitogens, in agreement with previous studies reporting IP3Rs as substrates of the proteasome26,27. FIG. 5F shows that normal, non-transformed, non-immortalized, human diploid fibroblasts (NHFs) (passage 2) were serum-starved for 72 h and then re-stimulated with serum (SR) for 30 min in the absence or presence of either MG132 (a proteasome inhibitor) or lactacystin (another proteasome inhibitor) as indicated. The graph on the right shows the quantification of IP3R3 levels from three independent experiments. P values were calculated by unpaired t-test. Error bars indicate s.e.m. FIG. 5g shows that NHFs (passage 2) were transfected with either three different siRNAs targeting FBXL2 (each independently) or a non-silencing siRNA (NS). The graph shows FBXL2 mRNA levels analysed using real-time PCR in triplicate measurements. Error bars indicate s.e.m. The values represent the ratios between FBXL2 and GAPDH mRNAs. FIG. 5H shows the during a 72 h serum starvation, NHFs (passage 2 or 3) were transfected with either an siRNA targeting FBXL2 (#1) or a non-silencing siRNA (NS). Cells were subsequently stimulated with medium containing serum and harvested at the indicated times for immunoblotting. The graph shows the quantification of IP3R3 levels from three independent experiments. Error bars indicate s.e.m. FIG. 5i shows that during a 72 h serum starvation, NHFs (passage 3) were transfected with either siRNAs targeting FBXL2 (oligo #2 or #3) or a non-silencing siRNA (NS). Cells were subsequently stimulated with medium containing serum and harvested at the indicated time points for immunoblotting. The graph shows the quantification of IP3R3 levels from three independent experiments. Error bars indicate s.e.m. FIG. 5J shows schematic representation of the FBXL2 genomic locus and gRNAs target location. Exon 2 and exon 3 refer to the human FBXL2 gene in NC_000003.12 (GRCh38.p7 (Gene Bank ID: 3129728)). FIG. 5K shows schematic representation of FBXL2 CRISPR-Cas9 mutagenesis outcomes. A first round of CRISPR-Cas9 gene editing yielded no homozygous FBXL2-knockout clones. A secondary round of CRISPR-Cas9 gene editing was carried out in three FBXL2+/− hTERT RPE-1 clones, which resulted in cell death, suggesting that FBXL2 is required for cell fitness and it is not possible to generate FBXL2-knockout cells. Similar results were obtained in A549 cells (data not shown). FIG. 5L shows that FBXL2+/+ and FBXL2+/− RPE-1-hTERT cells (knock-in clones 2 and 3) were serum-starved for 72 h and subsequently stimulated with medium containing serum for 90 min, after which cell extracts were immunoblotted for the indicated proteins. The graph shows the quantification of IP3R3 levels from three independent experiments. Unless otherwise noted, experiments were performed at least three times.

FIGS. 6A, 6B, 6C, 6D, 6E, 6F, 6G, and 6H that the degradation of IP3R3 is dependent on FBXL2 localization to cell membranes and on the segregase activity of p97. FIG. 6a shows that HeLa cells were transfected with GFP-tagged FBXL2 and then treated with either DMSO or GGTI-2418 for 16 h. Live cell imaging was carried out with an LSM510 confocal microscope using a 63× objective. Scale bars, 10 μm. FIG. 6b shows that NHFs were incubated with GGTi-2418 for 30 h and then with cycloheximide (CHX) and ATP. Cells were subsequently harvested at the indicated times for immunoblotting. The graph shows the quantification of IP3R3 levels from two independent experiments. FIG. 6c shows that NHFs (passage 3), HeLa and HEK293T cells were incubated with GGTi-2418 for the indicated times. Cells were subsequently harvested for immunoblotting. This experiment was performed once. FIG. 6d shows that NHFs (passage 3) were serum-starved for 72 h, treated with either DMSO or Eer1, and then re-stimulated with serum (SR) for the indicated times. The graph shows the quantification of IP3R3 levels from two independent experiments. The bracket on the right marks a ladder of bands which, presumably, are ubiquitinated species of IP3R3 that are not degraded when p97 is inhibited. FIG. 6e shows that during a 72 h serum starvation, NHFs (passage 3 and 4) were transfected with either an siRNA targeting p97 or a non-silencing siRNA (NS). Cells were subsequently stimulated with medium containing serum and harvested at the indicated time points for immunoblotting. The graph shows the quantification of IP3R3 levels from three independent experiments. Error bars indicate s.e.m. These results, together with those shown in d, are in agreement with the findings that IP3Rs are ubiquitinated while they are membrane-associated, and those showing that p97 promotes the degradation of IP3Rs27,28. Thus, we propose that, after its FBXL2-mediated ubiquitination, IP3R3 is extracted from cell membranes by the segregase activity of p97 to be degraded by the proteasome. FIG. 6f shows that HEK293T cells were transfected with either an empty vector (EV) or the indicated GFP-tagged and HA-tagged proteins. 24 h post-transfection, cells were treated with MG132 for 3 h before harvesting for immunoprecipitation and immunoblotting as indicated. This experiment was performed twice. FIGS. 6g and 6h show that HEK293T cells were transfected with Flag-tagged FBXL2 and the indicated versions of tagged IP3R3. After immunopurification with an anti-Flag resin, in vitro ubiquitination of IP3R3 was performed in the presence of UAE1, Ubch3, Ubch5 and ubiquitin (Ub). Where indicated, an excess of methylated ubiquitin (methyl-Ub), which blocks chain extension, was added to the in vitro reactions. The presence of methyl-Ub resulted in the disappearance of the highest molecular weight forms of IP3R3, demonstrating that the high molecular weight forms of IP3R3 are indeed polyubiquitinated species of the protein. Samples were analysed by immunoblotting with the indicated antibodies. The bracket on the right marks a ladder of bands corresponding to ubiquitinated IP3R3. Immunoblots of whole-cell lysates (WCL) are shown at the bottom. Unless otherwise noted, experiments were performed at least three times.

FIG. 7A shows that concentrations of mitochondrial Ca2+ were measured with mitochondria-targeted aequorin in response to agonist stimulation (ATP, a purinergic GPCR (G-protein-coupled receptor) agonist) in exponentially growing (EXP), serum-starved (SS), and serum re-stimulated (SR) NHFs (passage 4 or 5). Quantification of three independent experiments is shown and represented as percentage increase compared to EXP cells, which were set as 100%. P values were calculated by one-way ANOVA and multiple-comparisons test. Error bars indicate s.e.m. FIG. 7B shows that concentrations of mitochondrial Ca2+ were measured as in a in exponentially growing (EXP), serum-starved (SS), and serum re-stimulated for one hour (SR) NHFs (passage 5) transfected with either an siRNA targeting FBXL2 (#1) or a non-silencing siRNA (NS). Quantifications and P value analyses was performed as in a. FIG. 7C shows that concentrations of cytosolic Ca2+ were measured with aequorin in response to agonist stimulation (ATP) in NHFs (passage 2) re-stimulated with serum for one hour (SR) in the absence or presence of MG132 or GGTi2418. On the left, representative traces. On the right, quantification of three independent experiments. P values were calculated by a one-way ANOVA and multiple-comparisons test. Error bars indicate s.e.m. FIGS. 7D and 7E shows that cHeLa cells were transfected with either an empty vector (EV), FBXL2 or FBXL2(CaaX/SaaX). Concentrations of cytosolic (7d) and mitochondrial (7e) Ca2+ were measured with the appropriate aequorin in response to agonist stimulation (ATP). On the left, representative traces. On the right, quantifications of three independent experiments. P values were calculated by one-way ANOVA and multiple-comparisons test. Error bars indicate s.e.m. FIG. 7f shows that concentrations of mitochondrial Ca2+ were measured with mitochondrial targeted aequorin upon treatment with H2O2 in NHFs (passage 2) transfected with either an siRNA targeting FBXL2 (#1) or a non-silencing siRNA (NS). On the left, representative traces. On the right, quantifications of areas under the curve (AUC)

are represented as percentage increase compared to NS-transfected cells, which were set as 100%. P values were calculated by unpaired t-test. Error bars indicate s.e.m. At the bottom, immunoblots of cell lysates of a representative experiment upon treatment with H2O2 for 3 h. FIG. 7g shows that HeLa cells transfected with either an empty vector (EV), FBXL2 or FBXL2(CaaX/SaaX) were treated with either H2O2 (for 5 h) or etoposide (for 5 h). Induction of cell death was evaluated after treatment with H2O2 using automated nuclei count analysis of twenty randomly chosen fields. P values were calculated by one-way ANOVA and multiple-comparisons test. Error bars indicate s.e.m. FIG. 7h shows that COS-7 cells expressing either IP3R3 or IP3R3 (Q-FR/A-AA) in combination with Flag-tagged FBXL2 were serum-starved for 20 h, re-stimulated with serum (SR) for 4 h with or without MG132, as indicated, and treated with ATP. Left, representative traces showing concentrations of mitochondrial Ca2+ measured with mitochondrial targeted aequorin. Right, quantification of three independent experiments. P values were calculated by one-way ANOVA and multiple-comparisons test. Error bars indicate s.e.m. FIG. 7i shows that concentrations of mitochondrial Ca2+ were measured with mitochondria-targeted aequorin upon treatment with H2O2 in COS-7 cells expressing either IP3R3 or IP3R3(Q-FR/A-AA) in combination with Flag-tagged FBXL2. Left, representative traces. Middle, quantifications of areas under the curve represented as percentage increase compared to NS-transfected cells, which were set as 100%. P values were calculated using an unpaired t-test. Error bars indicate s.e.m. Right, immunoblots of cell lysates of a representative experiment upon treatment with H2O2 for 3 h. Unless otherwise noted, experiments were performed at least three times.

FIGS. 8A, 8B, 8C, 8D, 8E, 8F, 8G, 8H, 8I, and 8J show Mapping of the FBXL2-binding domain in IP3R3, and evidence that the N-terminal suppressor domain inhibits the IP3R3-FBXL2 interaction. FIG. 8a shows a schematic representation of IP3R3 mutants. Binding of IP3R3 to FBXL2 is indicated with the symbol (+). FIG. 8B shows that HEK293T cells were transfected with GFP-tagged FBXL2 and the indicated Flag-tagged IP3R3 truncated mutants. Whole-cell lysates (WCL) were immunoprecipitated (IP) with anti-Flag resin and proteins were immunoblotted as indicated. This experiment was performed twice. FIG. 8C shows that HEK293T cells were transfected with GFP-tagged FBXL2 and HA-tagged IP3R3(1-602) constructs. Sixteen hours after transfection, cells were incubated with MG132 for 3 h before stimulation with ATP for 30 min Whole-cell lysates (WCL) were immunoprecipitated (IP) with an anti-HA resin and proteins were immunoblotted as indicated. This experiment was performed twice. FIG. 8d shows that HeLa cells stably transfected with Flag-tagged FBXL2 under the control of a doxycycline-inducible promoter were treated with doxycycline (0.4 µg ml-1) for 16 h and incubated with or without MG132 (during the last 3 h), in the presence or absence of MRS 2578, an antagonist of P2Y6 receptor (during the last 90 min), as indicated. Cells were subsequently treated with or without ATP for 30 min Whole-cell lysates were immunoprecipitated (IP) with an anti-Flag resin and proteins were immunoblotted as indicated. Right panel shows quantifications of IP3R3 levels compared to untreated cells (UT), which were set as 100%. P values were calculated by one-way ANOVA and multiple-comparisons test. Error bars indicate s.e.m. The fact (shown in b) that fragments encoding IP3R3(436-587) and IP3R3(227-602) interact with FBXL2 better than the IP3R3(1-602) fragment suggests that the N terminus of IP3R3 inhibits the interaction between FBXL2 and IP3R3. It has been shown that removal of the N-terminal suppressor domain (amino acids 1-226) increases the binding of IP3 to the IP3 binding core domain (amino acids 227-579), and IP3 binding evokes conformational changes that open the suppressor domain29-32. These conformational changes may allow FBXL2 to access the degron of IP3R3 (that is, the amino acid region required for binding to FBXL2). Thus, in agreement with previous data indicating that IP3 causes the ubiquitination and downregulation of IP3Rs (ref. 27), our results suggest that IP3 promotes the binding of FBXL2 to IP3R3 and that FBXL2 preferentially binds IP3R3 in its open conformation (upon IP3 binding). Accordingly, treatment of cells with ATP, which induces IP3 production and repositioning of the N-terminal suppressor domain, increased the binding between FBXL2 and IP3R3, particularly if proteasomal degradation was inhibited by MG132. This suggests that once IP3 (produced after ATP stimulation) unmasks the IP3R3 degron, FBXL2 binds IP3R3 and this interaction is preserved when FBXL2-mediated degradation of IP3R3 is inhibited. So, ATP and MG132 appear to synergize with each other in promoting and preserving the FBXL2-IP3R3 interaction, respectively. FIG. 8e shows serum-starved (SS) and exponentially (EXP) growing NHFs (passage 2 and 3) were treated with or without ATP as indicated. Cells were subsequently harvested at the indicated time points for immunoblotting. The graph shows the quantification of IP3R3 levels. Error bars indicate s.e.m. FIG. 8f shows HEK293T cells were transfected with GFP-tagged FBXL2 and the indicated Flag-tagged IP3R3 deletion mutants (in the context of the 436-587 domain of IP3R3). Whole-cell lysates (WCL) were immunoprecipitated (IP) with anti-Flag resin, and proteins were immunoblotted as indicated. This experiment was performed twice. FIG. 8g shows that the experiment was performed twice as in f, except that different IP3R3 mutants were used. h, Alignment of the amino acid regions containing the FBXL2-binding motif in IP3R3 orthologues. FIG. 8i shows alignment of the amino acid regions containing the FBXL2-binding motif in human IP3R3 with the corresponding region in IP3R1 and IP3R2. FIG. 8j shows that HEK293T cells were transfected with the indicated constructs. Whole-cell lysates (WCL) were immunoprecipitated (IP) with anti-Flag resin and immunoblotted as indicated. The bracket on the right marks a ladder of bands corresponding to polyubiquitinated IP3R3. This experiment was performed twice. Unless otherwise noted, experiments were performed at least three times.

FIG. 9A shows HEK293T cells were transfected with the indicated Flag-tagged constructs encoding tumour suppressors and oncoproteins with established roles in Ca2+ homeostasis and that are known to localize to the endoplasmic reticulum-mitochondria interface (AKT1, BCL2, p53, PML4, PTEN and KRAS4B). Of those, AKT1, BCL2, PML4 and PTEN are known IP3R3 interactors33-39. Twenty-four hours post-transfection, cells were harvested for anti-Flag immunoprecipitations and immunoblotting as indicated. Asterisks denote Flag-tagged proteins. This experiment was performed twice. FIGS. 9B and 9C show Whole-cell lysates (WCL) from HEK293T cells were immunoprecipitated with the indicated antibodies and immunoblotted as indicated. This experiment was performed twice. FIG. 9d shows Pten+/+ and Pten−/− MEFs were incubated with cycloheximide (CHX) for the indicated times. Cells were subsequently harvested for immunoblotting as indicated. The graph on the right shows the quantification of IP3R3 levels from two independent experiments. FIG. 9e shows FBXL2 mRNA levels in Pten+/+ and Pten−/− MEFs analysed using real-time PCR in triplicate measurements (±s.e.m.). The values represent the ratios between FBXL2 and GAPDH mRNAs. This experiment was performed twice. FIG. 9f shows Pten+/+ and Pten−/− MEFs were transfected for 48 h with either an siRNA targeting FBXL2 (#1) or a non-silencing siRNA (NS). Subsequently, MEFs were transfected with Flag-TR-TUBE cDNA. Whole-cell lysates (WCL) were immunoprecipitated (IP) with anti-Flag resin and immunoblotted as indicated. The bracket on the right marks a ladder of bands corresponding to polyubiquitinated IP3R3. This experiment was performed twice. FIG. 9g shows U87 and A549 cells were transfected with either GFP-tagged PTEN, GFP-tagged PTEN(C124S), or an empty vector (EV) as indicated. Cells were subsequently harvested and whole-cell lysates were immunoblotted as indicated. Long (l.e.) and short (s.e.) exposures are shown for IP3R3. FIG. 9h shows Pten−/− MEFs were processed as in (FIG. 2c). Concentrations of mitochondrial Ca2+ were measured with mitochondria-targeted aequorin in response to agonist stimulation (ATP). Top, representative traces. Bottom, quantification of three independent experiments. P values were calculated by one-way ANOVA and multiple comparisons test. Error bars indicate s.e.m. FIG. 9i shows HEK293T cells were transfected with either GFP-tagged wild-type PTEN or the indicated GFP-tagged cancer-associated PTEN mutants. Whole-cell lysates (WCL) were immunoprecipitated (IP) with anti-GFP resin and proteins were immunoblotted as indicated. This experiment was performed twice. Unless otherwise noted, experiments were performed at least three times.

FIGS. 10A, 10B, 10C, 10D, 10E, 10F, 10G, 10H, 10I, 10J, and 10K show PTEN competes with FBXL2 for the binding to IP3R3, and the levels of IP3R3 and PTEN directly correlate in cancer cell lines and human prostate tumours. FIG. 10A shows left, schematic representation of IP3R3 mutants used for binding site mapping. Binding of IP3R3 to FBXL2 and PTEN is indicated with the symbol (+). Right, HEK293T cells were transfected with GFP-tagged PTEN and the indicated HA-tagged IP3R3 truncated mutants. Whole-cell lysates (WCL) were immunoprecipitated (IP) with anti-HA resin and immunocomplexes were probed with antibodies to the indicated proteins. This experiment was performed twice. FIG. 10B shows HEK293T cells were transfected with GFP-tagged IP3R3 and IP3R3(Q-FR/A-AA). Whole-cell lysates were immunoprecipitated (IP) with an anti-GFP resin and proteins were immunoblotted as indicated. FIG. 10C shows HEK293T cells were co-transfected, as indicated, with GFP-tagged PTEN, HA-IP3R3 (436-587), and increasing amounts of Flag-tagged FBXL2. Whole-cell lysates (WCL) were immunoprecipitated (IP) with anti-HA resin and proteins were immunoblotted as indicated. This experiment was performed twice. FIG. 10d shows HEK293T cells were co-transfected, as indicated, with GST-tagged PTEN, GFP-tagged IP3R3, and increasing amounts of Flag-tagged FBXL2. Whole-cell lysates were immunoprecipitated (IP) with anti-GFP resin and proteins were immunoblotted as indicated. This experiment was performed twice. FIG. 10e shows HEK293T cells were co-transfected, as indicated, with Flag-tagged FBXL2, HA-tagged IP3R3(436-587), and increasing amounts of either GFP-tagged PTEN or the indicated GFP-tagged cancer-associated PTEN mutants. Whole-cell lysates were immunoprecipitated (IP) with anti-HA resin and proteins were immunoblotted as indicated. This experiment was performed twice. FIG. 10f shows HEK293T cells were transfected with either an siRNA targeting PTEN or a non-silencing siRNA (NS), as indicated. After 48 h, cells were transfected with Flag-tagged FBXL2. Sixteen hours after the second transfection, whole-cell lysates were immunoprecipitated (IP) with anti-Flag resin. Immunocomplexes and WCLs were immunoblotted as indicated. FIG. 10g shows whole-cell lysates from the indicated cancer cell lines were immunoblotted as indicated. This experiment was performed twice. FIG. 10h shows FBXL2 mRNA levels in the indicated cell lines analysed using real-time PCR in triplicate measurements (±s.e.m.). The values represent the ratios between FBXL2 and GAPDH mRNAs. This experiment was performed once. FIG. 10i shows H460 and A549 cells were incubated with cycloheximide (CHX) for the indicated times. Cells were subsequently harvested and processed for immunoblotting as indicated. Long (l.e.) and short (s.e.) exposures are shown for IP3R3. The graph shows the quantification of IP3R3 levels from three independent experiments. Error bars indicate s.e.m. FIG. 10j shows U87 and A549 cells were treated with GGTi-2418 for 16 h where indicated. Cells were subsequently harvested and whole-cell lysates were immunoblotted as indicated. This experiment was performed twice. FIG. 10k shows representative immunohistochemistry staining images of human prostate tumour specimens with no, low or high levels of PTEN protein. Levels of IP3R3 in consecutive tissue slides are shown. Scale bars correspond to 50 μm. Unless otherwise noted, experiments were performed at least three times.

FIG. 11A show thatMEFs were transfected for 48 h with either a non-silencing siRNA (NS) or siRNAs targeting PTEN or IP3R3 as indicated. Cells were loaded with Fura-2 dye for Ca2+ mobilization analysis upon treatment with PDT. Representative traces (left panel) show cytosolic calcium mobilization. Quantifications are shown in the right panel. P values were calculated by one-way ANOVA and multiple-comparisons test. ARmax, maximum variation in peak values of 340/380 ratiometric analysis. Error bars indicate s.e.m. FIG. 11B shows matched-pair cell lines expressing wild-type PTEN or displaying low or no PTEN expression (that is, DU134 and PC3 (prostate cancer cell lines); H460 and A549 (lung cancer cell lines); 451-LU and Wm493b (melanoma cell lines), respectively) were loaded with Fura-2 dye for Ca2+ mobilization analysis upon PDT treatment. Representative traces (left panels) show cytosolic calcium mobilization. Bar graphs (middle panels) show the quantification of three independent experiments. Right panels show corresponding whole cell extracts immunoblotted as indicated. P values were calculated by unpaired t-test. Error bars indicate s.e.m. FIG. 11C shows A549 cells were transiently transfected with either GFP-tagged PTEN, GFP-tagged PTEN(C124S), or an empty vector as indicated. Cells were treated with phthalocyanine, a photosensitizer used for PDT in patients with cancer. Top panels show cytosolic Ca2+ concentrations measured with Fura-2. Bottom (left and middle panels), mitochondrial Ca2+ mobilization in cells expressing the Ca2+ sensitive probe 4mtD3cpv. Left panels show representative traces, and panels on their right show quantifications of areas under the curve represented as percentage increase compared to empty-vector-transfected cells, which were set as 100%. Right bottom panel shows immunoblots of cell lysates of a representative experiment. P values were calculated by one-way ANOVA and multiple-comparisons test. Error bars indicate s.e.m. FIG. 11D shows PC3 cells were transiently transfected with either GFP-tagged PTEN, GFP-tagged PTEN(C124S), or an empty vector (EV) as indicated. Cells were loaded with Fura-2 dye for Ca2+ mobilization analysis upon PDT treatment. Representative traces show cytosolic calcium mobilization. Bar graphs show the quantification of three independent experiments. Right panel shows immunoblots of cell lysates of a representative experiment. P values were calculated by one-way ANOVA and multiple-comparisons test. Error bars indicate s.e.m. Unless otherwise noted, experiments were performed at least three times.

FIG. 12A shows that PC3 cells (top panels) and Wm493b cells (bottom panels) were transfected with a non-silencing siRNA (NS) or siRNAs targeting either FBXL2, IP3R3 or both FBXL2 and IP3R3. Cells were loaded with Fura-2 dye for Ca2+ mobilization analysis upon PDT treatment. Representative traces show cytosolic calcium mobilization. Bar graphs show the quantification of three independent experiments. ARmax, maximum variation in peak values of 340/380 ratiometric analysis. P values were calculated by one-way ANOVA and multiple-comparisons test. Error bars indicate s.e.m. FIG. 12B shows that PC3 cells (left panels), Wm493b cells (middle panels) and A549 cells (right panels) expressing either GFP-tagged IP3R3(Q-FR/A-AA) or an empty vector (EV) were loaded with Fura-2 dye for Ca2+ mobilization analysis upon PDT treatment. Representative traces show cytosolic calcium mobilization. Bar graphs show the quantification of three independent experiments. Statistical analysis was performed with unpaired t-tests. Error bars indicate s.e.m. Bottom panels show corresponding immunoblots of cell lysates of representative experiments. Unless otherwise noted, experiments were performed at least three times.

Figure 13A:
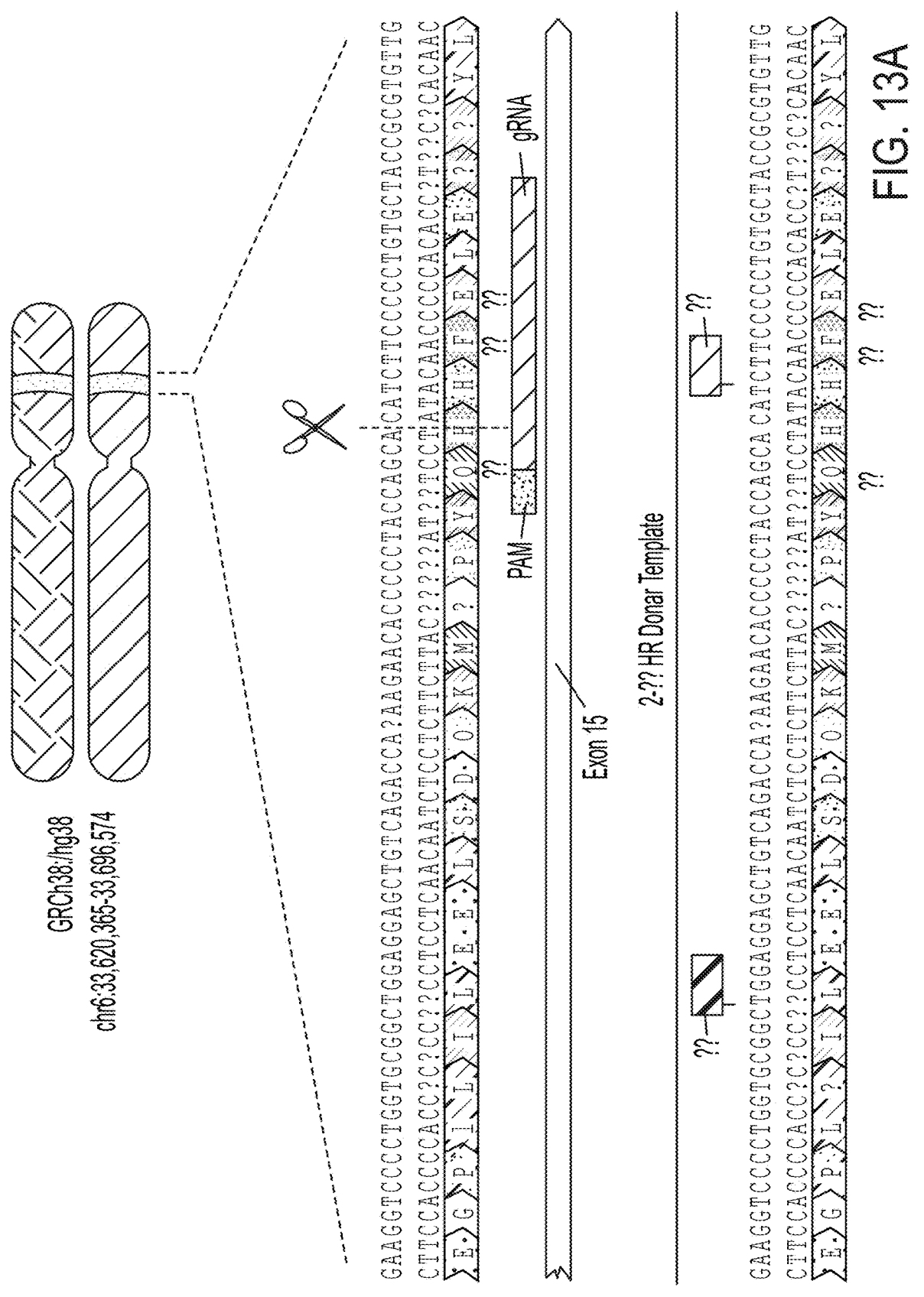

FIGS. 13A, 13B, 13C, 13D, 13E, 13F, and 13G show that non-degradable IP3R3 mutant sensitizes tumours to photodynamic therapy. FIG. 13A shows aschematic representation of the ITPR3 genomic locus and gRNA target location. Exon 15 refers to human ITPR3 gene (GRCh38.p7 (Gene Bank ID: 31297280)). Silent mutations are shown as lower case letters and indicated by asterisks. FIG. 13b shows wild-type genomic DNA template and knock-in mutant sequences identified by TOPO-TA cloning of ITPR3 PCR from three independent A549 and PC3 clones are depicted. FIG. 13c shows a schematic representation of the ITPR3 CRISPR-Cas9 mutagenesis outcomes for A549 and PC3 cells. FIG. 13d shows whole-cell lysates from A549 parental cells and three independent IP3R3(Q-FR/A-AA) knock-in clones were immunobloted as indicated. FIG. 13e shows A549 parental cells and IP3R3(Q-FR/A-AA) knock-in cells (clones 1 and 3) were incubated with cycloheximide (CHX) for the indicated times. Cells were subsequently harvested for immunoblotting as indicated. The graph shows the quantification of IP3R3 levels from three independent experiments. Error bars indicate s.e.m. FIG. 13f shows whole-cell lysates from PC3 parental cells and an IP3R3(Q-FR/A-AA) knock-in clone (#1) were immunoblotted as indicated. FIG. 13g shows that PC3 parental cells and the IP3R3(Q-FR/A-AA) knock-in PC3 clone 1 were treated with phthalocyanine, a photosensitizer used for PDT in patients with cancer. Left panel, cytosolic Ca2+ concentrations measured with Fura-2. Middle panel, quantifications of areas under the curve represented as percentage increase compared to empty-vector-transfected cells, which were set as 100%. Right panel, immunoblots of cell lysates from a representative experiment. The P value was calculated by unpaired t-test. Error bars indicate s.e.m. Unless otherwise noted, experiments were performed at least three times.

FIG. 14a shows tumour growth of PC3 cell xenografts analysed as in (FIG. 4a). Error bars indicate s.e.m. FIG. 14b shows the apoptosis of PC3 cell xenografts analysed as in (FIG. 4b). Error bars indicate s.e.m. FIG. 14c shows A549 parental cells and IP3R3(Q-FR/A-AA) knock-in clone no. 3 were processed as in (FIG. 4a). FIG. 14d shows A549 parental cells and IP3R3(Q-FR/A-AA) knock-in clone no. 3 were processed as in (FIG. 4b). FIG. 14e shows a model of the FBXL2- and PTEN-dependent regulation of IP3R3 function in energy production and cell death. In response to IP3 production, IP3R3 releases calcium from the endoplasmic reticulum to mitochondria, stimulating oxidative phosphorylation and ATP production. To avoid persistent calcium flux and consequent cell death, IP3R3 is degraded via FBXL2. PTEN competes with FBXL2 for IP3R3 binding, thus increasing the stability of IP3R3 and promoting apoptosis. The fact that PTEN (C124S), a catalytically dead mutant, binds IP3R3, competes with FBXL2 for IP3R3 binding, and stabilizes IP3R3 in a manner that is identical to wild-type PTEN, strongly indicates that neither the lipid phosphatase activity nor the protein phosphatase activity of PTEN are required to positively affect IP3R3 stability. PTEN(G129E), a mutant displaying a greatly reduced lipid phosphatase activity, but retaining protein phosphatase activity, also binds IP3R3 and competes with FBXL2 in a manner that is indistinguishable from wild-type PTEN. However, PTEN(C124S) induces an effect on Ca2+ mobilization that is significant, but not as high as that evoked by wild-type PTEN and PTEN(G129E). This suggests that, in addition to its phosphatase-independent ability to stabilize IP3R3, the protein phosphatase activity of PTEN may contribute to Ca2+ flux, as suggested by Bononi et al.40. Our findings reveal the molecular basis (that is, the competition with FBXL2 for IP3R3 binding) by which PTEN(C124S) is able to promote both the mitochondrial Ca2+ response and apoptosis. Importantly, according to this model, FBXL2 is a pro-survival factor, which complements its known role in the efficient activation of the PI3K cascade9. Finally, our results show that both FBXL2 and PTEN do not affect the levels and stability of IP3R1 and IP3R2. We note that one peptide corresponding to IP3R2 was identified in the original purification of the FBXL2 complex. Moreover, the FBXL2 complex purified by the Harper group contained one peptide corresponding to IP3R1 (ref. 41). FBXL2 binds both p85α and p85β; but it targets only p85β for degradation9. We speculate that the binding to p85α is indirect and occurs because of the presence in the cell of p85α-p85β heterodimers. Since IP3R1, IP3R2, and IP3R3 also form heteromers21,42,43, it is possible that FBXL2 indirectly binds one or both IP3R3 paralogues, but only targets IP3R3 for degradation. Unless otherwise noted, experiments were performed at least three times.

DETAILED DESCRIPTION

Figure 1A:
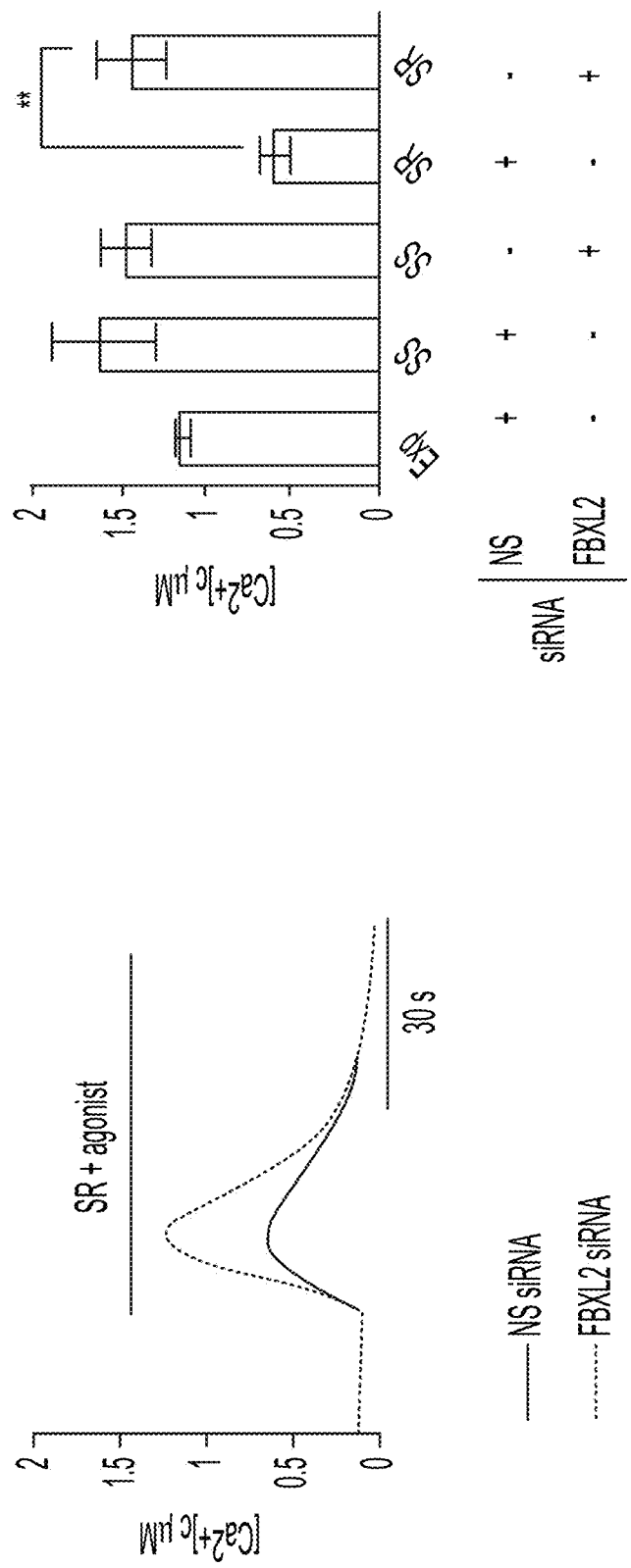

Protein geranylgeranylation is a lipid post translational modification that is required for the cellular localization and the function of many proteins that are intimately involved in cell proliferation, survival, invasion and metastasis (Zhang F L, et al. Annu Rev Biochem 1996 65:241-269; Sebti S M, et al. Oncogene 2000 19:6584-6593). This posttranslational modification is catalyzed by the enzyme Geranylgeranyl-transferase 1 (GGT-1) that transfers the lipid geranylgeranyl to cysteines of proteins that end at their c-termini with the consensus tetrapeptide sequence CAAX (where C is cysteine, A is often a aliphatic amino acid and X is preferably leucine or iso leucine) (SEQ ID NO:1). The fact that geranylgeranylation is required for the cancer-causing activity of many small GTPases prompted development of GGT-1 inhibitors (GGTIs) as anti-cancer agents (Berndt N, et al. Nat Rev Cancer 2011 11:775-791). One of these GGTI-2418, a CAAX peptidomimetic, has reached phase I clinical trials (O'Dwyer P J, et al. Ann Oncol 2010 21:ii42). The contributions of geranylgeranylated (GG) proteins to malignant transformation are well documented in solid tumors, but little is known about their contributions to hematological malignancies. Indeed, GG proteins such as RhoA, RhoC, Rac1, Rac3, Ra1A and Ra1B have been shown to mediate many cancer hallmarks including tumor survival, uncontrolled proliferation, anchorage-independent growth, invasion and/or metastasis in solid tumors (Berndt N, et al. Nat Rev Cancer 2011 11:775-791; Falsetti S C, et al. Mol Cell Biol 2007 27:8003-8014; Berndt N, et al. Nat Protoc 2011 6:1775-1791). Validation for targeting protein geranylgeranylation as a therapeutic approach for solid tumors is also supported by several finding including the demonstration, using knockout mice, that GGT-1 is required for KRas-driven lung tumorigenesis but is dispensable for postnatal development (Berndt N, et al. Nat Rev Cancer 2011 11:775-791; Berndt N, et al. Nat Protoc 2011 6:1775-1791). Furthermore, pharmacological inhibition of protein geranylgeranylation suppresses malignant transformation in cultured pancreatic, breast and other human cancer cells and inhibits tumor growth in several animal models of solid tumors (Falsetti S C, et al. Mol Cell Biol 2007 27:8003-8014; Berndt N, et al. Nat Protoc 2011 6:1775-1791; Kazi A, et al. Mol Cell Biol 2009 29:2254-2263).

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs.

Methods

In one aspect, disclosed herein is a method of treating a cancer in a subject, the method comprising administering to the subject a therapeutically affective amount of a geranylgeranyltransferase I (GGTase I) inhibitor; wherein the cancer comprises a defective PTEN, a hyperactivated FBXL2, or a low level of IP3R3.

In some embodiments, the GGTase inhibitor comprises the compound GGTI-2418, or a pharmaceutically acceptable salt or hydrate thereof. In some embodiments, the GGTase inhibitor comprises the compound GGTI-2417, or a pharmaceutically acceptable salt or hydrate thereof.

In some embodiments, the cancer comprises a defective PTEN. In some embodiments, the defective PTEN is a mutant PTEN (such as a point mutation, insertion, deletion, etc). In some embodiments, the defective PTEN is due to low levels of PTEN gene expression. In some embodiments, the defective PTEN is due to low levels of PTEN protein. It is understood and herein contemplated that a defect causing low levels of PTEN is not limited to mutations of PTEN, but can refer to defects in regulatory proteins (polymerases, ribosomes), enzymes, and/or regulatory elements (activators, enhancers, insulators, silencers) that alter the gene or protein expression level of PTEN or a combination of PTEN mutation and reduced gene or protein expression level of PTEN. Accordingly, in some aspects, the defective PTEN is a nonmutated PTEN that is abnormally regulated such that gene or expression level of PTEN is low. In some embodiments, the cancer comprises an abnormal PTEN.

As used herein, the term "low levels of PTEN" or "low PTEN" means that for a particular type of cancer cell, the level of PTEN, as measured for example by mRNA or protein levels, is decreased compared to the wild type level of PTEN in a cancer cell of the same type of cancer. In some embodiments, the decrease is compared to the wild type level of PTEN in a healthy patient (for example, without a cancer). In some embodiments, the decrease is compared to the wild type level of PTEN in the same types of cells as the corresponding cancer cells. Levels of other mRNAs or proteins (for example, IP3R3) can also be similarly measured to determine "low levels". It is understood that "low levels" can refer to any amount of decrease relative to normal or wild-type levels of PTEN expression in a cancer cell of the same type of cancer or the wild type level of PTEN from a healthy cell. The decrease can be any decrease relative to the wild type level of PTEN in a cancer cell of the same type of cancer or the wild type level of PTEN from a healthy cell including 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12,13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95.5, 96, 96.5, 97, 97.5, 98, 98.5, 99, 99.1, 99.2, 99.3, 99.4, 99.5, 99.6, 99.7, 99.8, 99.9, or 100% decrease including, but not limited to any statistically significant decreases of PTEN. That is, the expression level of PTEN can be about 99.9, 99.8, 99.7, 99.6, 99.5, 99.4, 99.3, 99.2, 99.1, 99, 98.5, 98, 97.5, 97, 96.5, 96, 95.5, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, 0.1, or 0% of the PTEN expression levels in the wild type level of PTEN in a cancer cell of the same type of cancer or the wild type level of PTEN from a healthy cell. In one aspect, low levels of PTEN can include decreases so significant as to leave no PTEN expression (i.e., the gene or protein expression level of PTEN is zero) or levels of PTEN expression below level of detection or at trace amounts. Thus, in one aspect, low levels of PTEN or low PTEN refers to no or undetectable levels of PTEN (i.e., the gene or protein expression level of PTEN is zero, below detectable levels, or at trace amounts). In some embodiments, the cancer comprises a hyperactivated FBXL2. In some embodiments, the cancer comprises a low level of IP3R3.

In some embodiments, the method further comprises administering to the subject photodynamic therapy (PDT).

In one aspect, disclosed herein is a method of treating a cancer in a subject, the method comprising administering to the subject a therapeutically affective amount of an inhibitor of the interaction of Fbxl2 and IP3R3. In one aspect, disclosed herein is a method of treating a cancer in a subject, the method comprising administering to the subject a therapeutically affective amount of an inhibitor of the interaction of Fbxl2 and IP3R3; wherein the cancer comprises a defective PTEN, a hyperactivated FBXL2, or a low level of IP3R3.

In some embodiments, the inhibitor can include a small molecule, biological agent, peptide, antibody, single or double stranded nucleic acid, or siRNA.

In some embodiments, the method further comprises administering to the subject a pharmaceutically effective amount of an Akt inhibitor. In some embodiments, the method further comprises administering to the subject a pharmaceutically effective amount of TCN or TCN-P (an Akt inhibitor).

Akt inhibitors are known in the art. See for example, U.S. Pat. Nos. 9,511,084, 8,828,451, 9,498,492, US20080131526 which are hereby incorporated by reference for the teaching of these compounds.

In one aspect, the disclosed methods of treating a subject with a cancer can further comprise obtaining a protein or nucleic acid sample from a subject (including obtaining a tissue sample from which the nucleic acid or protein can be extracted or detected), conducting assay for detection of PTEN, FBXL2, or IP3R3 (such as, for example a microarray (such as, for example, gene, protein, or RNA array), SAGE, Northern blot, western blot, real-time PCR, enzyme-linked immunosorbent assay (ELISA), immunoelectrophoresis, immunohistochemistry, high-performance liquid chromatography (HPLC), or liquid chromatography-mass spectrometry (LC/MS)) on the nucleic acid or protein sample; wherein detection of defective PTEN, hyperactivated FBXL2, or a low level of IP3R3 indicates that a cancer should be treated with a geranylgeranyltransferase I (GGTase I) inhibitor, such as GGTI-2418; and administering to the subject with defective PTEN, hyperactivated FBXL2, or a low level of IP3R3 a geranylgeranyltransferase I (GGTase I) inhibitor, such as GGTI-2418.

It is understood and herein contemplated that one aspect of the disclosed methods utilize an assay for the detection of PTEN, FBXL2, or IP3R3 gene or protein expression levels to assess whether a geranylgeranyltransferase I (GGTase I) inhibitor, such as GGTI-2418 should be administered. Accordingly, in one aspect, disclosed herein are assays for determining when to treat cancer with a geranylgeranyltransferase I (GGTase I) inhibitor, such as GGTI-2418, comprising a microarray (such as, for example, a protein or RNA array), SAGE, Northern blot, western blot, real-time PCR, enzyme-linked immunosorbent assay (ELISA), immunoelectrophoresis, high-performance liquid chromatography (HPLC), or liquid chromatography-mass spectrometry (LC/MS) and primers, probes, or antibodies specific for the detection of PTEN, FBXL2 or IP3R3, wherein detection of defective PTEN, hyperactivated FBXL2, or a low level of IP3R3 indicates that a cancer should be treated with a geranylgeranyltransferase I (GGTase I) inhibitor, such as GGTI-2418.

In some embodiments, the GGTase I inhibitor is a peptide or peptidomimetic comprising the amino acid sequence CAAX (where C is cysteine, A is often a aliphatic amino acid and X is preferably leucine or iso leucine). For example, peptidomimetic GGTase I inhibitors, such as GGTI-2418, are disclosed in US 20120035184 A1 by Sebti, et al., which is hereby incorporated by reference for the teaching of these compounds. Structures for GGTI-2418 and its pro-drug methylester GGTI-2417 are shown below:

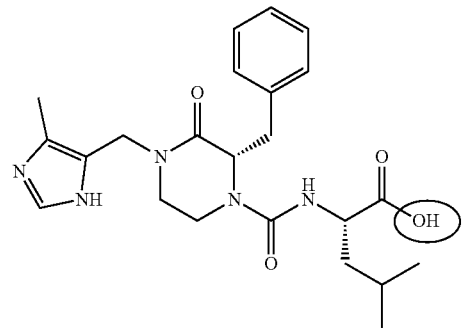

GGTI-2418

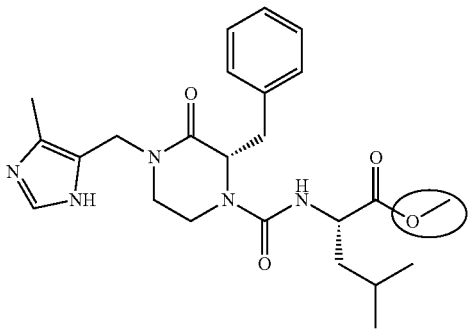

GGTI-2417

Numerous additional anti-cancer drugs are available for combination with the present method and compositions. The following is a non-exhaustive lists of anti-cancer (anti-neoplastic) drugs: Acivicin; Aclarubicin; Acodazole Hydrochloride; AcrQnine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflomithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine;

Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Pipsulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

The compounds, compositions, and methods described herein are useful for the treatment of cancers or tumors (for example, wherein the cancer comprises a defective PTEN, a hyperactivated FBXL2, or a low level of IP3R3).

As contemplated herein, the cancer treated can be a primary tumor or a metastatic tumor. In one aspect, the methods described herein are used to treat a solid tumor, for example but not limited to, melanoma, lung cancer (including lung adenocarcinoma, basal cell carcinoma, squamous cell carcinoma, large cell carcinoma, bronchioloalveolar carcinoma, bronchogenic carcinoma, non-small-cell carcinoma, small cell carcinoma, mesothelioma); breast cancer (including ductal carcinoma, lobular carcinoma, inflammatory breast cancer, clear cell carcinoma, mucinous carcinoma, serosal cavities breast carcinoma); colorectal cancer (colon cancer, rectal cancer, colorectal adenocarcinoma); anal cancer; pancreatic cancer (including pancreatic adenocarcinoma, islet cell carcinoma, neuroendocrine tumors); prostate cancer; prostate adenocarcinoma; ovarian carcinoma (ovarian epithelial carcinoma or surface epithelial-stromal tumor including serous tumor, endometrioid tumor and mucinous cystadenocarcinoma, sex-cord-stromal tumor); liver and bile duct carcinoma (including hepatocellular carcinoma, cholangiocarcinoma, hemangioma); esophageal carcinoma (including esophageal adenocarcinoma and squamous cell carcinoma); oral and oropharyngeal squamous cell carcinoma; salivary gland adenoid cystic carcinoma; bladder cancer; bladder carcinoma; carcinoma of the uterus (including endometrial adenocarcinoma, ocular, uterine papillary serous carcinoma, uterine clear-cell carcinoma, uterine sarcomas, leiomyosarcomas, mixed mullerian tumors); glioma, glioblastoma, medulloblastoma, and other tumors of the brain; kidney cancers (including renal cell carcinoma, clear cell carcinoma, Wilm's tumor); cancer of the head and neck (including squamous cell carcinomas); cancer of the stomach (gastric cancers, stomach adenocarcinoma, gastrointestinal stromal tumor); testicular cancer; germ cell tumor; neuroendocrine tumor; cervical cancer; carcinoids of the gastrointestinal tract, breast, and other organs; signet ring cell carcinoma; mesenchymal tumors including sarcomas, fibrosarcomas, haemangioma, angiomatosis, haemangiopericytoma, pseudoangiomatous stromal hyperplasia, myofibroblastoma, fibromatosis, inflammatory myofibroblastic tumor, lipoma, angiolipoma, granular cell tumor, neurofibroma, schwannoma, angiosarcoma, liposarcoma, rhabdomyosarcoma, osteosarcoma, leiomyoma, leiomysarcoma, skin, including melanoma, cervical, retinoblastoma, head and neck cancer, pancreatic, brain, thyroid, testicular, renal, bladder, soft tissue, adenal gland, urethra, cancers of the penis, myxosarcoma, chondrosarcoma, osteosarcoma, chordoma, malignant fibrous histiocytoma, lymphangiosarcoma, mesothelioma, squamous cell carcinoma; epidermoid carcinoma, malignant skin adnexal tumors, adenocarcinoma, hepatoma, hepatocellular carcinoma, renal cell carcinoma, hypernephroma, cholangiocarcinoma, transitional cell carcinoma, choriocarcinoma, seminoma, embryonal cell carcinoma, glioma anaplastic; glioblastoma multiforme, neuroblastoma, medulloblastoma, malignant meningioma, malignant schwannoma, neurofibrosarcoma, parathyroid carcinoma, medullary carcinoma of thyroid, bronchial carcinoid, pheochromocytoma, Islet cell carcinoma, malignant carcinoid, malignant paraganglioma, melanoma, Merkel cell neoplasm, cystosarcoma phylloide, salivary cancers, thymic carcinomas, and cancers of the vagina among others. In one embodiment, the cancer is melanoma.

In one embodiment, the compounds, compositions, and methods described herein are useful for the treatment of cancers or tumors or proliferative disorder such as, but not limited to: multiple myeloma; Diffuse large B cell lymphoma; Follicular lymphoma; Mucosa-Associated Lymphatic Tissue lymphoma (MALT); Small cell lymphocytic lymphoma; Mediastinal large B cell lymphoma; Nodal marginal zone B cell lymphoma (NMZL); Splenic marginal zone lymphoma (SMZL); Intravascular large B-cell lymphoma; Primary effusion lymphoma; or Lymphomatoid granulomatosis; B-cell prolymphocytic leukemia; Hairy cell leukemia; Splenic lymphoma/leukemia, unclassifiable; Splenic diffuse red pulp small B-cell lymphoma; Hairy cell leukemia-variant; Lymphoplasmacytic lymphoma; Heavy chain diseases, for example, Alpha heavy chain disease, Gamma heavy chain disease, Mu heavy chain disease; Plasma cell myeloma; Solitary plasmacytoma of bone; Extraosseous plasmacytoma; Primary cutaneous follicle center lymphoma; T cell/histiocyte rich large B-cell lymphoma; DLBCL associated with chronic inflammation; Epstein-Barr virus (EBV)+ DLBCL of the elderly; Primary mediastinal (thymic) large B-cell lymphoma; Primary cutaneous DLBCL, leg type; ALK+ large B-cell lymphoma; Plasmablastic lymphoma; Large B-cell lymphoma arising in HHV8-associated multicentric; Castleman disease; B-cell lymphoma, unclassifiable, with features intermediate between diffuse large B-cell lymphoma; or B-cell lymphoma, unclassifiable, with features intermediate between diffuse large B-cell lymphoma and classical Hodgkin lymphoma.

In some embodiments, the cancer is selected from melanoma, prostate, glioblastoma, lung, and breast. In one embodiment, the cancer is melanoma. In one embodiment, the cancer is prostate cancer. In one embodiment, the cancer is glioblastoma. In one embodiment, the cancer is lung cancer. In one embodiment, the cancer is breast cancer.

Compositions

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

In certain examples, compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, or hydrates thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

A number of embodiments of the invention have been described. Nevertheless, it will be understood that various modifications may be made without departing from the spirit and scope of the invention. Accordingly, other embodiments are within the scope of the following claims.

EXAMPLES

The following examples are set forth below to illustrate the compositions, methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. PTEN Counteracts FBXL2 to Promote IP3R3- and Ca2+-Mediated Apoptosis Limiting Tumour Growth In response to environmental cues that promote IP3 (inositol 1,4,5-trisphosphate) generation, IP3 receptors (IP3Rs) located on the endoplasmic reticulum allow the 'quasisynaptical' feeding of calcium to the mitochondria to promote oxidative phosphorylation[1]. However, persistent Ca2+ release results in mitochondrial Ca2+ overload and consequent apoptosis[2]. Among the three mammalian IP3Rs, IP3R3 appears to be the major player in Ca2+-dependent apoptosis. Here we show that the F-box protein FBXL2 (the receptor subunit of one of 69 human SCF (SKP1, CUL1, F-box protein) ubiquitin ligase complexes[3]) binds IP3R3 and targets it for ubiquitin-, p97- and proteasome-mediated degradation to limit Ca2+ influx into mitochondria. FBXL2-knockdown cells and FBXL2-insensitive IP3R3 mutant knock-in clones display increased cytosolic Ca2+ release from the endoplasmic reticulum and sensitization to Ca2+-dependent apoptotic stimuli. The phosphatase and tensin homologue (PTEN) gene is frequently mutated or lost in human tumours and syndromes that predispose individuals to cancer[4]. We found that PTEN competes with FBXL2 for IP3R3 binding, and the FBXL2-dependent degradation of IP3R3 is accelerated in Pten−/− mouse embryonic fibroblasts and PTEN-null cancer cells. Reconstitution of PTEN-null cells with either wild-type PTEN or a catalytically dead mutant stabilizes IP3R3 and induces persistent Ca2+ mobilization and apoptosis. IP3R3 and PTEN protein levels directly correlate in human prostate cancer. Both in cell cultures and xenograft models, a non-degradable IP3R3 mutant sensitizes tumour cells with low or no PTEN expression to photodynamic therapy, which is based on the ability of photosensitizer drugs to cause Ca2+-dependent cytotoxicity after irradiation with visible light[5,6]. Similarly, disruption of FBXL2 localization with GGTi-2418, a geranylgeranyl transferase inhibitor[7], sensitizes xenotransplanted tumours to photodynamic therapy. In summary, we identify a novel molecular mechanism that limits mitochondrial Ca2+ overload to prevent cell death. Notably, we provide proof-of-principle that inhibiting IP3R3 degradation in PTEN-deregulated cancers represents a valid therapeutic strategy.

To identify FBXL2 substrates, FBXL2 was expressed in HEK293T cells, immunopurified and analysed for co-purifying proteins by mass spectrometry, which revealed the presence of two unique peptides corresponding to IP3R3. To confirm these results, we screened a panel of human F-box proteins and found that the only F-box protein that co-immunoprecipitated IP3R3 was FBXL2 (Extended Data FIG. 1a). FBXL2 co-immunoprecipitated SKP1, CUL1 and IP3R3 from the membrane fraction (Extended Data FIG. 1b). FBXL2 contains a C-terminal CaaX domain that is required for its geranylgeranylation and localization at cell membranes[8]. In contrast to wild-type FBXL2, FBXL2 (CaaX/SaaX), a geranylgeranylation-deficient mutant[9] in which a cysteine has been mutated to serine in the CaaX domain, did not fractionate with cellular membranes and did not interact with IP3R3 and neddylated CUL1 (Extended Data FIG. 1c, d).

We also observed that expression of wild-type FBXL2, but not FBXL2(ΔF-box), an inactive mutant, induced a decrease in the levels of IP3R3 (this decrease was rescued by MG132 treatment) and FBXL2(ΔF-box) bound more IP3R3 than wild-type FBXL2 (this difference was abolished by MG132 treatment) (Extended Data FIG. 1d, e).

Figure 2A:
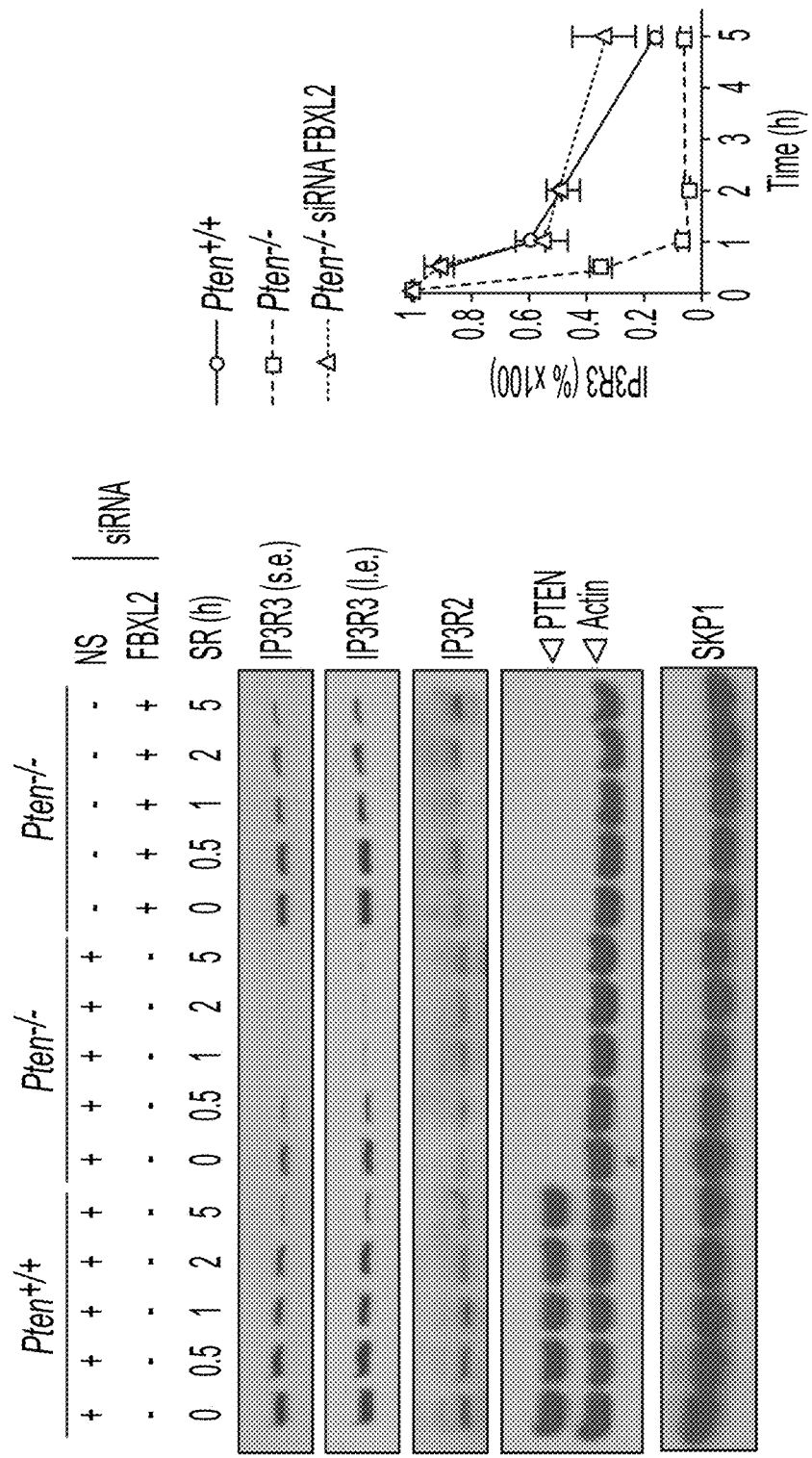
Figure 2B:
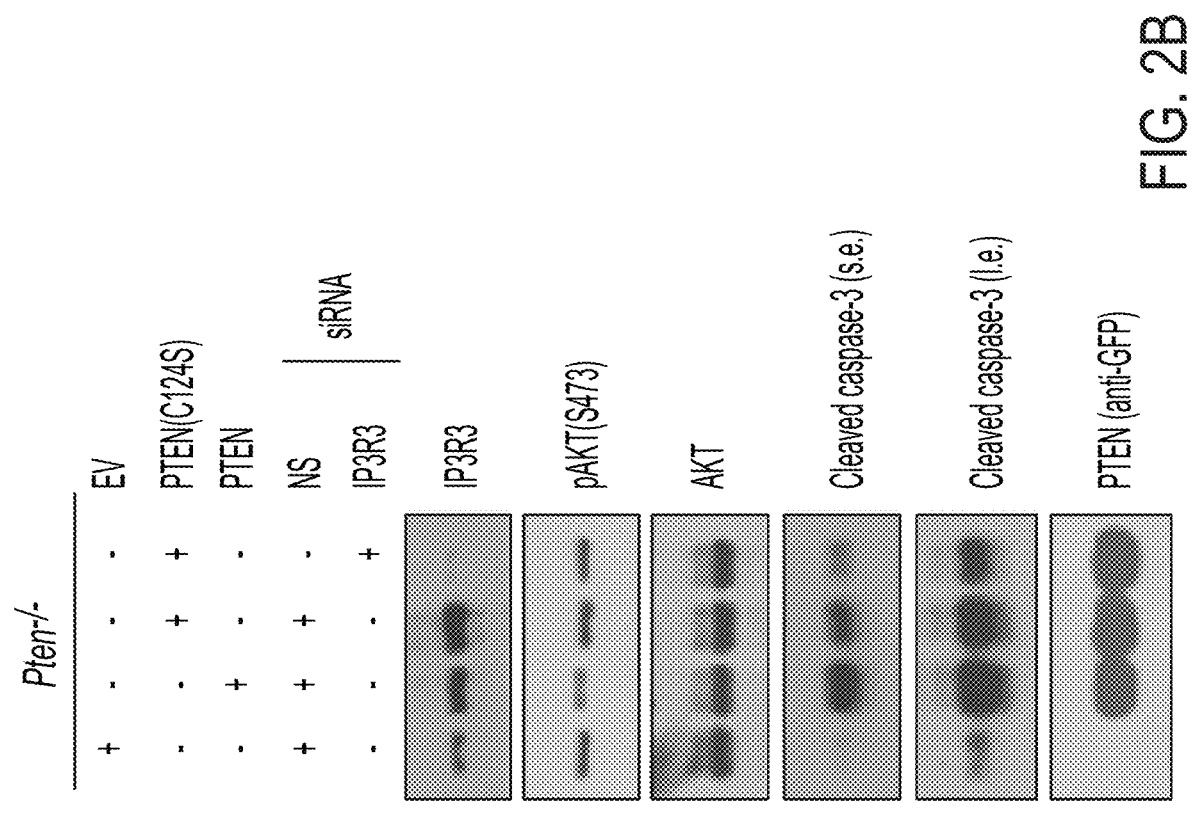
Figure 2C:
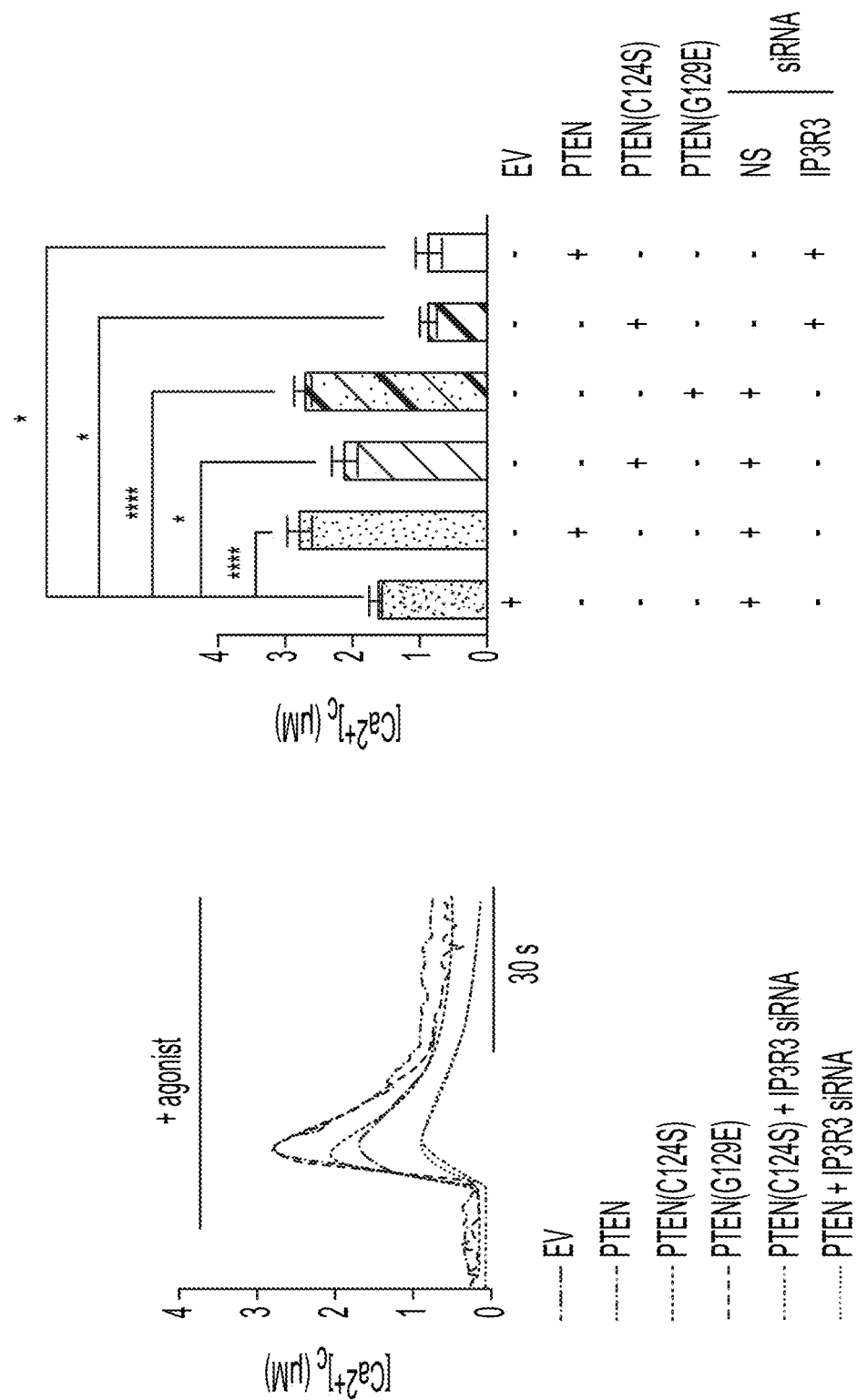
Figure 2D:
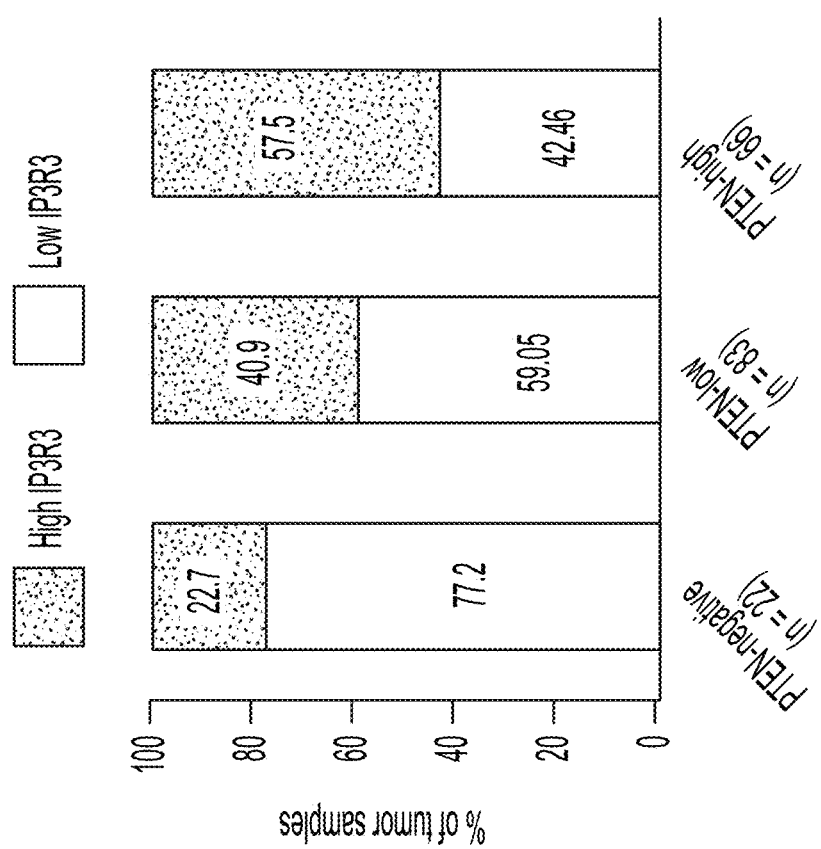
Figure 3A:
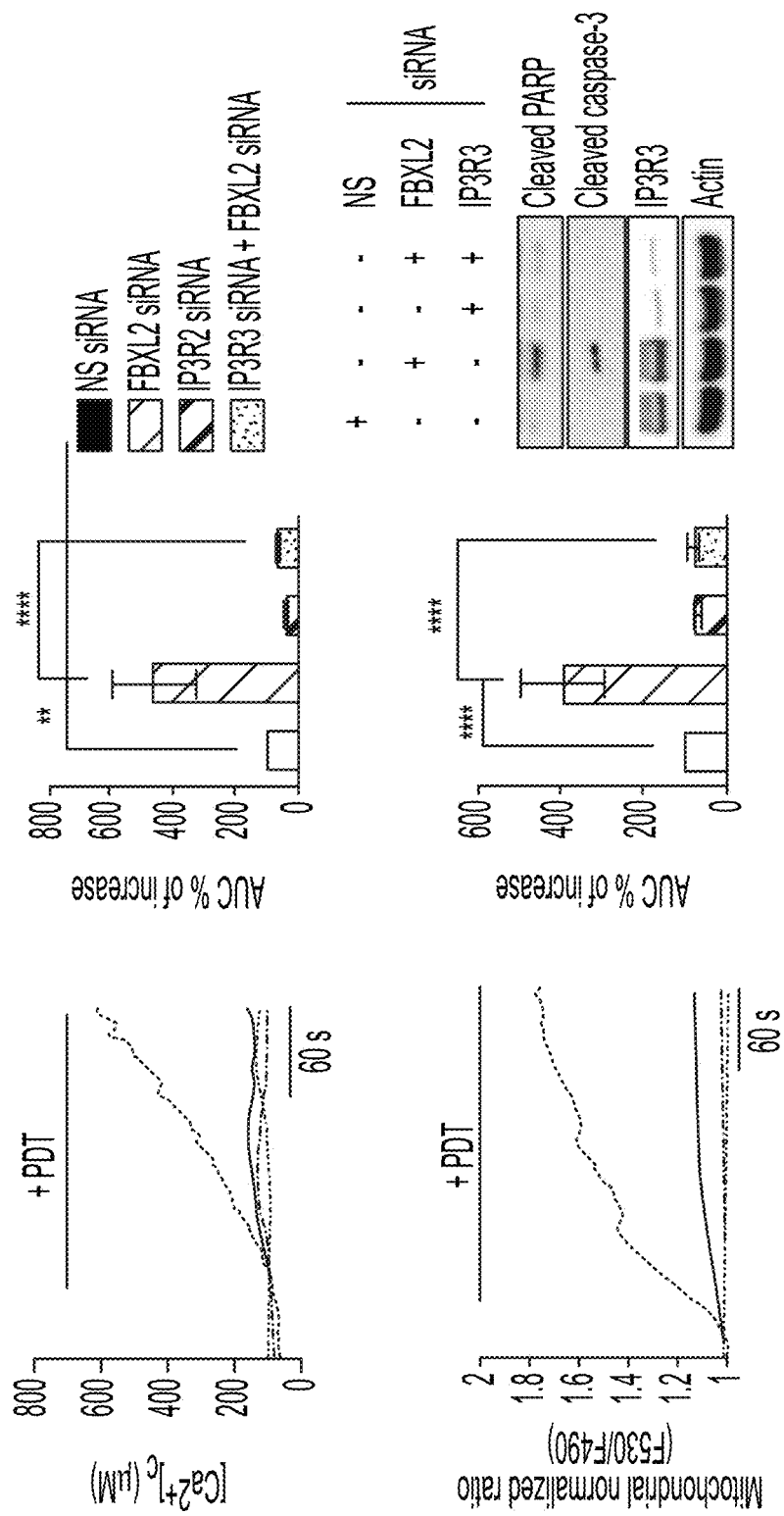
FIGS. 3A and 3B show that failure to degrade IP3R3 results in sensitization to PDT-induced apoptosis.
Figure 3B:
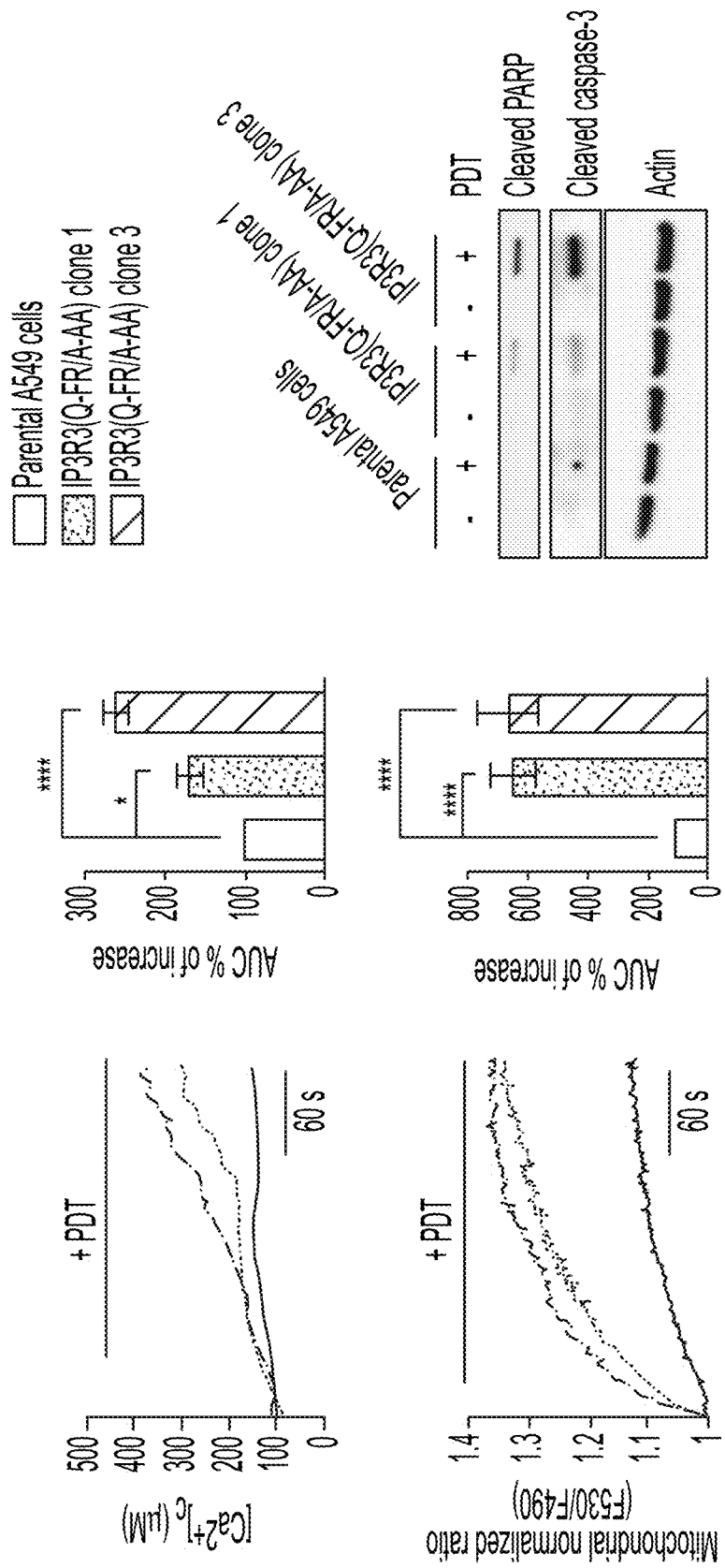

Since IP3-mediated Ca2+ release is stimulated by mitogens, we examined the impact of serum on IP3R3 levels. The growth of normal human fibroblasts (NHFs) was arrested by serum deprivation after which serum was reintroduced. The levels of IP3R3 decreased in control cells, but much less in cells treated with MG132 or lactacystin, or in which FBXL2 was silenced (Extended Data FIG. 1f-i). In hTERT RPE-1 cells, elimination of one FBXL2 allele resulted in IP3R3 stabilization (Extended Data FIG. 1j-l). GGTi-2418 treatment delocalized FBXL2 and stabilized IP3R3 (Extended Data FIG. 2a-c). Eer1, an inhibitor of p97 (also known as VCP or Cdc48), a segregase that extracts ubiquitinated proteins from the cellular membrane to facilitate their proteasomal degradation[10], blocked IP3R3 degradation (Extended Data FIG. 2d). Silencing of p97 inhibited the serum-mediated degradation of IP3R3, and both FBXL2 and IP3R3 co-immunoprecipitated with p97 (Extended Data FIG. 2e, f). Finally, immunopurified FBXL2, but not FBXL2 (ΔF-box), promoted the in vitro ubiquitination of IP3R3 (Extended Data FIG. 2g, h). To investigate the role of FBXL2 in Ca2+ homeostasis, we measured the changes in Ca2+ concentration in both the cytosol and mitochondria of NHFs in response to ATP, a purinergic GPCR agonist that induces IP3 production and rapid flow of Ca2+ from the endoplasmic reticulum to the mitochondria[11]. Serum starvation caused an increase and serum re-addition induced a decrease in Ca2+ mobilization (FIG. 1a and Extended Data FIG. 3a). FBXL2 silencing or treatment with MG132 or GGTi-2418 inhibited the serum-mediated decrease in Ca2+ mobilization (FIG. 1a and Extended Data FIG. 3b, c). Conversely, cells engineered to express FBXL2, but not FBXL2(CaaX/SaaX), displayed low IP3R3 levels and a decrease in Ca2+ mobilization (Extended Data FIGS. 1c and 3d, e).

Figure 1B:
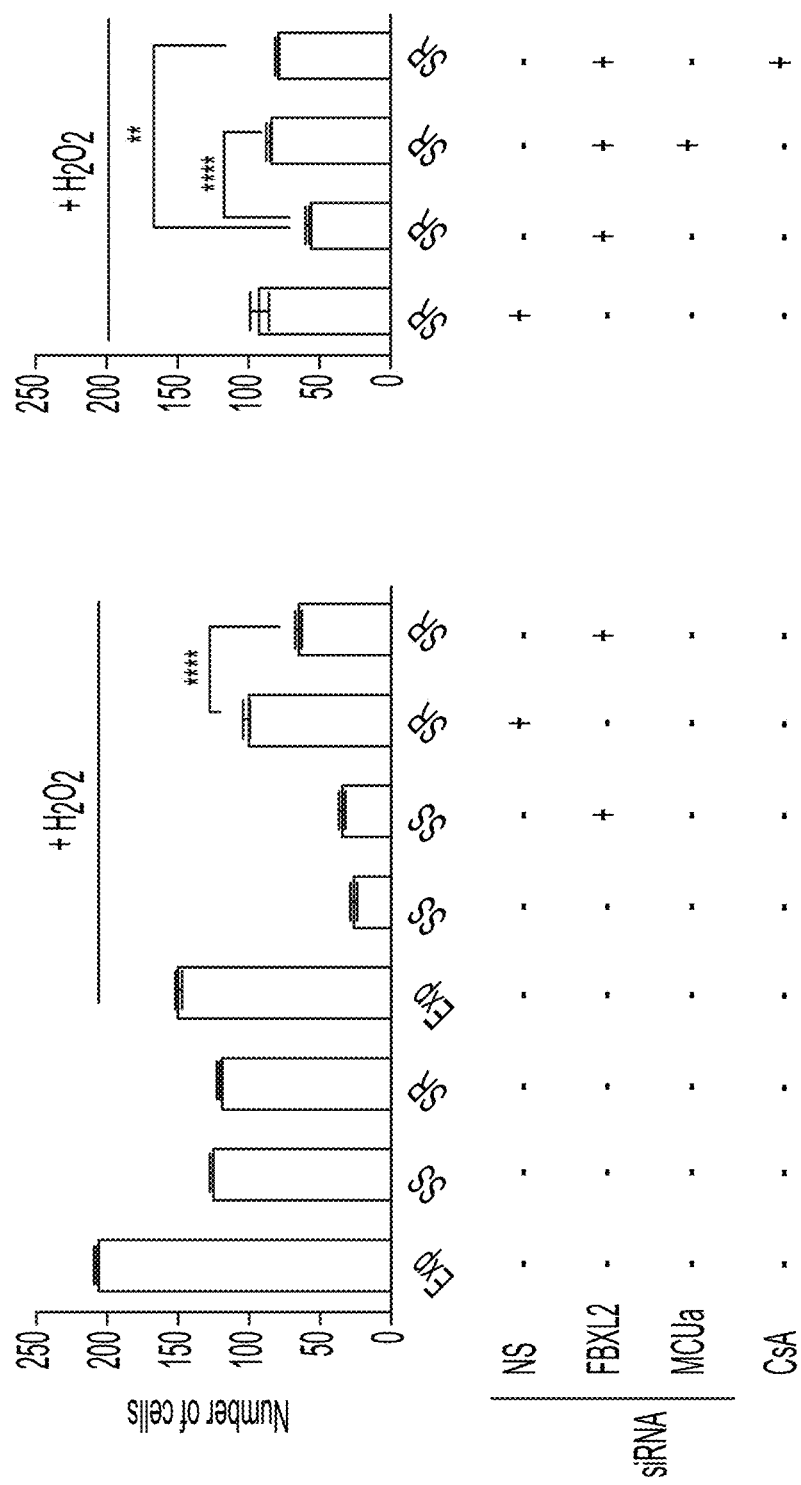
Figure 1E:
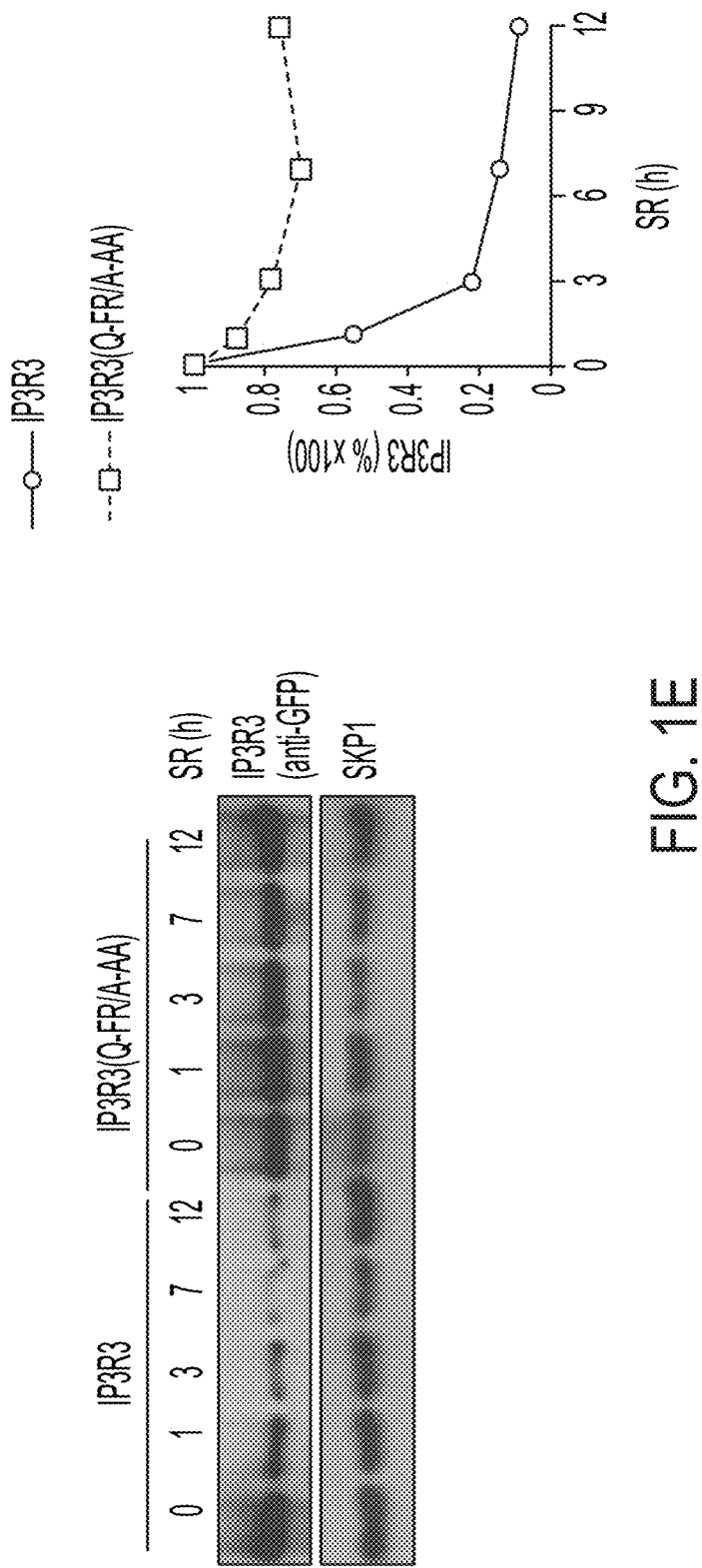

Serum starvation sensitized NHFs to treatment with H2O2, an oxidizing agent that induces persistent release of Ca2+ from the endoplasmic reticulum and consequent apoptosis, but serum re-addition alleviated this sensitivity (FIG. 1b). Compared to cells re-stimulated with serum, serum-starved cells displayed an increase in cleaved PARP, cleaved caspase-3, and cytochrome c release (FIG. 1c, d), all signatures of apoptosis. In cells re-stimulated with serum, FBXL2 knockdown caused IP3R3 accumulation, sensitization to H2O2, and an increase in the apoptotic signature and in mitochondrial Ca2+ uptake (FIG. 1b-d and Extended Data FIG. 3f). Conversely, expression of wild-type FBXL2, but not FBXL2(CaaX/SaaX), induced resistance to H2O2, but not to etoposide (Extended Data FIG. 3g). Inhibition of mitochondrial Ca2+ overload by silencing MCUA or preventing the PTP opening using cyclosporin-A abolished the sensitization to H2O2 by FBXL2 silencing (FIG. 1b).

Figure 4A:
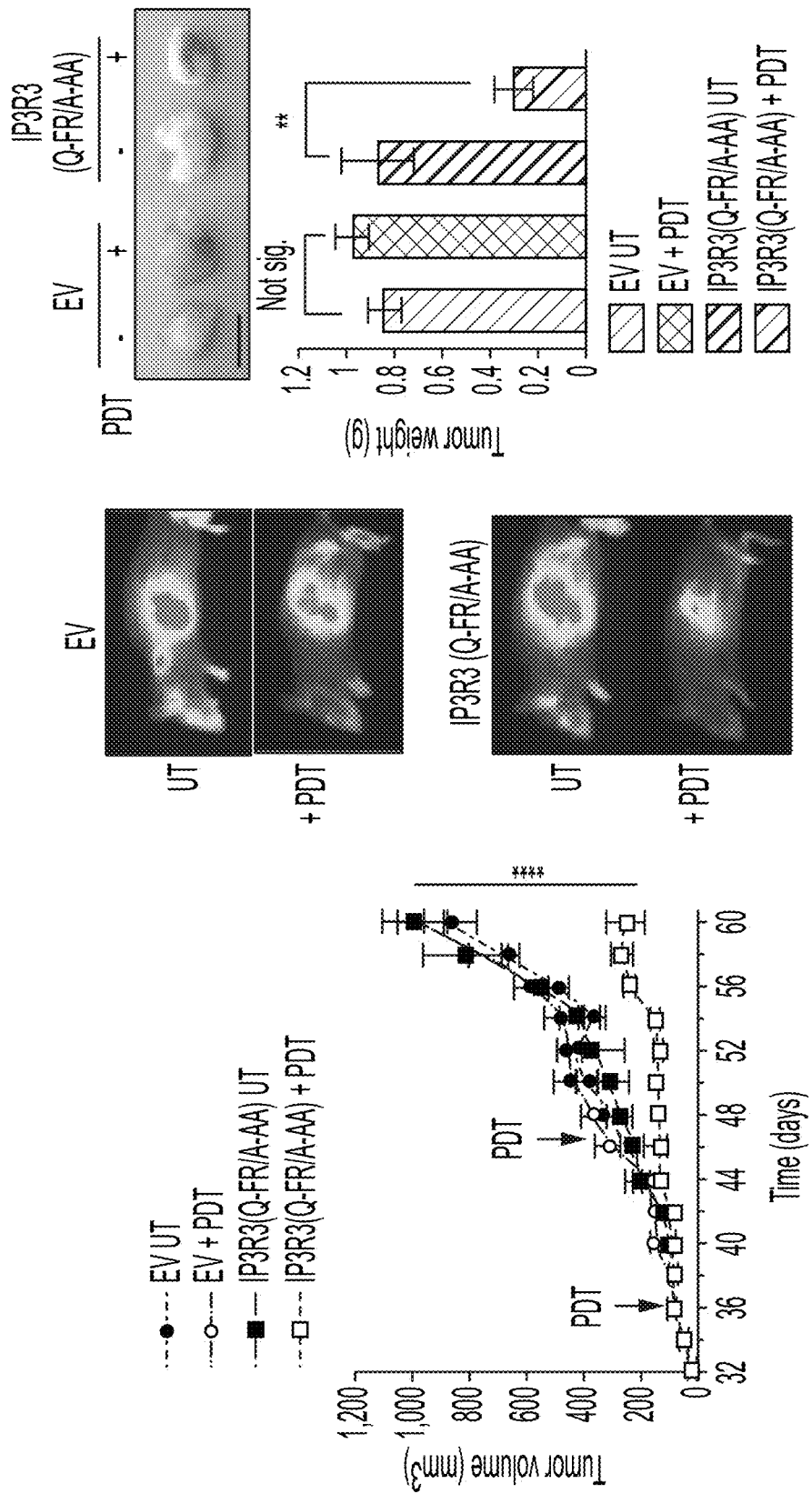
FIGS. 4A, 4B, 4C, and 4D show both a non-degradable IP3R3 mutant and GGTi-2418 sensitize tumours to PDT.

Next, we mapped the FBXL2 binding domain (that is, the degron) in IP3R3 and narrowed it to a region located between amino acids 436-587 (Extended Data FIG. 4a, b). Fragments encoding IP3R3(436-587) and IP3R3(227-602) interacted with FBXL2 more stably than IP3R3 (1-602), suggesting that the N-terminal suppressor domain of IP3R3 inhibits the FBXL2-IP3R3 interaction. Treatment of cells with ATP, which induces IP3 production and repositioning of the N-terminal suppressor domain', increased the binding between FBXL2 and IP3R3, particularly upon proteasome inhibition (Extended Data FIG. 4c, d). This suggests that once IP3 unmasks the IP3R3 degron, FBXL2 binds IP3R3 and this interaction is maintained, particularly if the degradation of IP3R3 is inhibited. Finally, ATP promoted the degradation of IP3R3 in cells cultured in the presence, but not in the absence, of serum (Extended Data FIG. 4e).

We then fine-mapped the degron to a region between amino acids 545 and 566 and found that Phe553 (which is highly conserved in IP3R3 orthologues, but not in its paralogues), and to a lesser extent Gln550 and Arg554, were necessary for efficient binding of IP3R3 to FBXL2 (Extended Data FIG. 4f-i). IP3R3(Q-FR/A-AA), a mutant in which Gln550, Phe553 and Arg554 were mutated to Ala, displayed a longer half-life than wild-type IP3R3, and it was not degraded when serum-starved cells were re-stimulated with serum (FIG. e, f). Expression of FBXL2 resulted in increased ubiquitination of IP3R3, but IP3R3(Q-FR/A-AA) remained poorly ubiquitinated (Extended Data FIG. 4j).

Figures 1F, 1G:
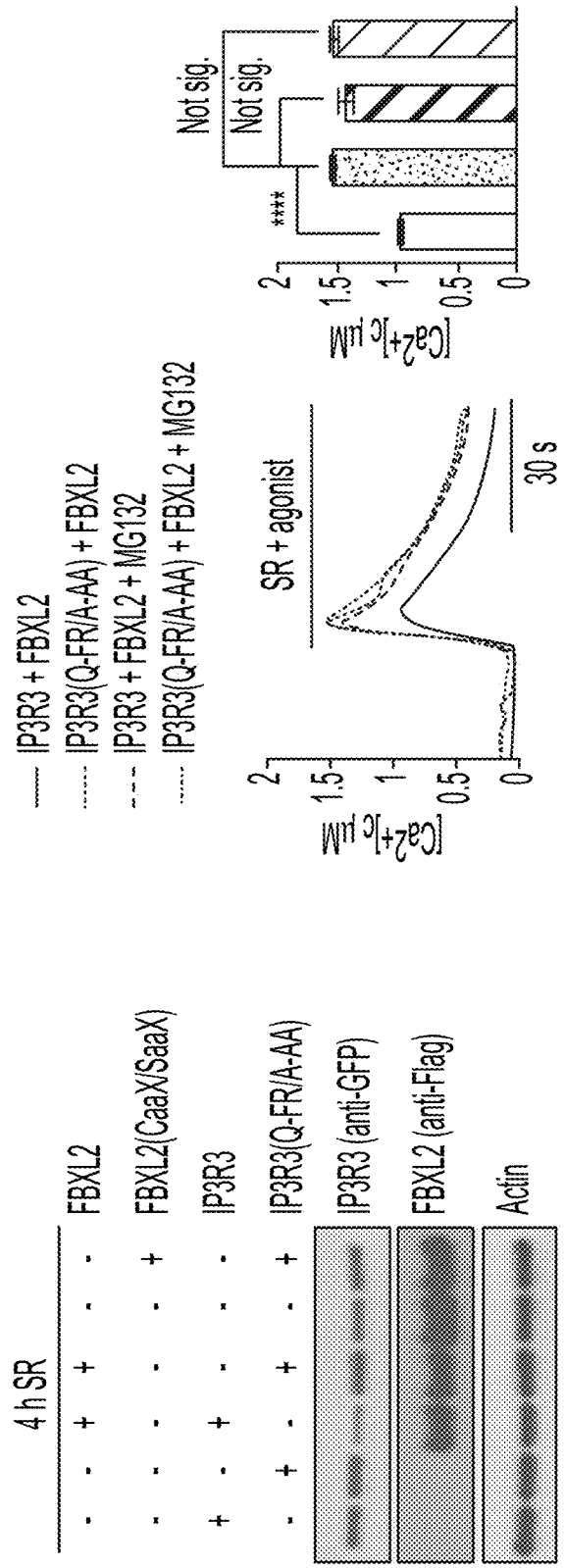

Importantly, expression of IP3R3(Q-1-R/A-AA) recapitulated the phenotypes observed upon FBXL2 silencing: enhanced Ca2+ release from the endoplasmic reticulum following serum treatment and agonist stimulation, and sensitization to H2O2 (FIG. 1g-i and Extended Data FIG. 3h, i). Moreover, in cells expressing IP3R3(Q-FR/A-AA), MG132 did not produce an increase of the Ca2+ response (FIG. 1g and Extended Data FIG. 3h).

Certain tumour suppressors and oncoproteins with roles in Ca2+ homeostasis localize to the endoplasmic reticulum (for example, AKT1, BCL2, p53, PML4, PTEN and KRAS4B)[12]. When these six proteins were expressed in HEK293T cells, PTEN was the only one able to robustly interact with endogenous IP3R3, and the interaction between PTEN and IP3R3 was confirmed at the endogenous level (Extended Data FIG. 5a-c). Compared to Pten+/+ mouse embryonic fibroblasts (MEFs)[13], the steady-state levels of IP3R3 were lower and its half-life was shorter in Pten−/− MEFs (Extended Data FIG. 5d, e). Importantly, in response to mitogens, IP3R3 was degraded faster in Pten−/− than in Pten+/+ MEFs, and this phenotype was reverted by silencing FBXL2 (FIG. 2a). Finally, after serum re-addition, IP3R3 was ubiquitinated to a greater extent in Pten−/− than in Pten+/+ MEFs (Extended Data FIG. 5f).

Figures 5H, 5I:
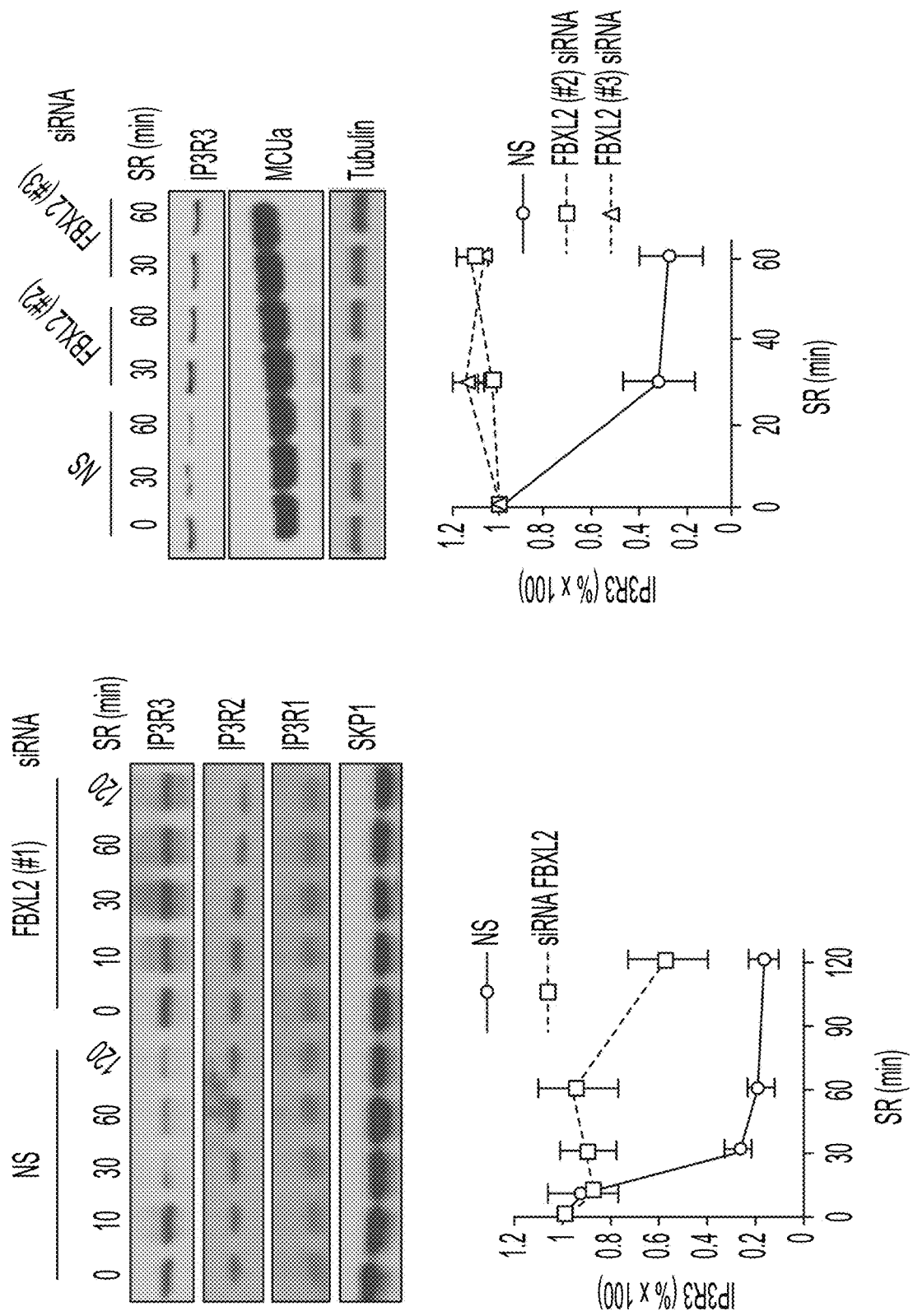
Figure 5J:
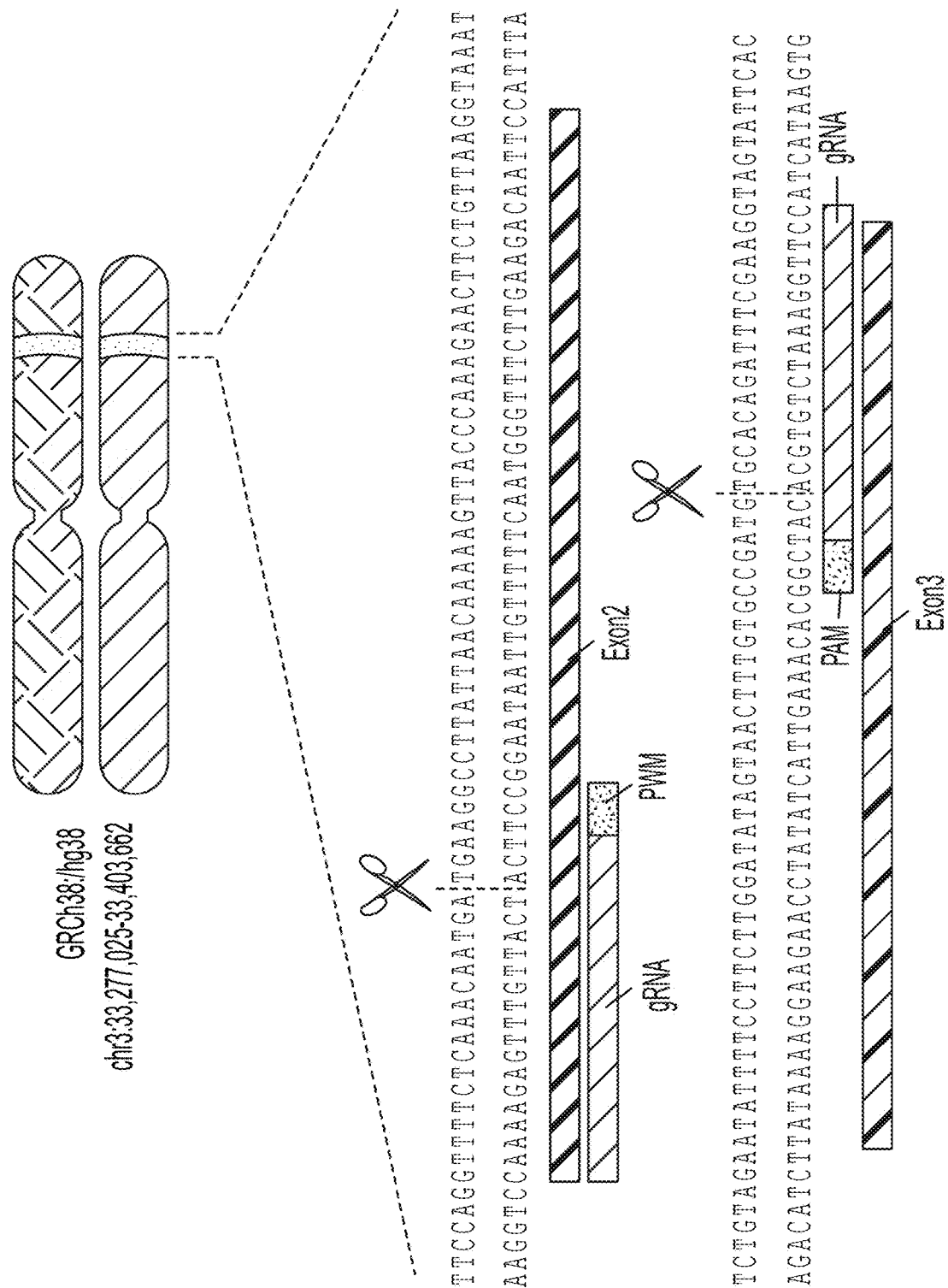
Figure 5K:
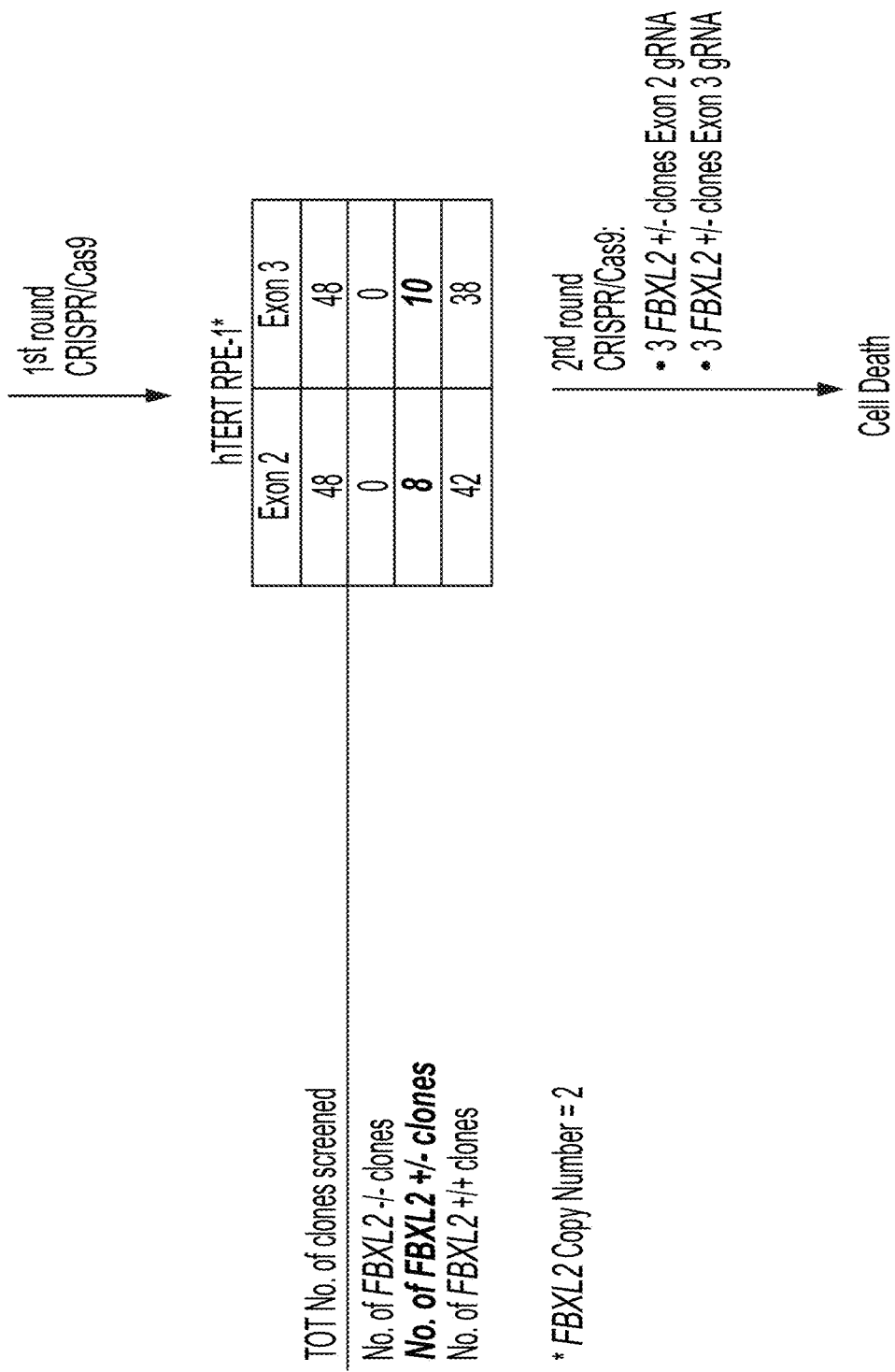
Figure 5L:
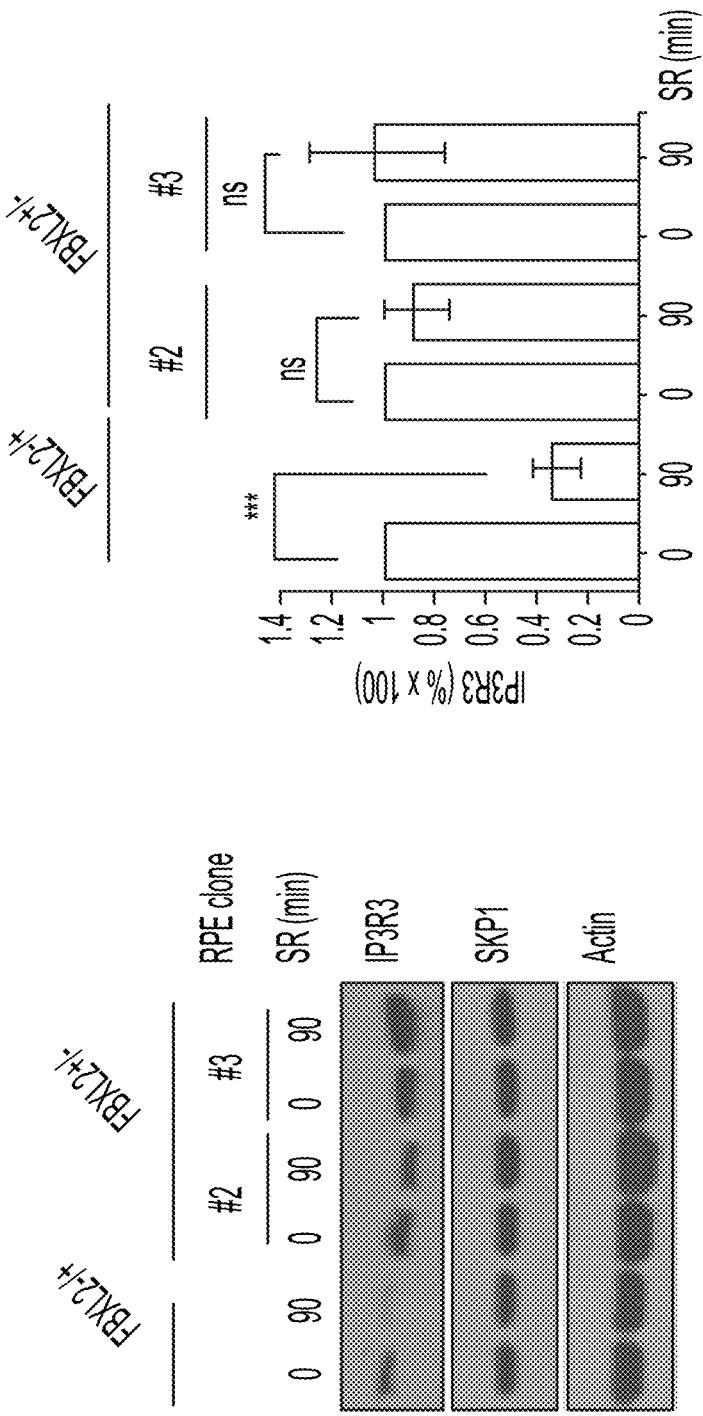

PTEN reconstitution in Pten−/− MEFs and cell lines expressing no or low levels of PTEN induced an increase in the levels of IP3R3 (FIG. 2b and Extended Data FIG. 5g). PTEN(C124S), a catalytically dead mutant[4], was also able to enhance IP3R3 levels and induce apoptotic cleavage of caspase-3, although not as efficiently as wild-type PTEN, (FIG. 2b and Extended Data FIG. 5g). Silencing of IP3R3 counteracted the apoptotic cleavage of caspase-3 induced by PTEN(C124S) (FIG. 2b). Expression of wild-type PTEN or, to a lesser extent, PTEN(C124S) in Pten−/− MEFs augmented Ca2+ mobilization from the endoplasmic reticulum in an IP3R3-dependent manner (FIG. 2c and Extended Data FIG. 5h). PTEN(G129E), a mutant displaying a greatly reduced lipid phosphatase activity, but retaining protein phosphatase activity4, induced an increase in the Ca2+ response identical to that induced by wild-type PTEN (FIG. 2c and Extended Data FIG. 5h). Finally, PTEN, PTEN (C124S) and PTEN(G129E) bound comparable amounts of IP3R3 (Extended Data FIG. 5i).

Figure 6A:
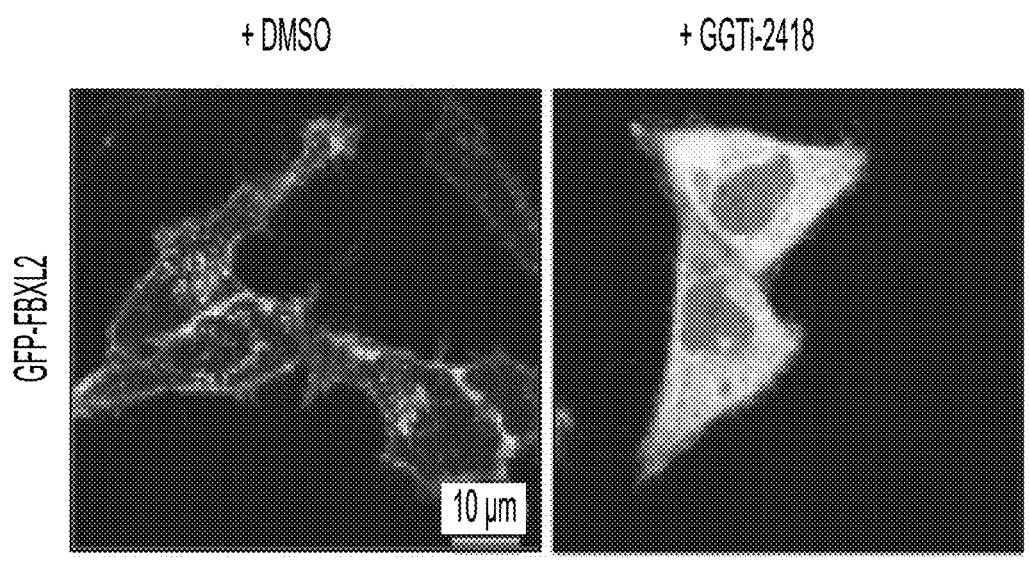
Figure 6B:
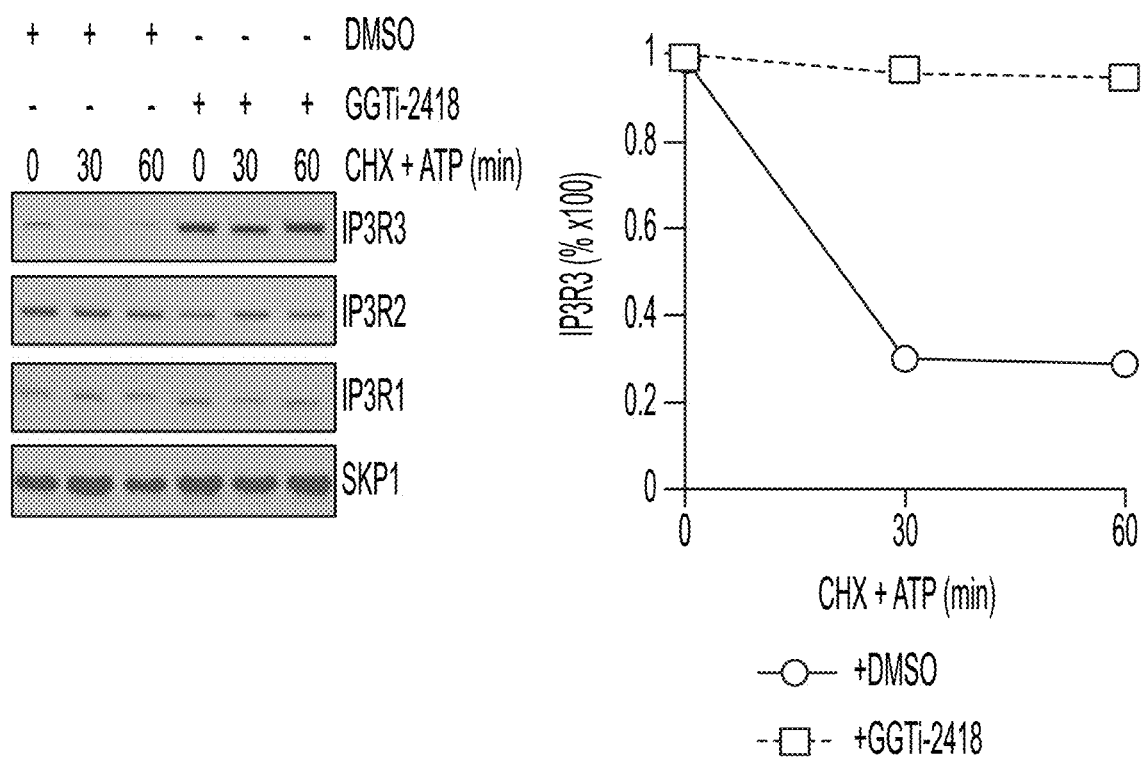
Figure 6C:
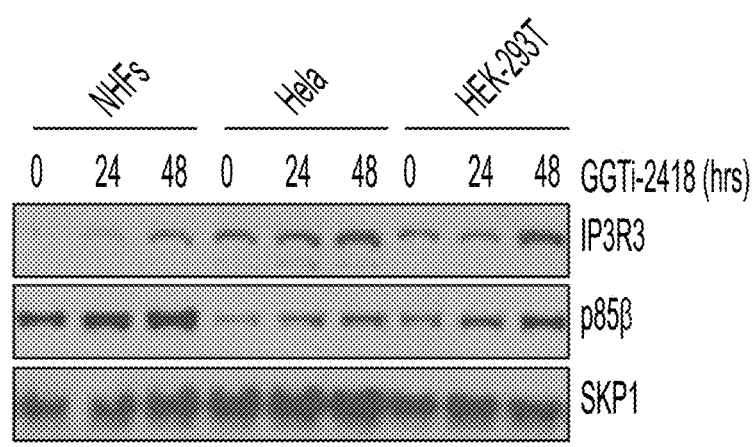
Figure 6F:
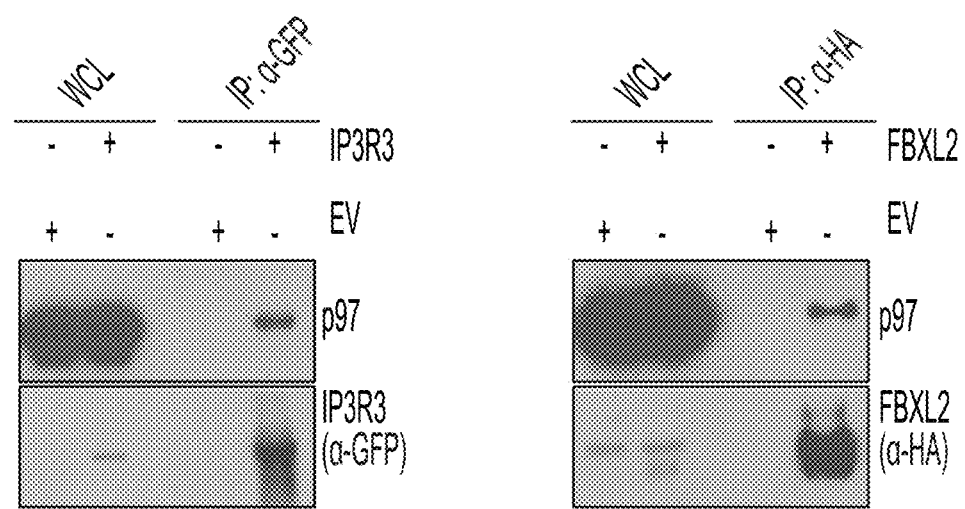

Like FBXL2, PTEN interacted more stably with IP3R3 (436-587) and IP3R3(Q-FR/A-AA), which is impaired in its binding to FBXL2, also interacted less with PTEN (Extended Data FIG. 6a, b), suggesting that PTEN and FBXL2 compete for the same region in IP3R3. Indeed, increasing amounts of FBXL2 interfered with the binding between PTEN and IP3R3, and increasing amounts of PTEN interfered with the binding between FBXL2 and IP3R3 (Extended Data FIG. 6c-e). Conversely, PTEN silencing, in addition to reducing IP3R3 levels, resulted in an increased interaction between IP3R3 and FBXL2 (Extended Data FIG. 6f).

Figure 6G:
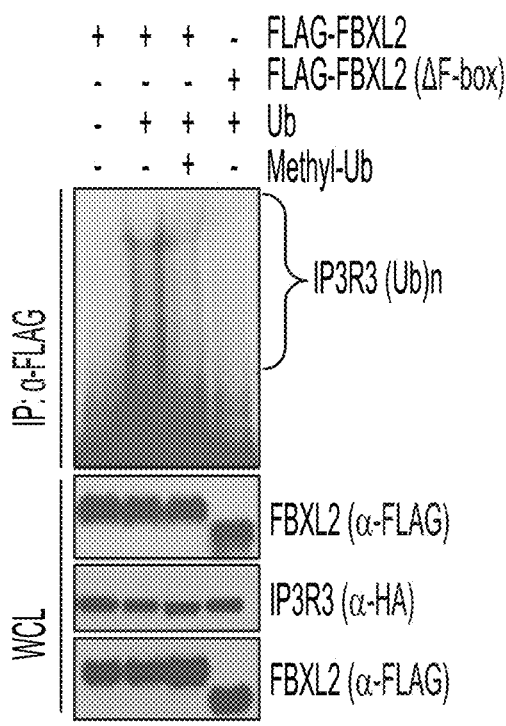
Figure 6H:
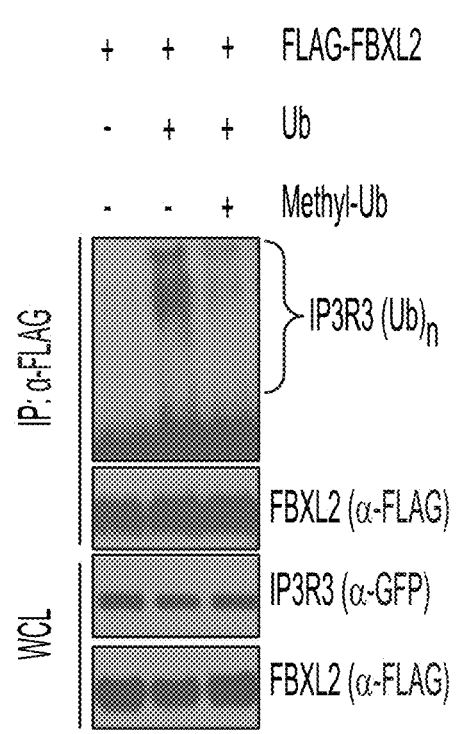

Compared to cells expressing PTEN, IP3R3 levels were significantly lower in cell lines expressing no or low levels of PTEN, although all cell lines expressed similar levels of FBXL2 mRNA (Extended Data FIG. 6g, h). The half-life of IP3R3 was significantly shorter in A549 cells compared to H460 (the former expressing low PTEN levels), and IP3R3 levels increased in U87 and A549 cells after reconstitution of PTEN expression or upon FBXL2 inhibition by GGTi-2418 (Extended Data FIGS. 5g and 6i, j). We also assessed the expression of PTEN and IP3R3 in tissue microarrays generated from human prostate adenocarcinomas and found that there was a significant, direct correlation between IP3R3 and PTEN expression levels (FIG. 2d and Extended Data FIG. 6k).

Figure 7A:
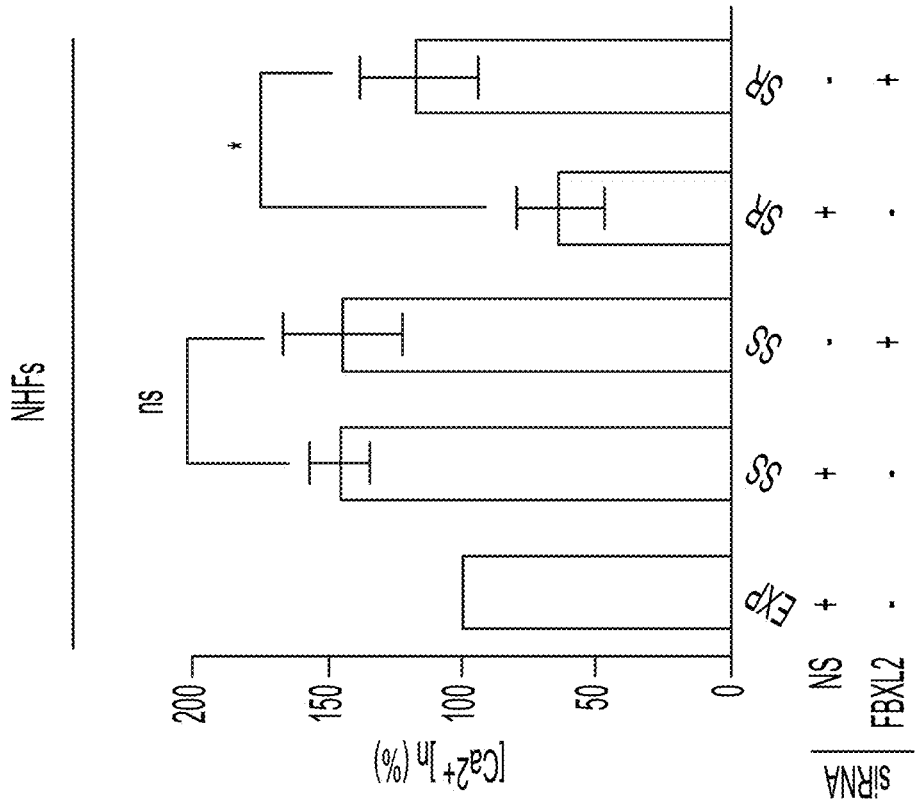
FIGS. 7A, 7B, 7C, 7D, 7E, 7F, 7G, 7H, and 7I show FBXL2 controls Ca2+ mobilization and Ca2+-mediated apoptosis.
Figure 7B:
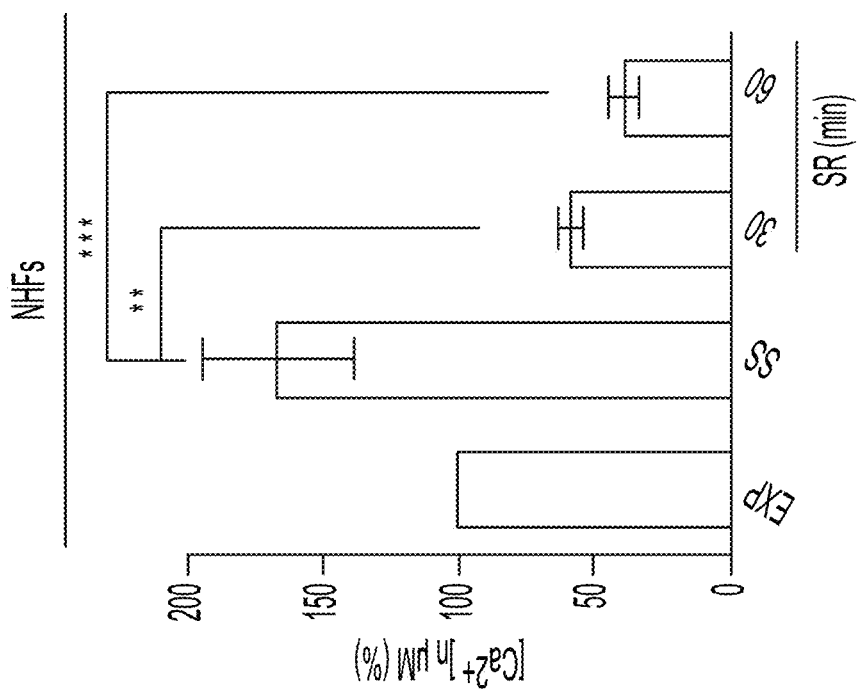
Figure 7C:
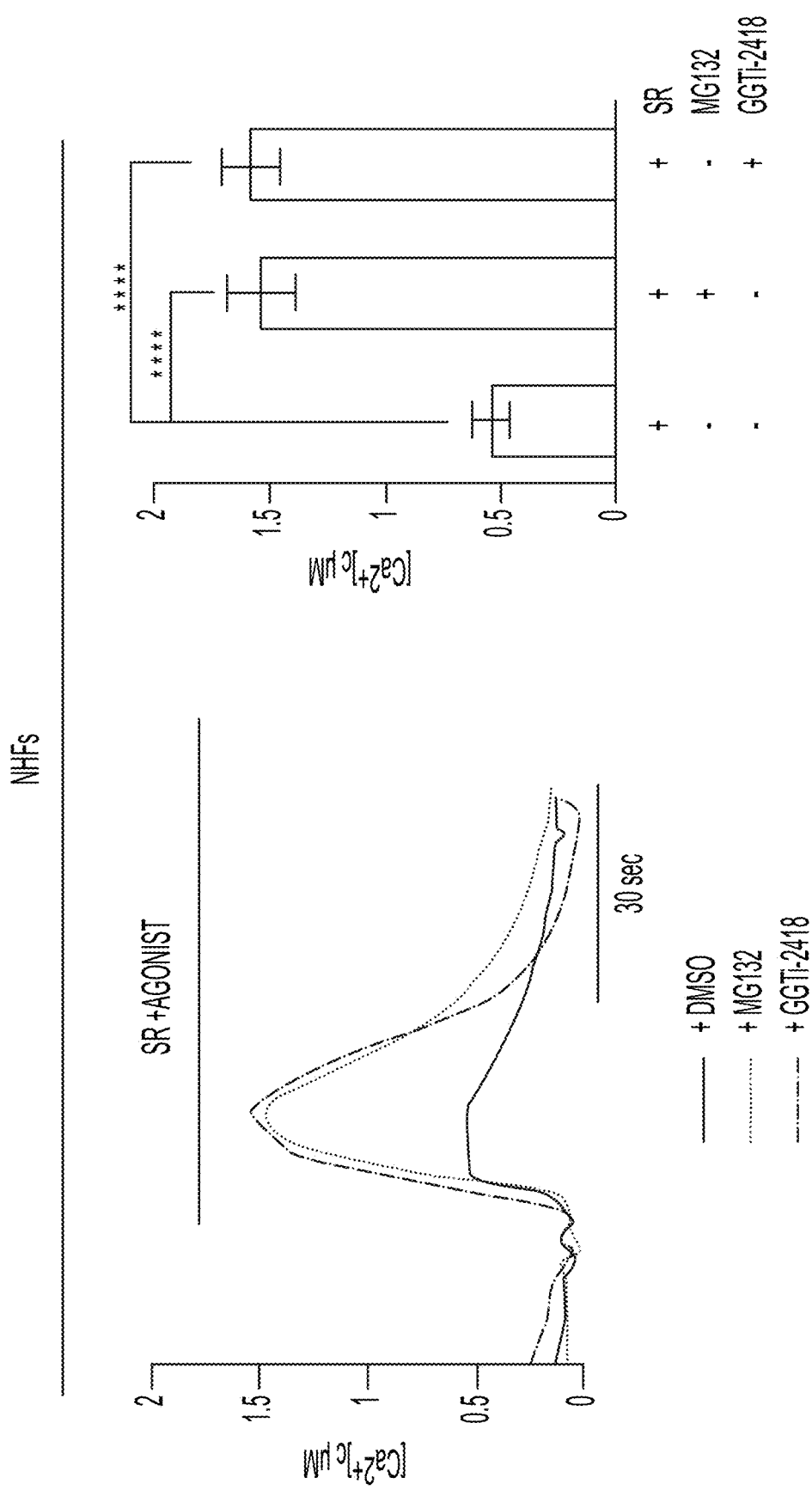
Figure 7D:
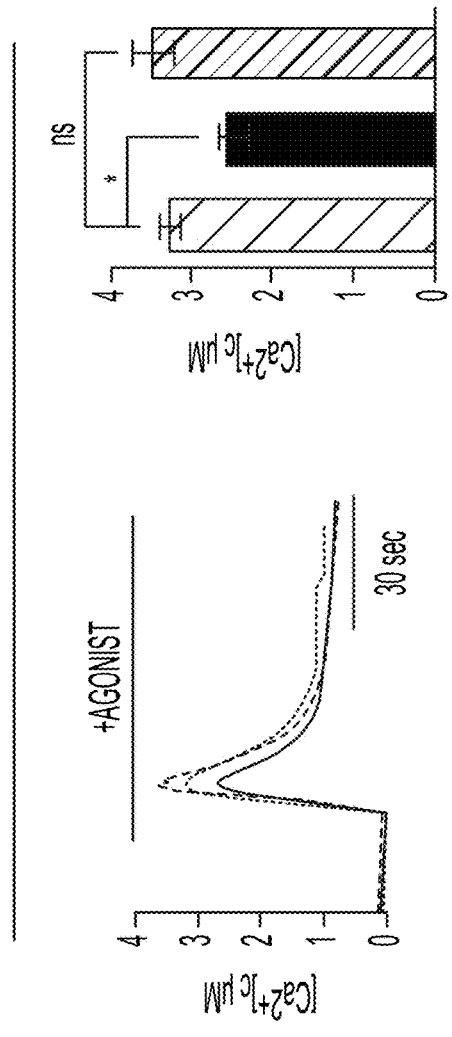
Figure 7E:
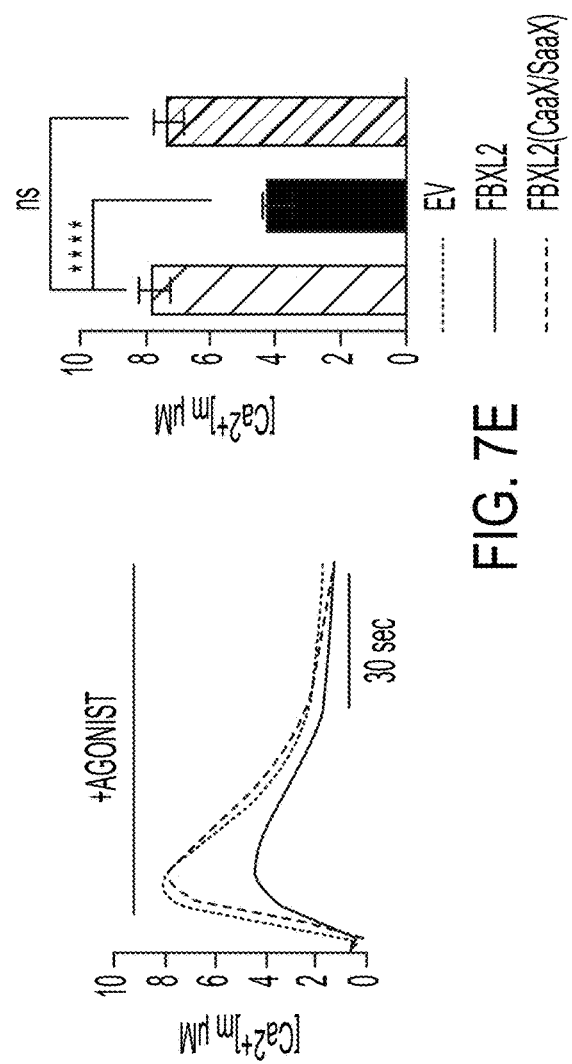
Figure 7F:
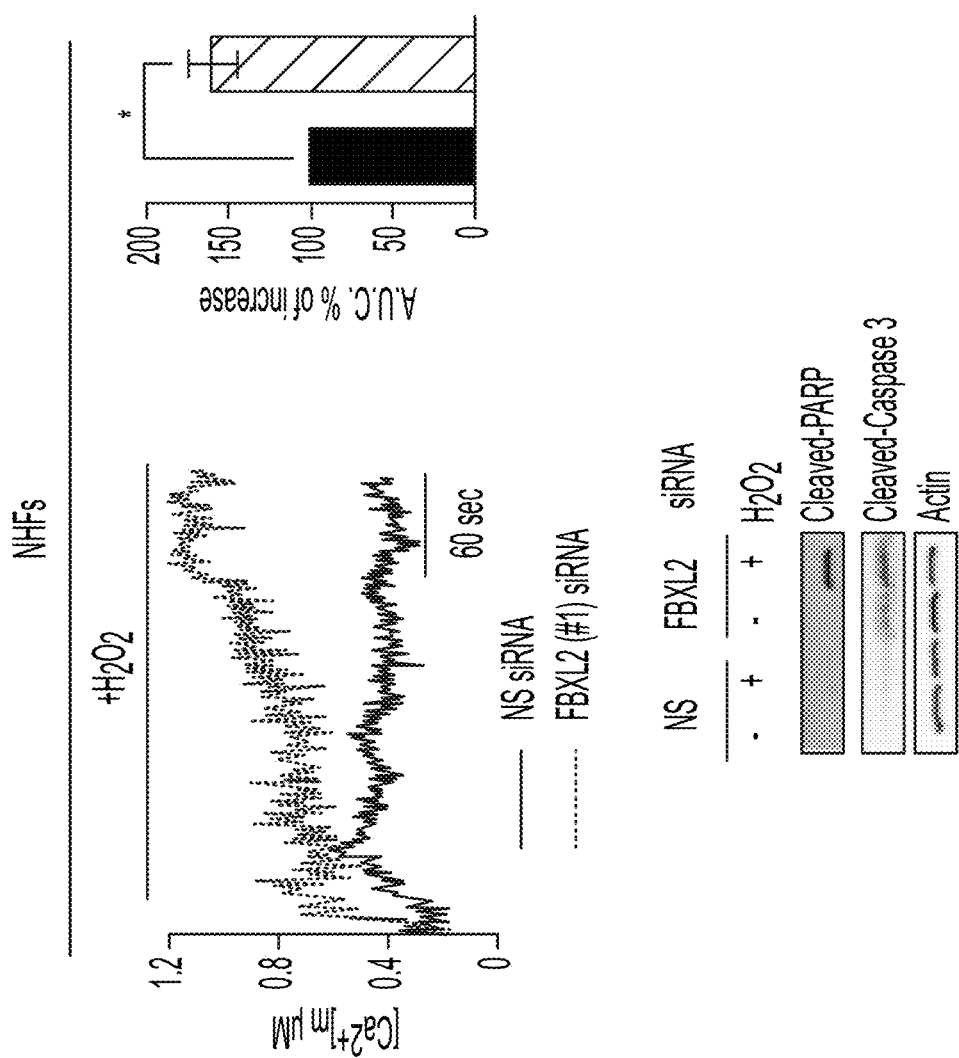
Figure 7G:
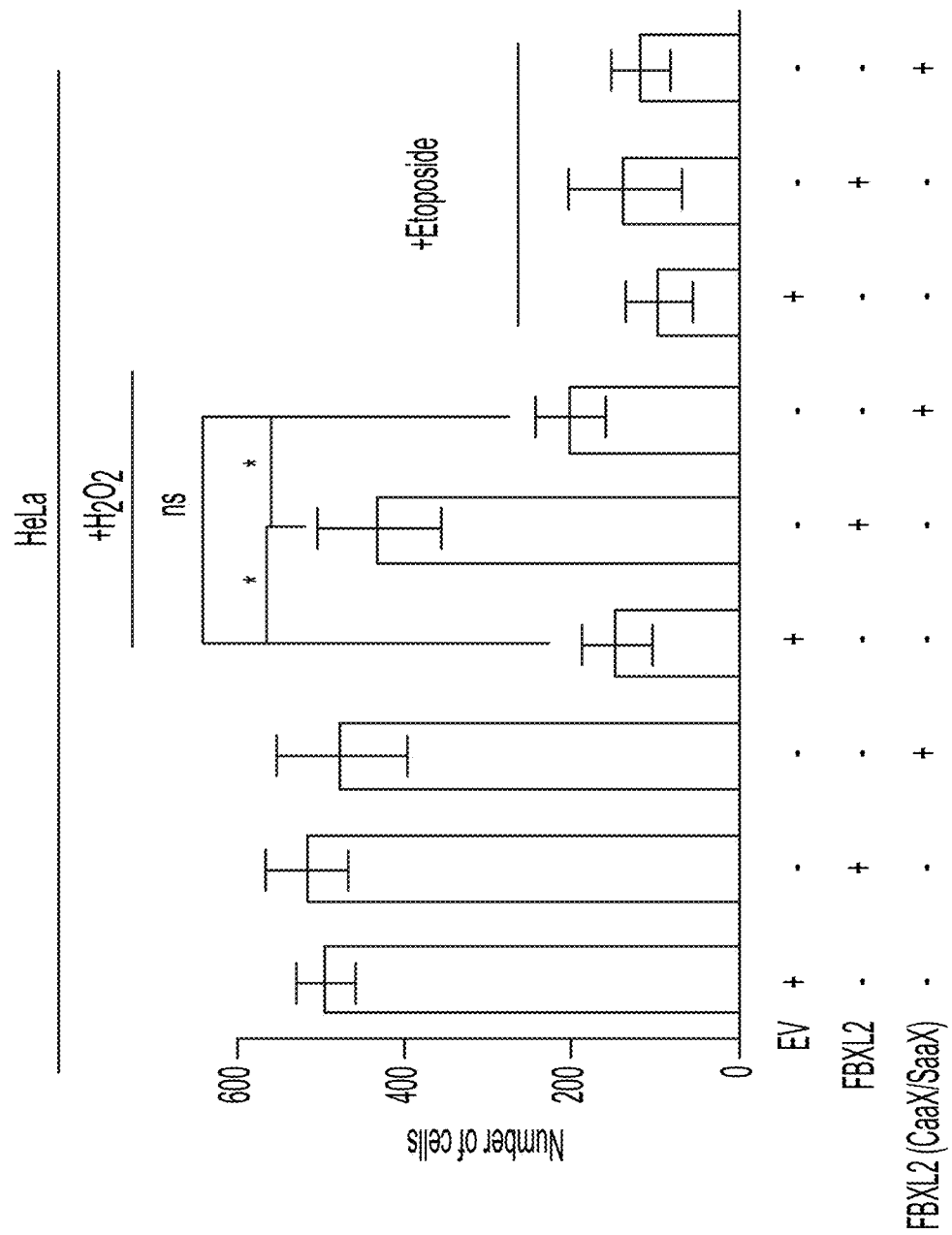
Figure 7H:
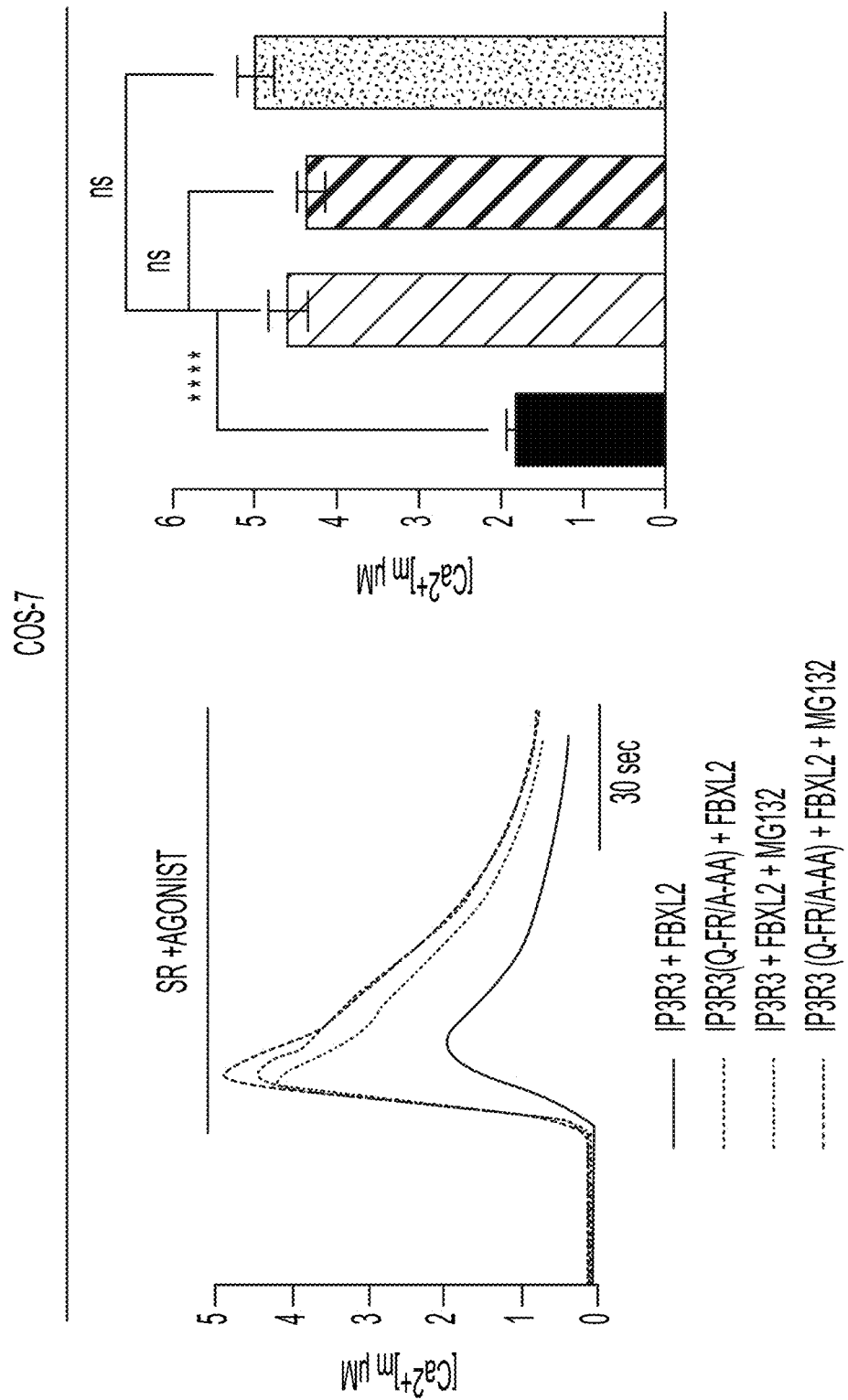
Figure 7I:
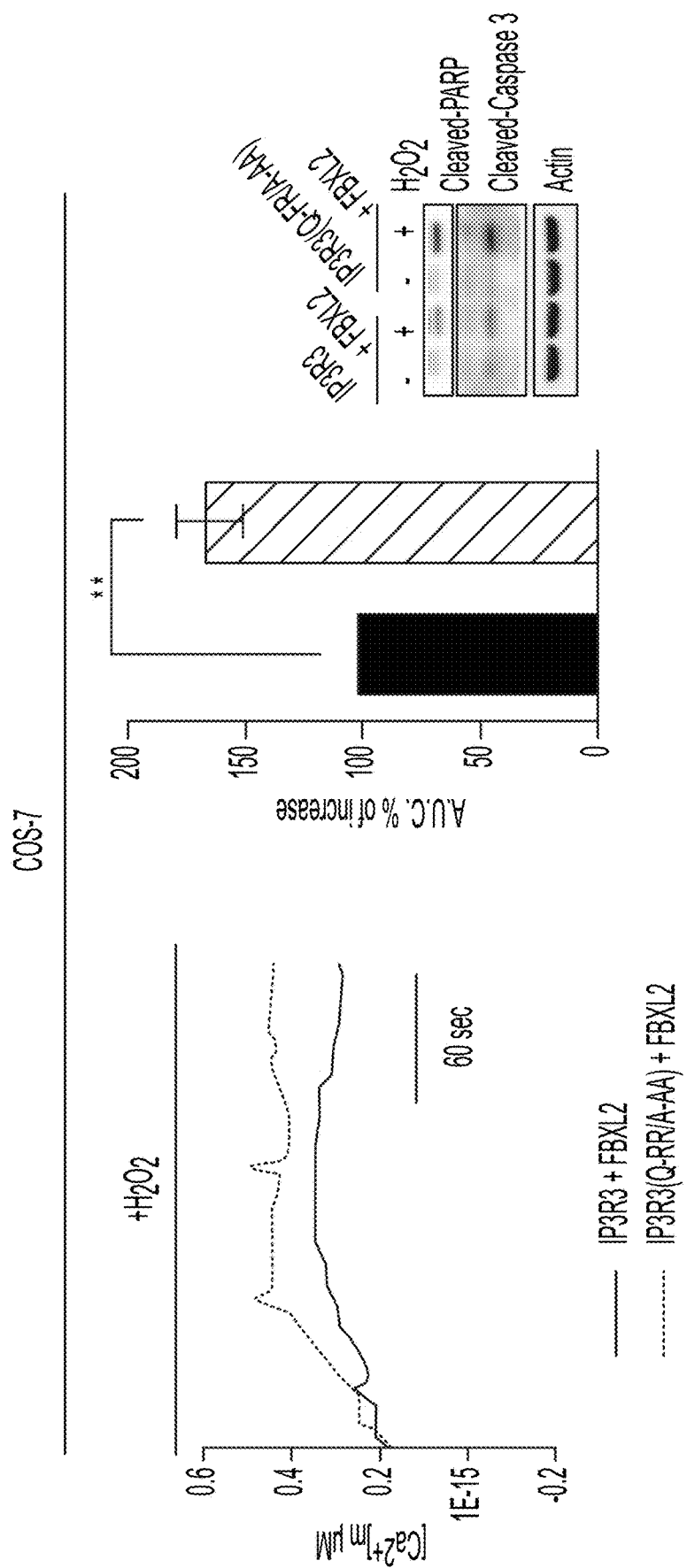
Figure 8A:
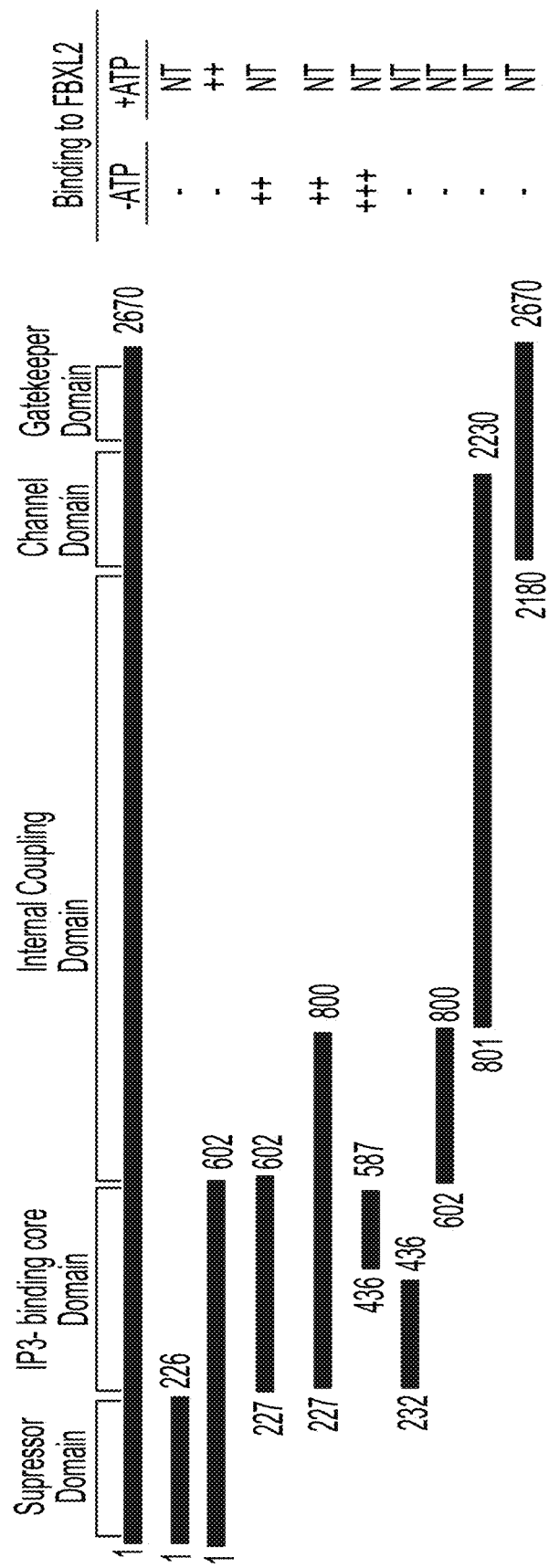
Figure 8B:
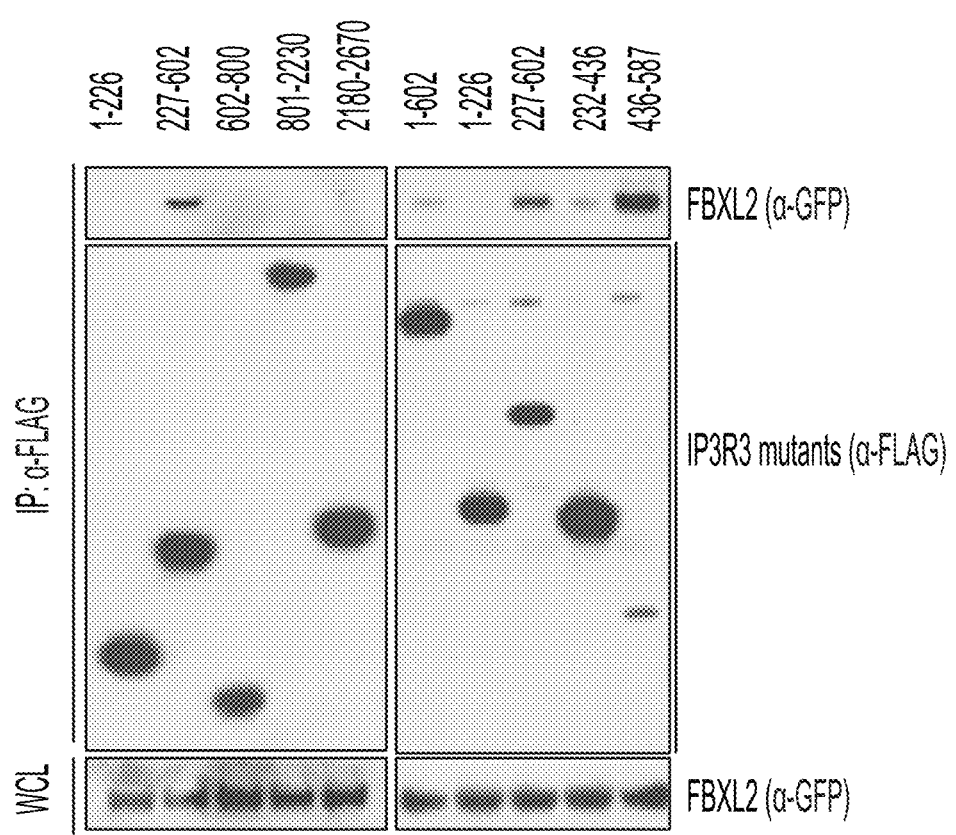
Figures 8C, 8D:
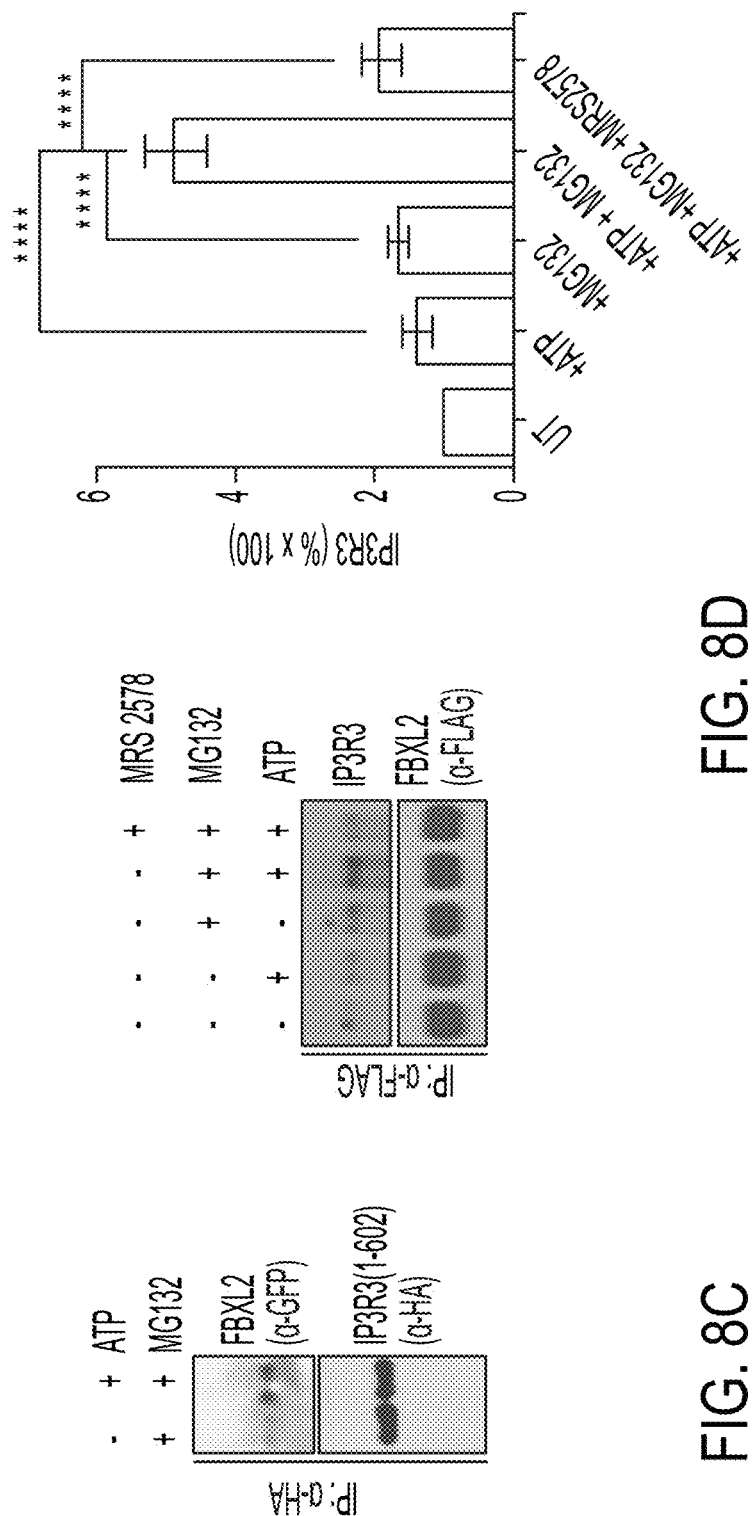
Figure 8E:
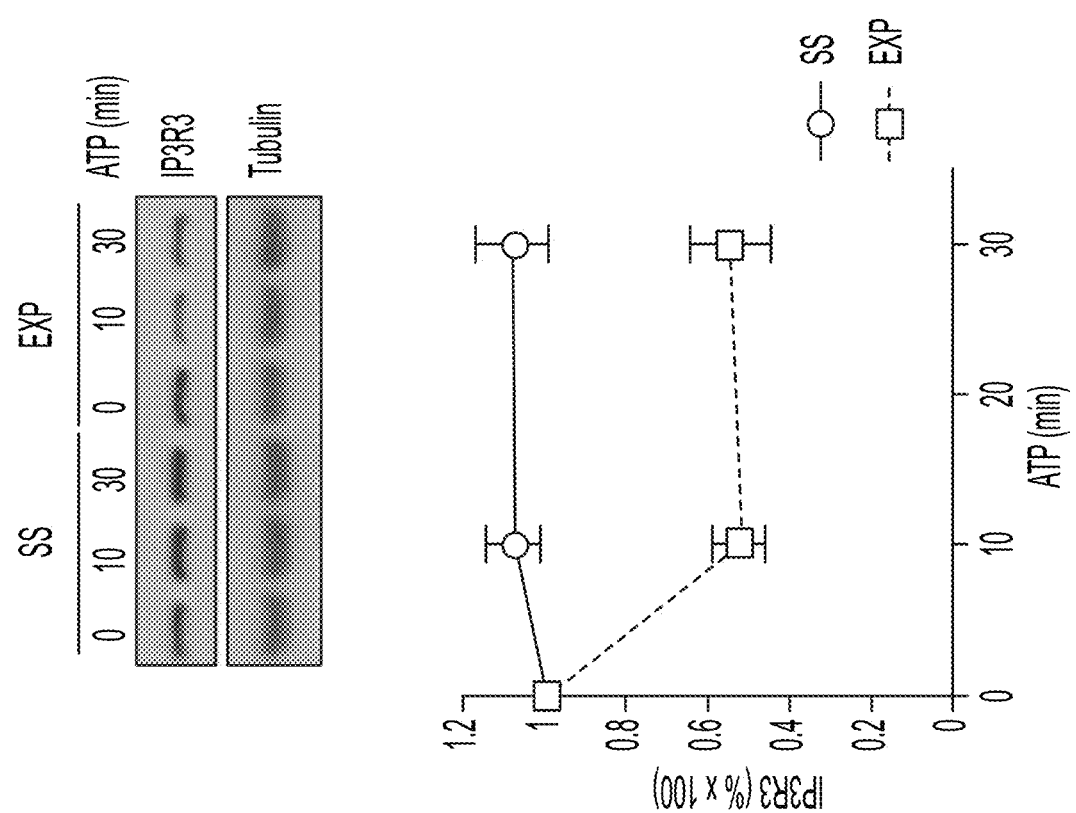
Figure 8G:
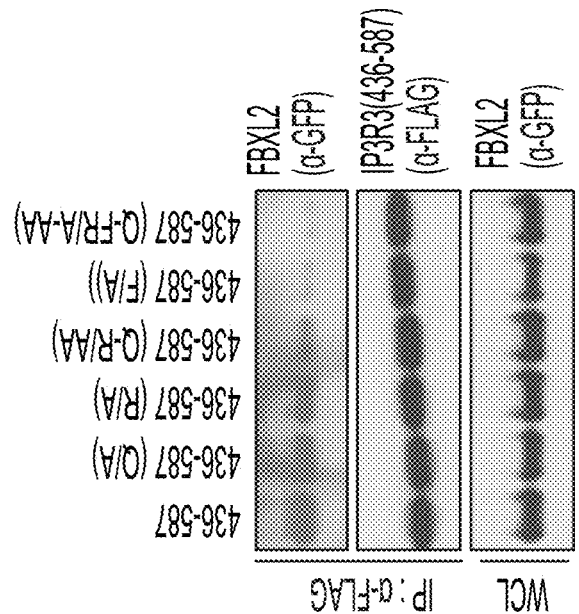
Figure 8F:
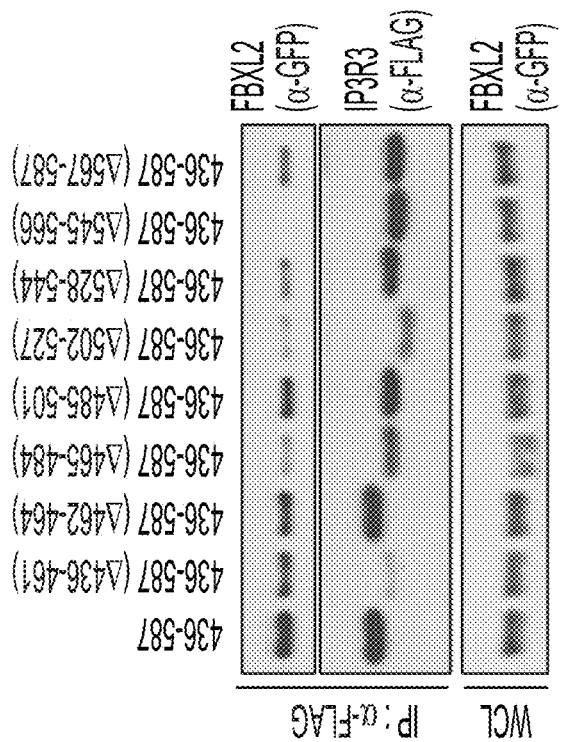
Figure 8J:
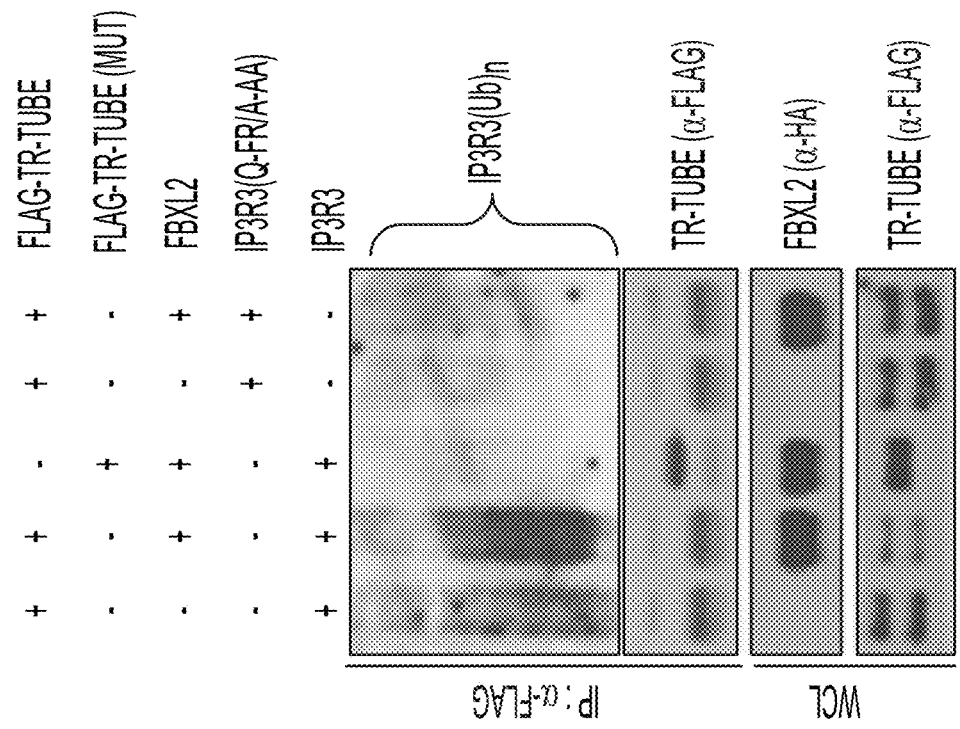
Figure 9A:
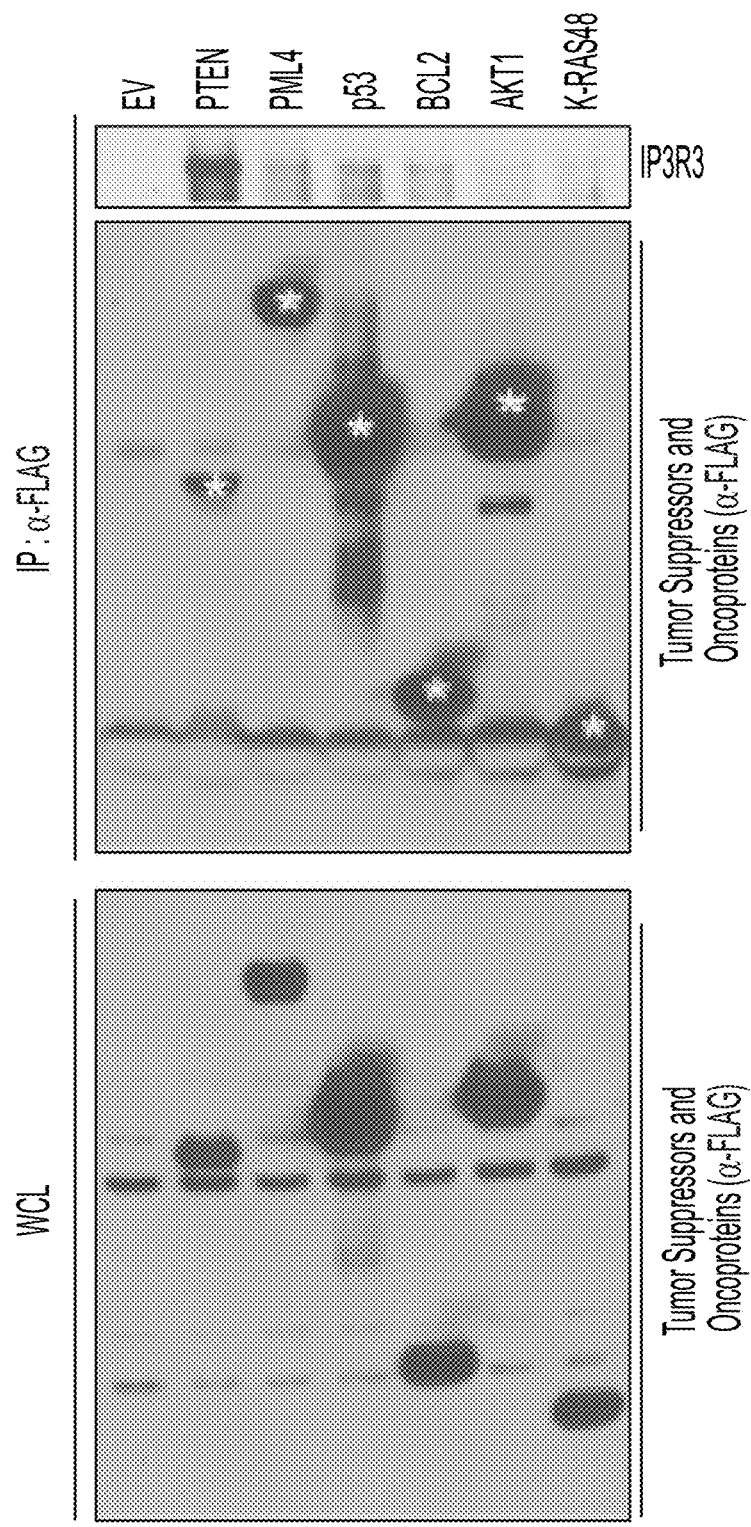
FIGS. 9A, 9B, 9C, 9D, 9E, 9F, 9G, 9H, and 9I show IP3R3 degradation is prevented by PTEN, independently of its phosphatase activity.
Figure 9B:
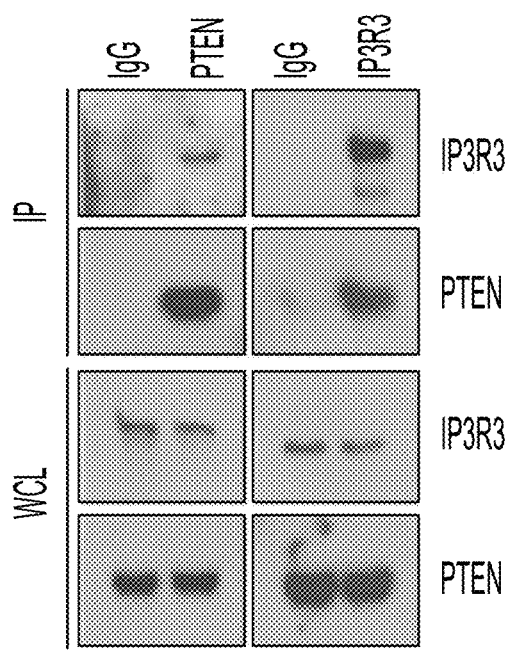
Figure 9C:
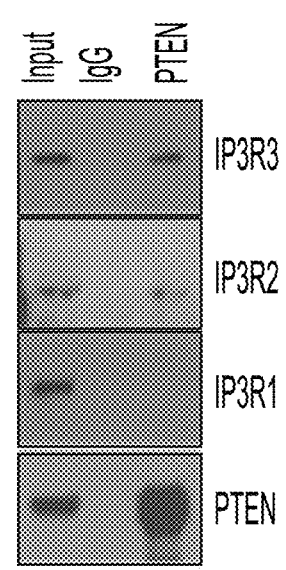
Figure 9D:
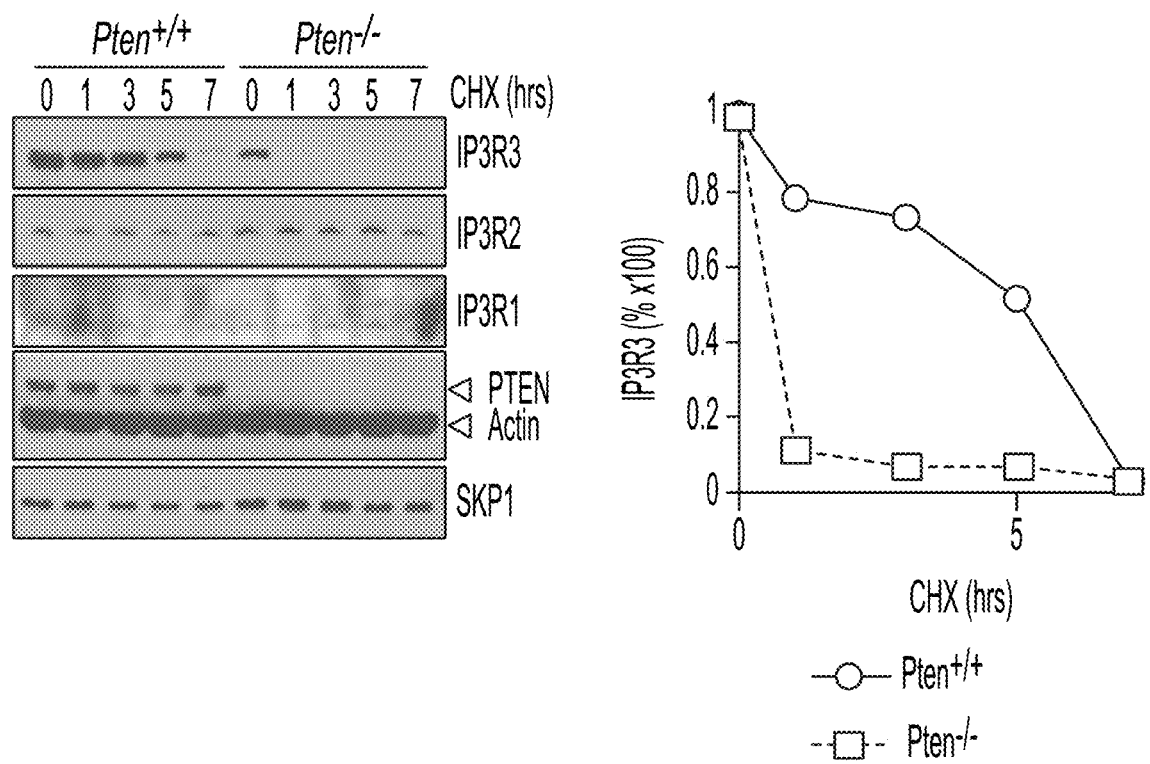
Figure 9E:
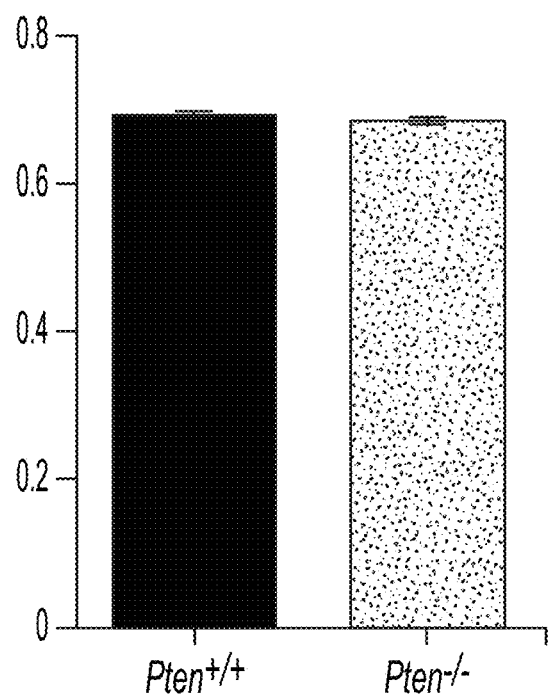
Figure 9F:
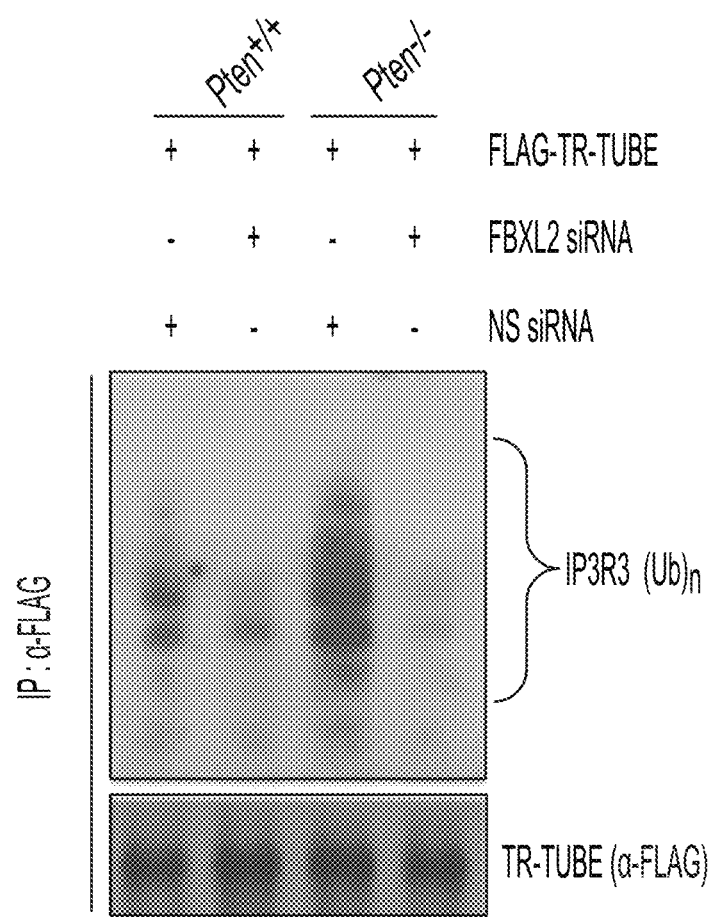
Figure 9G:
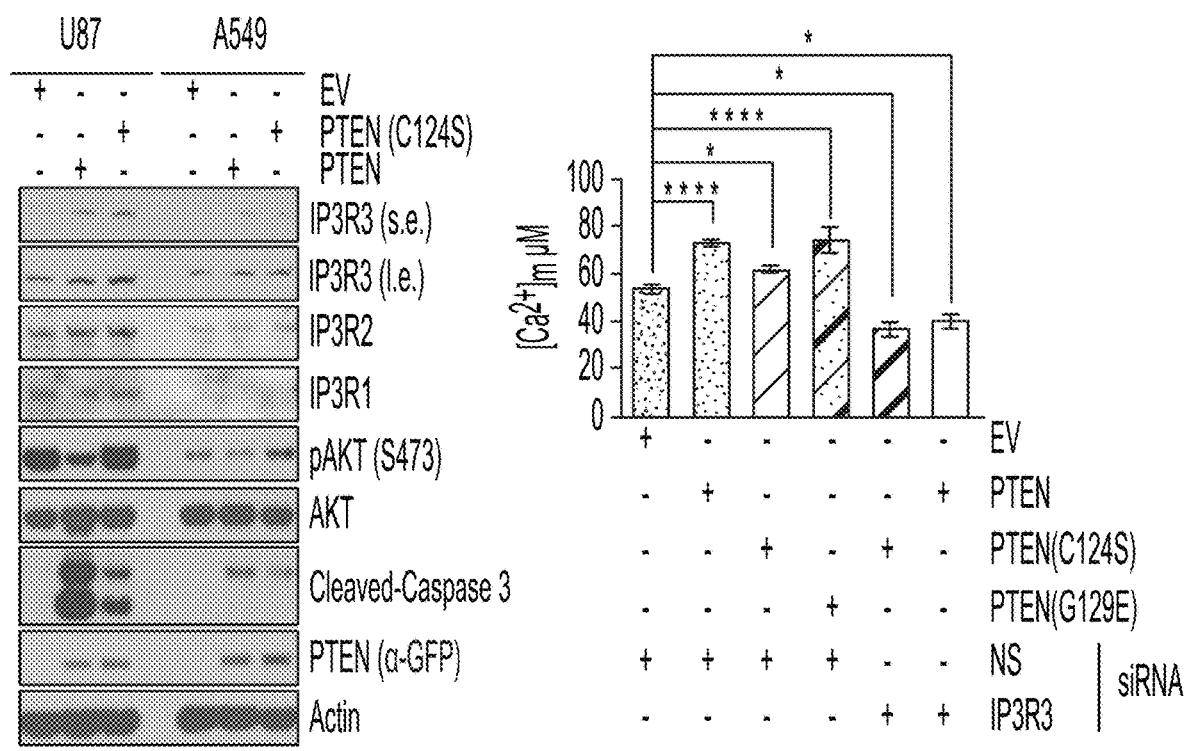
Figure 9H:
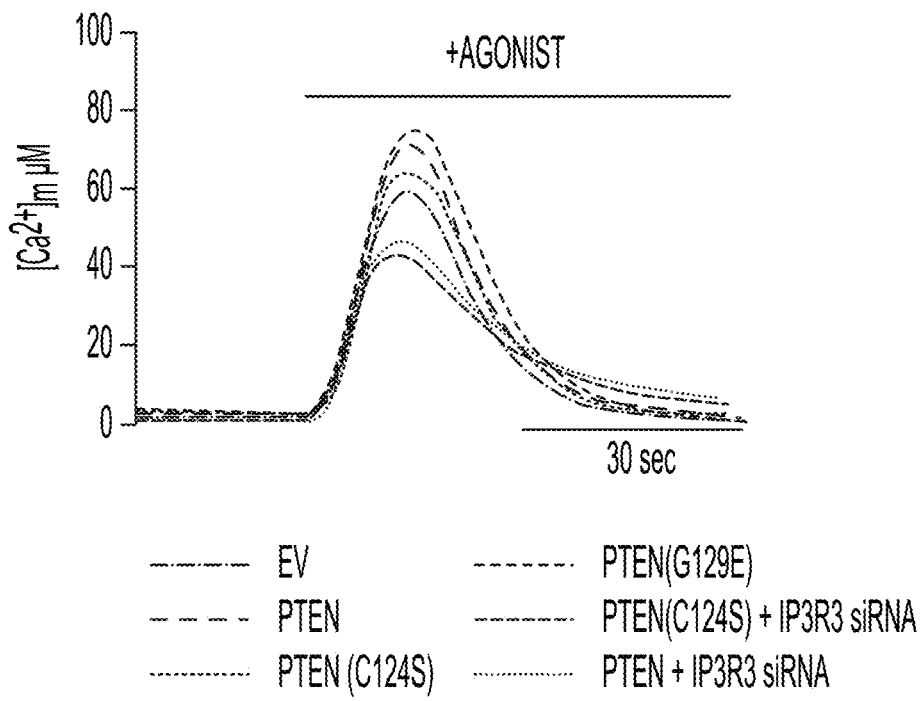
Figure 9I:
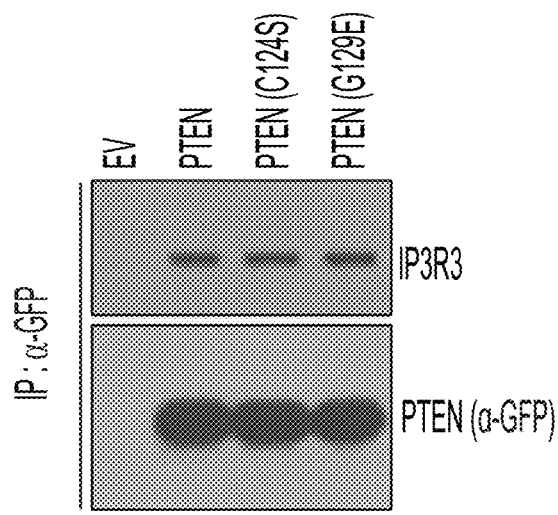

PDT-induced Ca2+ mobilization was significantly reduced when PTEN or IP3R3 were depleted, and, compared to cell lines expressing PTEN and high levels of IP3R3, cancer cell lines expressing no or low levels of PTEN and low levels of IP3R3 displayed less Ca2+ mobilization and less apoptotic markers upon photodynamic therapy (PDT) treatment (Extended Data FIG. 7a, b). Re-expression of either wild-type PTEN or PTEN(C124S) increased PDT-induced Ca2+ mobilization and apoptotic cleavage of caspase-3 and PARP (Extended Data FIG. 7c, d). Depletion of FBXL2 resulted in increased PDT-induced Ca2+ mobilization and apoptosis in cells with no or low levels of PTEN, which depended on the presence of IP3R3 (FIG. 3a and Extended Data FIG. 8a). Similarly, expression of IP3R3(Q-FR/A-AA) increased PDT-induced Ca2+ mobilization and apoptosis (Extended Data FIG. 8b). We also generated A549 and PC3 knock-in clones expressing IP3R3 (Q-FR/A-AA) (Extended Data FIG. 9a-c). Compared to parental cells, these clones displayed the stabilization of IP3R3, released more Ca2+ from the endoplasmic reticulum, and were more prone to apoptosis when treated with PDT (FIG. 3b and Extended Data FIG. 9d-g).

Figure 4B:
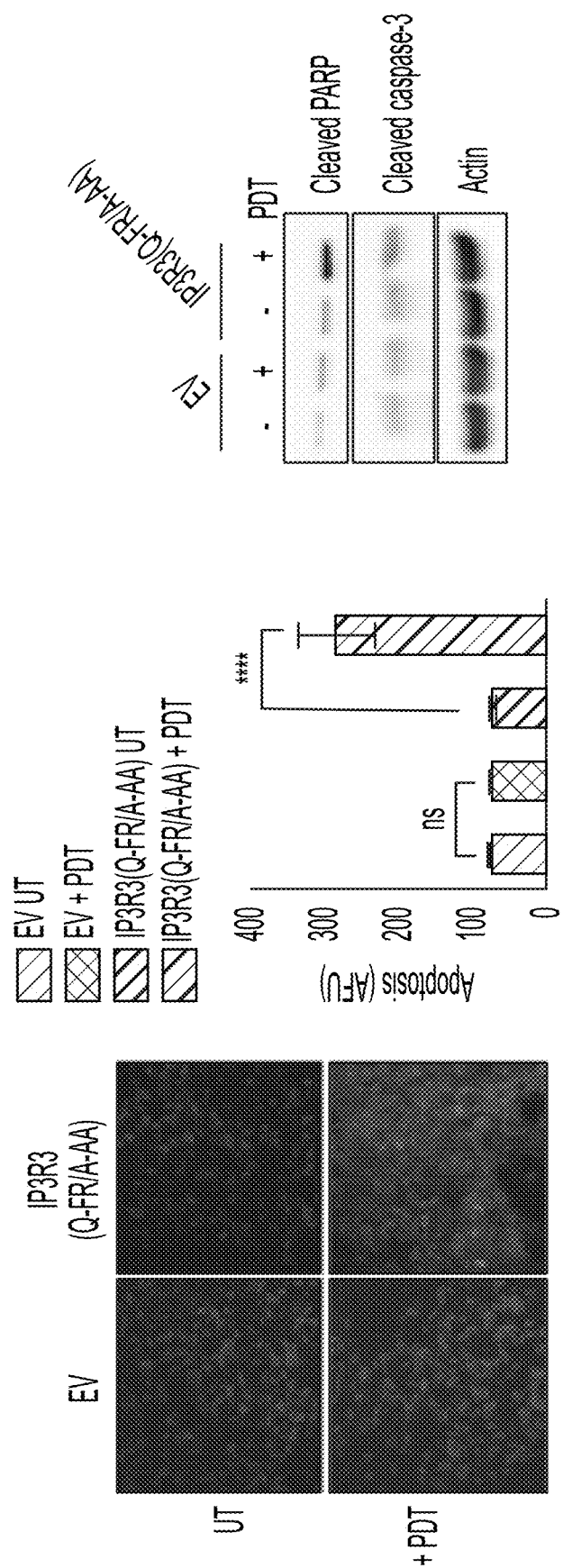
Figure 10A:
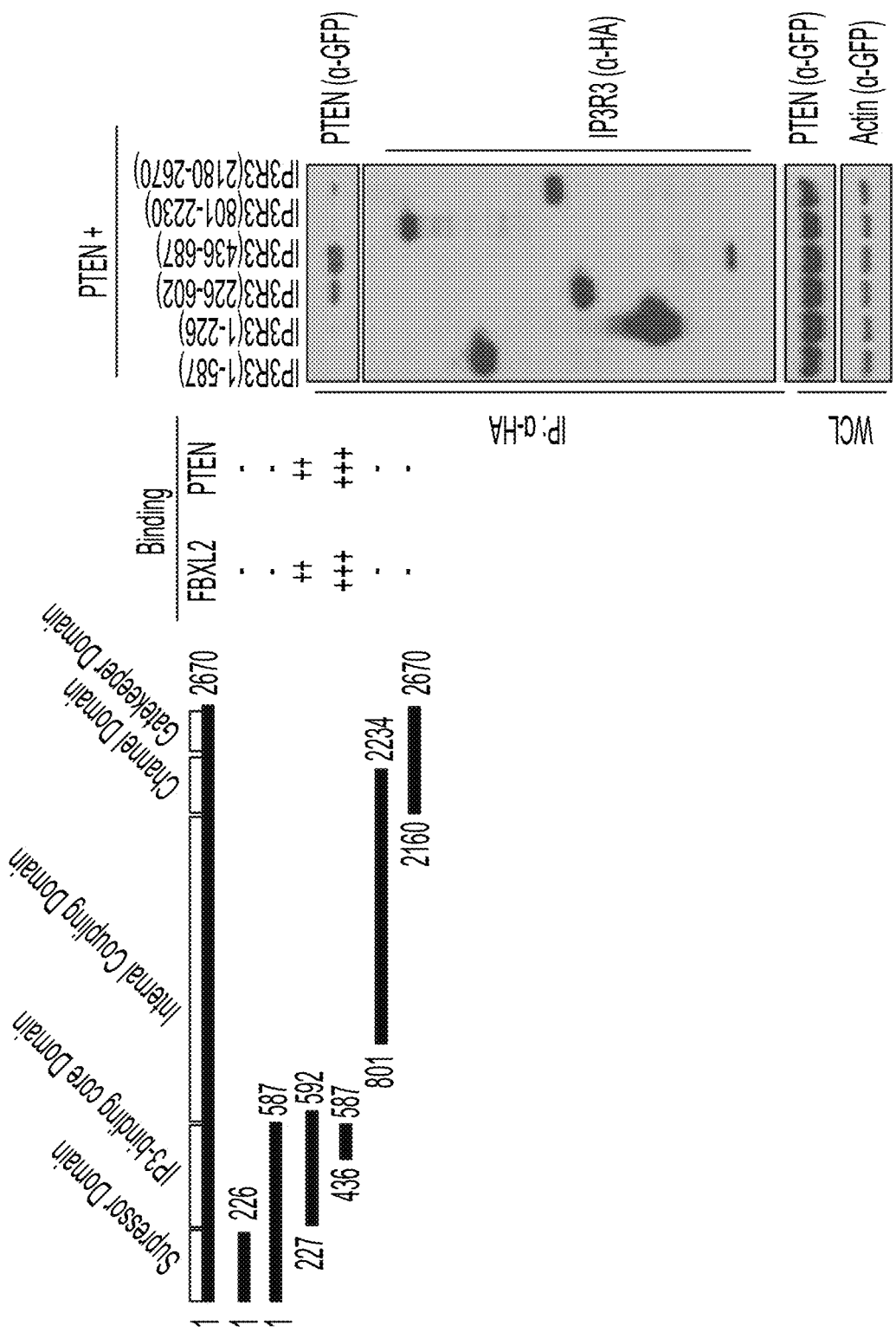

We then stably transfected A549 and PC3 cells with either an empty vector or IP3R3(Q-FR/A-AA) for xenograft transplantation experiments in NOD/SCID gamma mice. These xenografts did not show any significant difference in growth curves (FIG. 4a and Extended Data FIG. 10a). However, PDT significantly reduced the tumour weight and growth rate of IP3R3(Q-FR/A-AA) expressing xenografts, whereas empty vector xenografts were unaffected (FIG. 4a and Extended Data FIG. 10a). Accordingly, in response to PDT, increased apoptosis was detected in IP3R3(Q-FR/A-AA) xenografts compared to empty vector xenografts (FIG. 4b and Extended Data FIG. 10b). Virtually identical results were obtained using a A549 knock-in clone expressing endogenous IP3R3(Q-1R/A-AA) (Extended Data FIG. 10c, d).

Figure 4C:
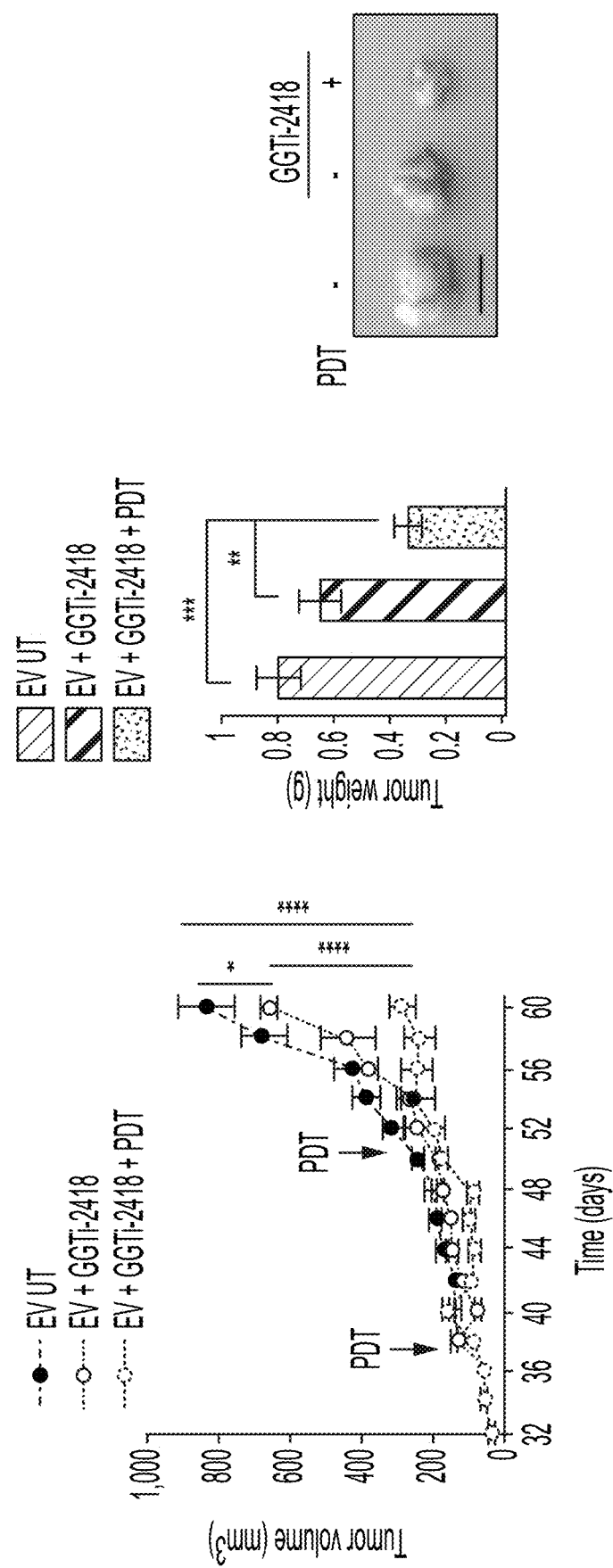
Figure 4D:
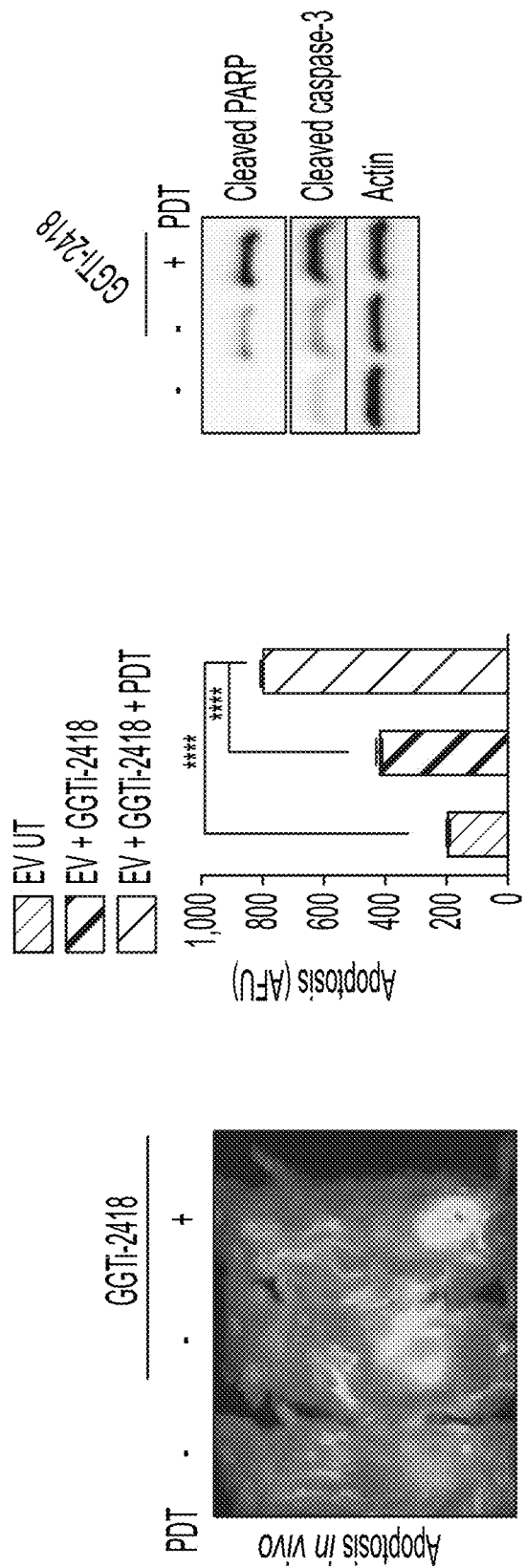

We also administered intratumoural injections of GGTi-2418, which is currently used in various clinical trials[7], delocalizes FBXL2 from membranes, and stabilizes IP3R3 (see above). GGTi-2418, by itself, only modestly affected the growth rate of xenografts. However, GGTi-2418 significantly sensitized tumour xenografts to PDT (FIG. 4c, d).

Figures 10E, 10F:
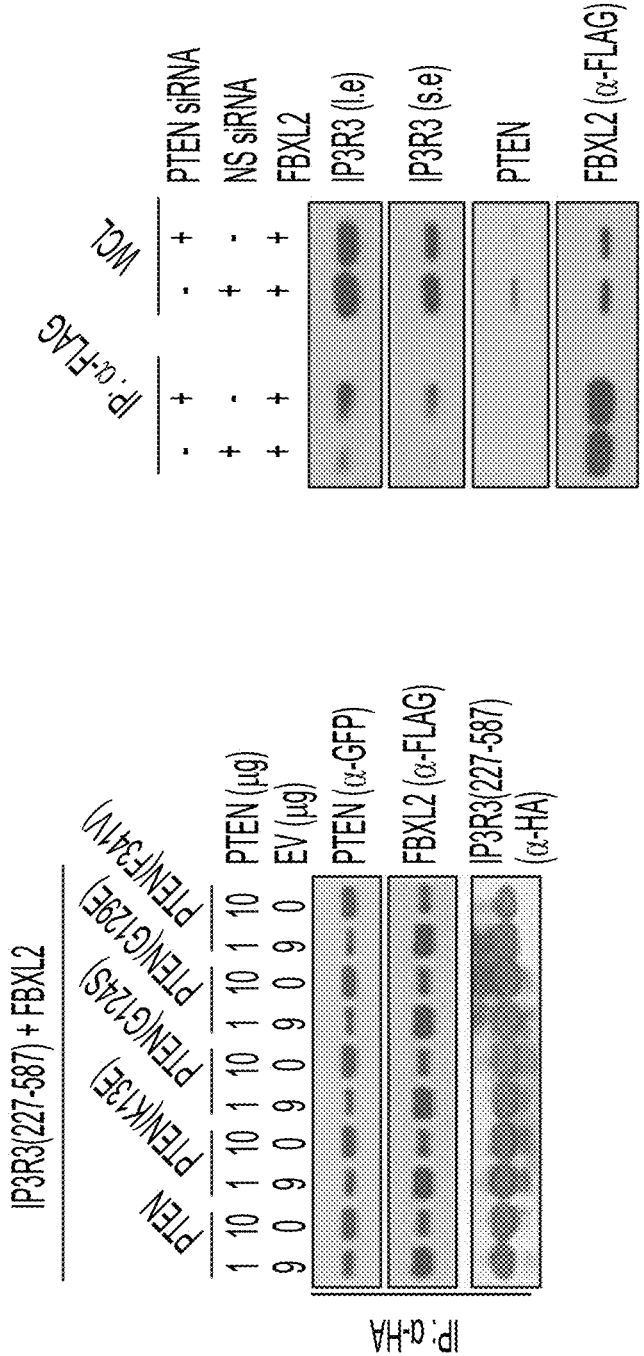
Figure 10H:
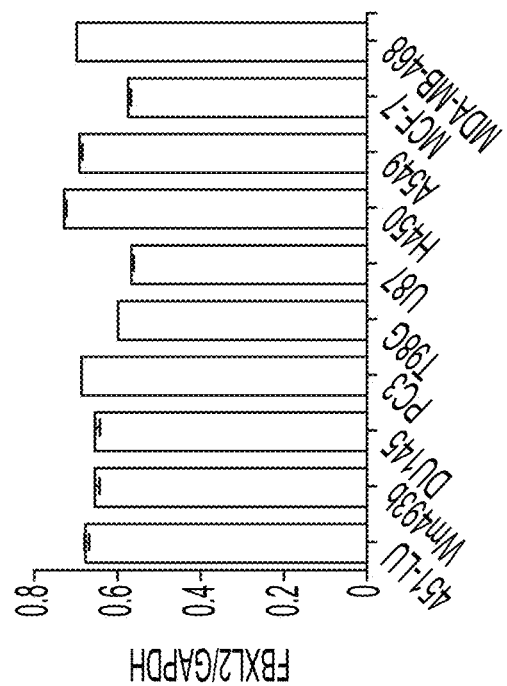
Figure 10G:
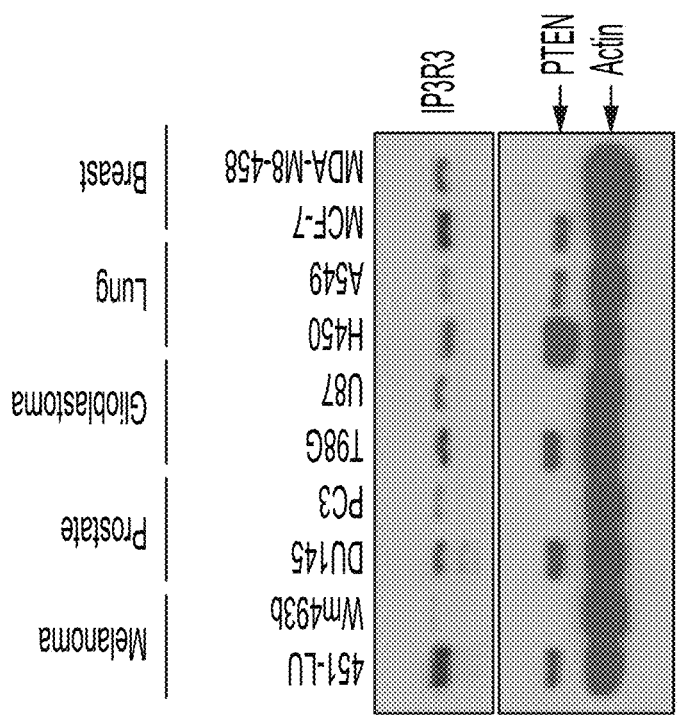
Figures 10I, 10J:
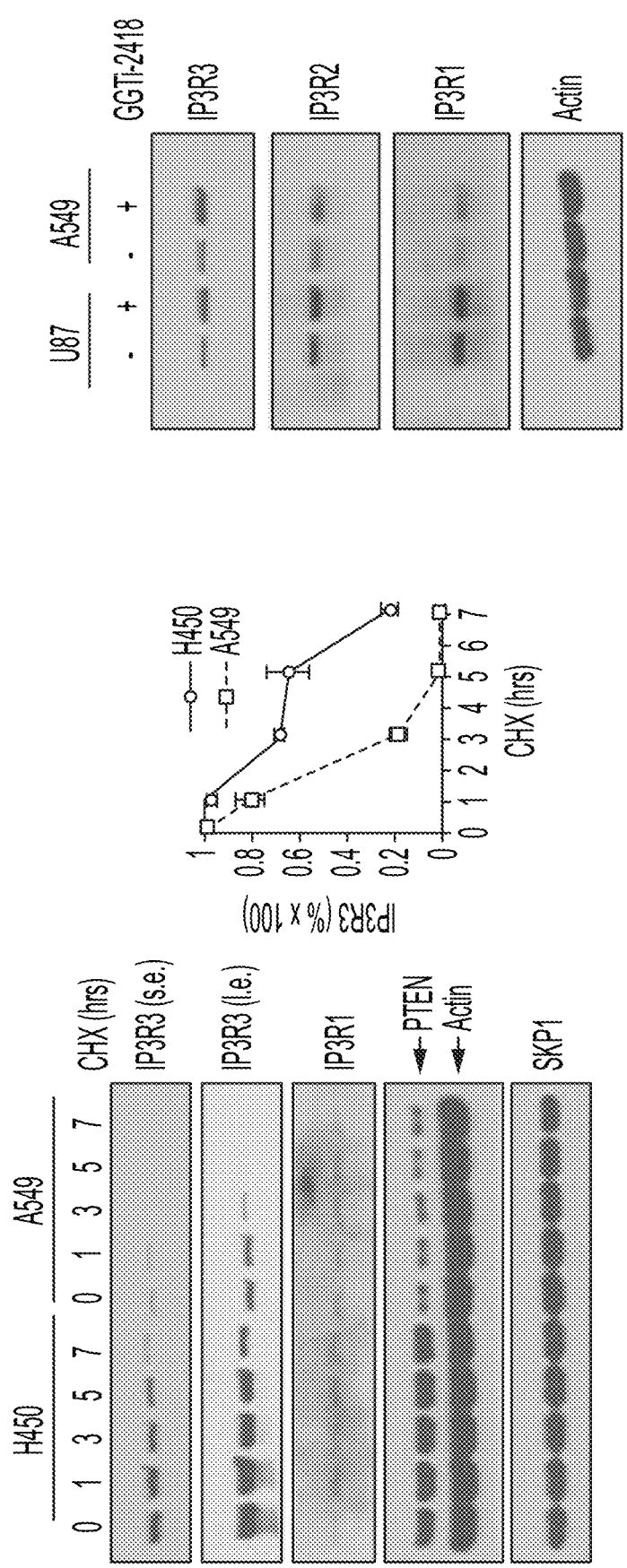
Figure 10K:
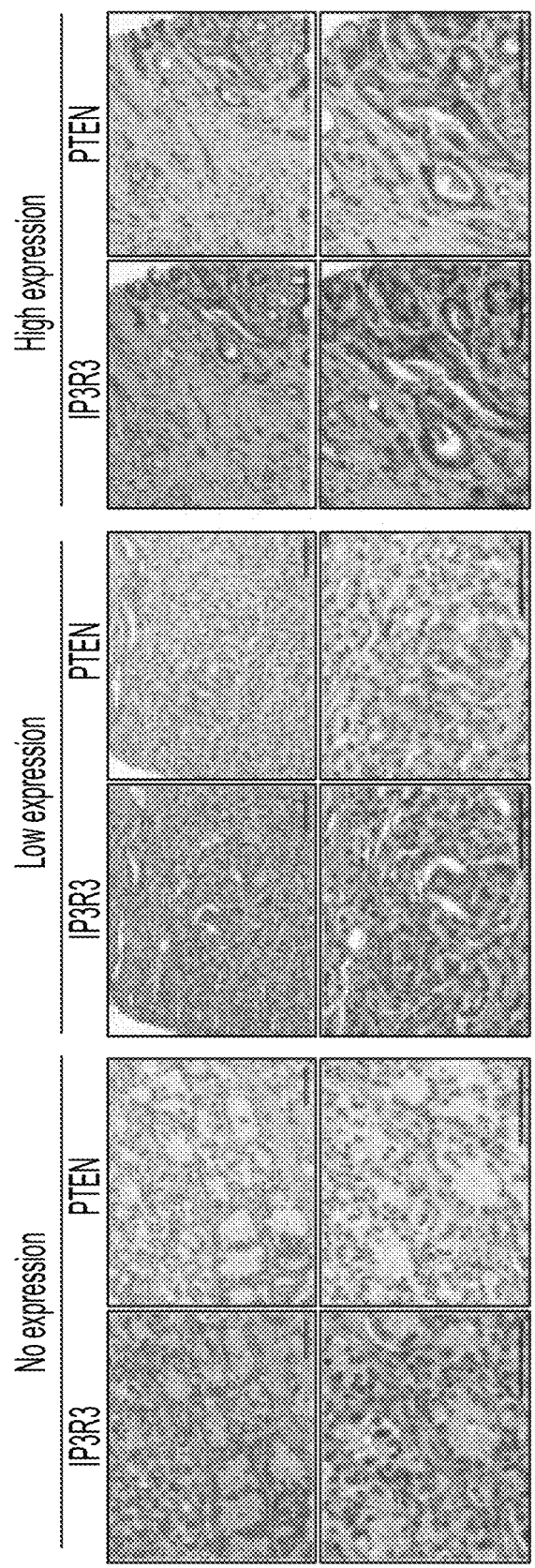

Recent studies suggest that non-catalytic activities of PTEN contribute to its tumour suppressor function through poorly defined mechanisms. Our study reveals a phosphatase-independent mechanism by which PTEN functions as a tumour suppressor (Extended Data FIG. 10e). Moreover, we show that when IP3R3 degradation is inhibited, tumours with no or low levels of PTEN expression become sensitive to PDT. We propose that such tumours should not only be treated with inhibitors targeting the PI3K signalling cascade (which is hyperactive in these cancers), but also with drugs that result in IP3R3 stabilization, thereby abrogating both arms of PTEN function.

REFERENCES CITED IN THIS EXAMPLE

1. Wright, F. A. & Wojcikiewicz, R. J. Chapter 4—inositol 1,4,5-trisphosphate receptor ubiquitination. Frog. Mol. Biol. Transl. Sci. 141, 141-159 (2016).
2. Orrenius, S., Zhivotovsky, B. & Nicotera, P. Regulation of cell death: the calcium-apoptosis link. Nat. Rev. Mol. Cell Biol. 4, 552-565 (2003).
3. Skaar, J. R., Pagan, J. K. & Pagano, M. Mechanisms and function of substrate recruitment by F-box proteins. Nat. Rev. Mol. Cell Biol. 14, 369-381 (2013).
4. Hollander, M. C., Blumenthal, G. M. & Dennis, P. A. PTEN loss in the continuum of common cancers, rare syndromes and mouse models. Nat. Rev. Cancer 11, 289-301 (2011).
5. Brown, S. B., Brown, E. A. & Walker, I. The present and future role of photodynamic therapy in cancer treatment. Lancet Oncol. 5, 497-508 (2004).

6. Giorgi, C. et al. Intravital imaging reveals p53-dependent cancer cell death induced by phototherapy via calcium signaling. Oncotarget 6, 1435-1445 (2015).
7. Kazi, A. et al. Blockade of protein geranylgeranylation inhibits Cdk2-dependent p27Kip1 phosphorylation on Thr187 and accumulates p27Kip1 in the nucleus: implications for breast cancer therapy. Mol. Cell. Biol. 29, 2254-2263 (2009).
8. Wang, C. et al. Identifi of FBL2 as a geranylgeranylated cellular protein required for hepatitis C virus RNA replication. Mol. Cell 18, 425-434 (2005).
9. Kuchay, S. et al. FBXL2- and PTPL1-mediated degradation of p110-free p85β regulatory subunit controls the PI(3)K signalling cascade. Nat. Cell Biol. 15, 472-480 (2013).
10. Deshaies, R. J. Proteotoxic crisis, the ubiquitin-proteasome system, and cancer therapy. BMC Biol. 12, 94 (2014).
11. Clapham, D. E. Calcium signaling. Cell 131, 1047-1058 (2007).
12. Bittremieux, M., Parys, J. B., Pinton, P. & Bultynck, G. ER functions of oncogenes and tumor suppressors: Modulators of intracellular Ca(2+) signaling. Biochim Biophys. Acta 1863 (6 Pt B), 1364-1378 (2016).
13. Puc, J. et al. Lack of PTEN sequesters CHK1 and initiates genetic instability. Cancer Cell 7, 193-204 (2005).

Methods

No statistical methods were used to predetermine sample size and the investigators were not blinded to allocation during experiments and outcome assessment. Antibodies, reagents, and biochemical methods Immunoprecipitation and immunoblotting experiments were performed as previously described[9,14,15]. In some experiments, 2-4% of whole-cell lysate inputs (depending on the protein of interest) were run together with immunoprecipitates. The following antibodies were used: IP3R1(Bethyl no. A302-157A), IP3R-2 (Millipore no. AB3000), IP3R3 (BD-Pharmingen no. 610312), PTEN (Cell Signaling Technology no. 9559S), calnexin (Santa Cruz no. sc11397), cleaved PARP (Cell Signaling Technology no. 5625S), cleaved caspase-3 (Cell Signaling Technology #9661S), cytochrome c (BD no. 556433), AKT (Cell Signaling Technology no. 2920S), pAKT-5473 (Cell Signaling Technology no. 4058S), GFP (Cell Signaling Technology no. 2956S), CUL1 (Invitrogen no. 718700), SKP1 (generated in-house), Flag (Sigma), HA (Covance), α-tubulin (Sigma), and β-actin (Sigma). Isotype-specific horseradish peroxidase conjugated secondary antibodies were used for detection by enhanced chemiluminescence (Pierce). All cDNA constructs were N-terminally tagged either with Flag, HA, GFP or GST (specific details provided on request).

Cell culture and transfections. Cell lines and primary fibroblasts were purchased from ATCC, except where indicated. All cell lines were treated with Plasmocin and tested with Universal Mycoplasma Detection Kit from ATCC. NHFs were grown in Dulbecco's modified Eagle's medium (DMEM) supplemented with 10% FBS. MEFs (Pten+/+ and Pten−/−, provided by R. Parsons' laboratory)13, HeLa, and COS-7 cells (African Green Monkey SV40-transformed kidney fibroblasts) were grown in DMEM supplemented with 10% FBS and transfected as described9. All cells grown in culture were periodically monitored for mycoplasma contamination. Cells were starved for the indicated time periods in 0.1% FBS. Cells were serum-stimulated with DMEM supplemented with 10% FBS. Where indicated, cells were treated with 10 µM MG132 (Peptides International), 100 µM cycloheximide (Sigma), 10-15 µM GGTi-2418 (Moffit Cancer Center), 10 µM Eeyarestatin 1 (Eer1, TOCRIS bioscience), 100 µM histamine (Sigma), 10 µM MRS2578 (Sigma), 100 µM ATP (Sigma), and 1 µM cyclosporin-A (Sigma).

Tandem affinity purification and mass spectrometry. HEK293T cells were transiently transfected with Flag-HA-tagged FBXL2 or control plasmids using polyethylenimine (PEI). Twenty-four hours after transfection, cells were treated with MG132 (10 µM) for 3 h before harvesting Immunoprecipitation and subsequent mass spectrometry was carried out as previously described9,14,15. The original mass spectrometry data can be accessed through the Stowers Original Data Repository.

Gene silencing. For gene silencing, cells were seeded approximately 24 h before transfection. The following ON-TARGETplus siRNA oligos from Dharmacon were transfected (5-15 nM) with HiPerfect for 24-48 h, according to the manufacturer's instructions (Qiagen): ON-TARGETplus human FBXL2 (oligo 1 GCACAGAACUGCCGAAACA, oligo 2 GCUCGGAAUUGCCACGAAU, oligo 3 J-0113562-07-0005); ON-TARGETplus human ITPR3 (L-006209-00-0005); ON-TARGETplus mouse ITPR3 (L-065715-01-0005) siRNA, ON-TARGETplus mouse PTEN (L-040700-02-0005); ON-TARGETplus human PTEN (L-003023-00-0005); and ON-TARGET non-targeting siRNA 1 (D-001810-01-05). To validate gene silencing by RT-PCR, total RNA was isolated using Qiagen's RNeasy kit (cat. no. 74104). The reverse transcription reaction was carried out in triplicate using 5 µg of total RNA using Oligo-dT primers with Superscript III RT polymerase (Invitrogen) according to the manufacturer's instructions. The real-time qPCR reaction was carried out using 250 ng cDNA using SYBR Green method with Roche Light Cycler 48011 machine in a 96-well format. Data were analysed using 2nd derivative maximum with high confidence software for RT values according to the manufacturer's guidelines (Roche). Bar graphs represent the relative ratio of FBXL2 to GAPDH values. The following RT-primers were used: human FBXL2, forward: 5'-ATTTGACTGACGCAGGTTT-3', reverse: 5'-GAGCTG GATGAGTGTGCTGT-3'; human GAPDH, forward: 5'-TGCACCACCAACT GCTTAGC-3', reverse: 5'-GGCATGGACTGTGGTCATGAG-3'.

Ubiquitination assays. Briefly, HEK-293T cells were co-transfected with HA- or GFP-tagged IP3R3 (either wild-type or an N-terminal fragment) and either Flag-tagged FBXL2 or an FBXL2(ΔF-box) mutant. Twenty-four hours after transfection, cells were incubated with MG132 for three hours before harvesting. FBXL2 (wild-type and mutant) was immunoprecipitated with anti-Flag M2 agarose beads (Sigma) and in vitro ubiquitination assays were carried out as previously described[9,16] Flag-tagged trypsin-resistant tandem ubiquitin-binding entity (TR-TUBE), which directly binds polyubiquitin chains and protects them from proteasome-mediated degradation was used for cell-based assays, as previously described[17,18].

Fura-2 measurements. The cytosolic Ca2+ response was evaluated using the fluorescent Ca2+ indicator Fura-2/AM (Thermo Fischer Scientific). In brief, cells were grown on 24-mm coverslips and incubated at 37° C. for 30 mM in 1 mM Ca2+ in Krebs-Ringer buffer (KRB: 135 mM NaCl, 5 mM KCl, 1 mM MgSO4, 0.4 mM K2HPO4, 5.5 mM glucose, 20 mM HEPES) supplemented with 2.5 mM Fura-2/AM, 0.02% Pluronic F-68 (Sigma-Aldrich), and 0.1 mM sulfinpyrazone (Sigma-Aldrich). Cells were then washed and supplied with 1 mM Ca2+/KRB. Next, cells were placed in an open Leyden chamber on a 37° C. thermostated stage and exposed to 340/380 nm wavelength light using the Olympus xcellence (Olympus) multiple wavelength high-resolution fluorescence microscopy system equipped with an Hamamatsu ORCA ER CCD camera (Hamamatsu Photonics) and a Up1 FLN 40× oil objective (Olympus) to determine the cytosolic Ca2+ response. The photoactivation of aluminium phthalocyanine chloride was obtained using an excitation filter ET576/25 (Semrock), with 500 ms of excitation every cycle. Cytosolic Ca2+ concentration was calculated as previously described[19,20].

FRET-based measurements of mitochondrial Ca2+. Single-cell measurements of mitochondrial Ca2+ were performed in A549 cells or A549 knock-in clones transfected with 4mtD3cpv (ref. 6). After 36 h, cells were imaged using a Zeiss Axiovert 200 M microscope with a cooled CCD camera (Photometrics), which was equipped with a C-apochromatic 40×/1.2 W CORR objective and controlled by MetaFluor 7.0 software (Universal Imaging) Emission ratio imaging of the 4mtD3cpv was achieved using a 436DF20 excitation filter, a 450 nm dichroic mirror, and two emission filters (475/40 for ECFP and 535/25 for citrine) that were controlled by a Lambda 10-2 filter changer (Sutter Instruments). The acquired fluorescence images were corrected for the background. The exposure times were typically 100-200 ms, and images were collected every second per wavelength. The photo-activation of aluminium phthalocyanine chloride was achieved using an excitation filter ET650/50 (Chroma Technology) with 500 ms of excitation every FRET ratio cycle.

Aequorin measurements. Cells were transfected with the mtAEQ chimaera alone or together with constructs expressing FBXL2 or IP3R3. All aequorin measurements were carried out in KRB buffer supplemented with 1 mM CaCl2. Agonists and other drugs were added to the same medium, as specified in the figure legends. The experiments were terminated by lysing cells with 100 μM digitonin in a hypotonic Ca2+-rich solution (10 mM CaCl2), thus discharging the remaining aequorin pool. The light signal was collected and calibrated into [Ca2+] values, as previously described[21].

Experimental animals. Procedures involving animals and their care conformed with institutional guidelines, and all experimental protocols were approved by the animal ethics committee. NOD/SCID gamma (NSG) mice were housed in sterile conditions within high-efficiency particulate arrestance filtered micro-isolators, and fed with irradiated food and acidified water. Six-week-old male NSG mice were injected subcutaneously (s.c.) with 2×106 cells. When tumour mass became palpable in successfully engrafted mice (around 36 days after the injection of A549 cells and around 70 days after the injection of PC3 cells), animals were randomly divided into different groups and subjected to various treatments as indicated in the figures. When indicated, mice were subject to two rounds of GGTi-2418 treatment (50 mg kg-1) by intratumoural injection for five consecutive days. Tumour growth was monitored daily, and tumour diameters were measured with callipers every other day. The tumour volume was calculated using the following equation: volume=π/6 ×(a×b2), where a is the major diameter and b is the minor diameter. At the end of the experiment, tumour progression was confirmed by either retro-orbital or intravenous injection of fluorescently labelled IRDye 2-deoxyglucose (2-DG), which was detected 24 h after injection using a Pearl Trilogy Imaging System (Li-Cor). All mice that reached the endpoint of the experiment (60 days for A549 or 92 days for PC3 cells) were euthanized and, subsequently, tumours were excised, weighted, and either immunoblotted or sectioned for immunofluorescence.

Detection of cell death in cell systems. For cell death induction, cells were treated with different apoptotic stimuli as indicated in the text and figure legends. Apoptosis was determined by three different methods: (i) by blotting for different cell death markers, such as cleaved PARP and cleaved CASPASE-3; (ii) by analysing cytochrome c release; and (iii) by automated nuclei count analysis. For analysis of cytochrome c release, cells were fixed with 4% paraformaldehyde in PBS for 20 min, washed three times with PBS and then incubated for 10 mM in PBS. Cells were then permeabilized with 0.1% Triton X-100 in PBS, followed by a 1-h wash with 2% milk in PBS. Cells were then incubated overnight at 4° C. in a wet chamber with a mouse anti-cytochrome c antibody followed by incubation with an Alexa 594 goat anti-mouse antibody and DAPI for 1 h at room temperature. After antibody incubation, cells were washed three times with PBS. Images were acquired on an Olympus Scan^R station using a laser based autofocus and an image-based autofocus. Eighty fields were acquired for each well using a 20× magnification objective, NA 0.75. The different fluorophores were excited by an MT20 illumination system with 377/50, 595/30 excitation filters. Images were collected using an Orca-R2 CCD camera (Hamamatsu Photonics), without binning. The mean fluorescence intensities and standard deviations of nuclear cytochrome c were evaluated in comparison to corresponding controls. Automated nuclei count analysis was performed by seeding 50,000 cells on a 25-mm coverslip. Cells were grown for 48 h before treatment with H2O2 (1-2 mM for 4-16 h as indicated in figure legends) or etoposide (50 μM for 5 h). Coverslips were stained with Hoechst 10 μM, placed in an incubated chamber with controlled temperature, and mounted on a Zeiss Axiovert 200 M microscope equipped with a motorized stage. Images of nuclei (ranging in size from 5-25 μm) were acquired with a 10× Fluor objective (Zeiss) and a CoolSnap HQ CCD camera. Twenty random fields were acquired using the random stage scan tools in MetaMorph and analysed with the nuclei count application.

Detection of cell death in vivo. After a retro orbital injection of 100 μl of CAS-MAP NIR probe (Vergent Bioscience), the reagent was allowed to circulate in mice for 30 min before analysis. Fluorescent in vivo images were acquired using a Pearl Trilogy Imaging System (Li-Cor). For the analysis of apoptosis in tumour tissue sections, after a retro orbital injection of 100 μl of SR-FLIVO probe (Immunochemistry Technology), the reagent was allowed to circulate in mice for 30 min. Tumours were excised, frozen, sectioned, and stained for nuclei using DRAQS, according to the manufacturer's protocol (Cell Signaling Technology). After staining, the samples were mounted on coverslips and analysed using a Zeiss LSM 510 confocal microscope equipped with a Fluor 40×/1.30 NA oil-immersion objective. The acquired images were background corrected, and signals were analysed using Fiji software.

Sub-cellular fractionation. Cells (approximately 109) were harvested, washed in phosphate-buffered saline medium, pelleted by centrifugation at 500 g for 5 min, re-suspended in homogenization buffer (0.25 M sucrose and 10 mM HEPES pH 7.4) and gently disrupted by dounce homogenization. The homogenate was centrifuged twice at 600 g for 5 min to remove cellular debris and nuclei, and the supernatant was centrifuged at 10,300 g for 10 min to pellet crude mitochondria. The resultant supernatant was centrifuged at 100,000 g for 1 h in a Beckman 70 Ti rotor at 4° C. to pellet microsomes, which were re-suspended in homogenization buffer[22]. The quality of the preparation was confirmed by immunoblot analysis using different markers for the fractions obtained (that is, calnexin as endoplasmic reticulum marker, and β-actin as cytosolic markers).

Immunohistochemistry in human tissue specimens. Expression of PTEN and IP3R3 was assessed by immunohistochemistry using eight available tissue microarrays (TMAs) and one commercially available TMA. The eight TMAs were built generating triplicate cores from radical prostatectomy cases as previously described23, and included 89 prostate adenocarcinomas. The commercially available TMA was from USBiomax and included 60 prostate adenocarcinomas. Five-micrometre sections were deparaffinized and subjected to standard avidin-biotin-based immunohistochemistry procedures as reported in ref. 24. Primary antibodies were anti-PTEN (rabbit monoclonal, Cell Signaling Technology, no. 9559, 1:200 dilution) and anti-IP3R3 (rabbit polyclonal, Bethyl Laboratories, Inc., no. IHC-00639, 1:500 dilution). TMAs were scored by determining the percentage of epithelial prostate cells with immunoreactivity (0=no expression, 1=mild/moderate expression, 2=high and very high expression) for the protein of interest per tissue core. A score was generated for each tissue core by multiplying the percentage of expression by the intensity of expression. The average values of the representative cores from each patient sample were obtained and the median was used as a cut-off to transform protein expression into a qualitative variable. Cases were classified into three categories: 'negative' when score was 0, 'low expression' when score was lower than the median and 'high expression' when score was higher than the median. Linear regression analysis was performed with the GraphPad Prism 7.02 software with $\chi2$ test. Original data are presented in Source Data for FIG. 2d.

Live-cell imaging. HeLa cells were grown in dishes with a glass base (Thermo Scientific no. 150682) in DMEM medium supplemented with 10% FBS. Cells were transfected with GFP-FBXL2 cDNA using Lipofactemine 3000 reagent. Two hours post-transfection, cells were incubated in fresh medium containing GGTi-2418 (15 μM) for 16 h at 37° C. supplemented with 5% CO2. Live-cell imaging was carried out with a Zeiss LSM-510 META confocal microscope using a 63× oil-based objective in an incubation chamber at 37° C. supplemented with 5% CO2. Images were captured and processed with ZEN/ZEN lite imaging software from Zeiss.

Figure 11A:
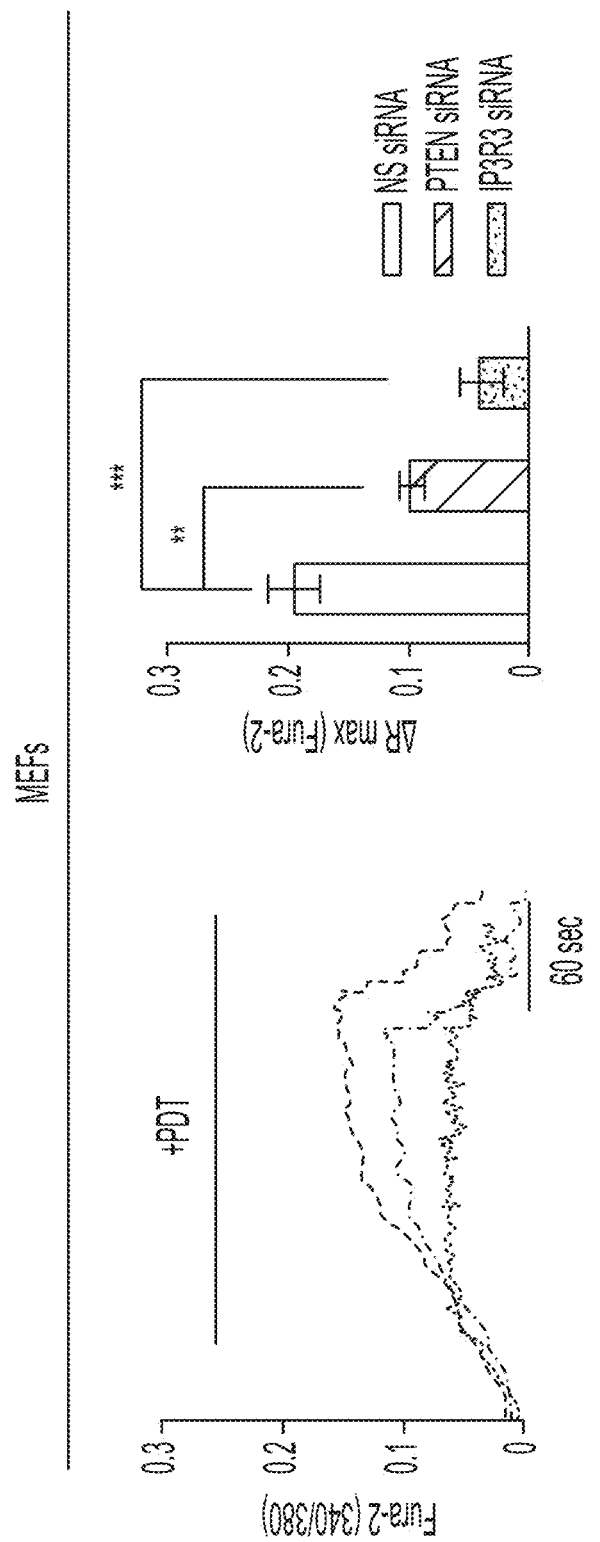
FIGS. 11A, 11B, 11C, and 11D show both wild-type PTEN and a phosphatase dead PTEN mutant sensitize cells to photodynamic therapy.
Figure 11B:
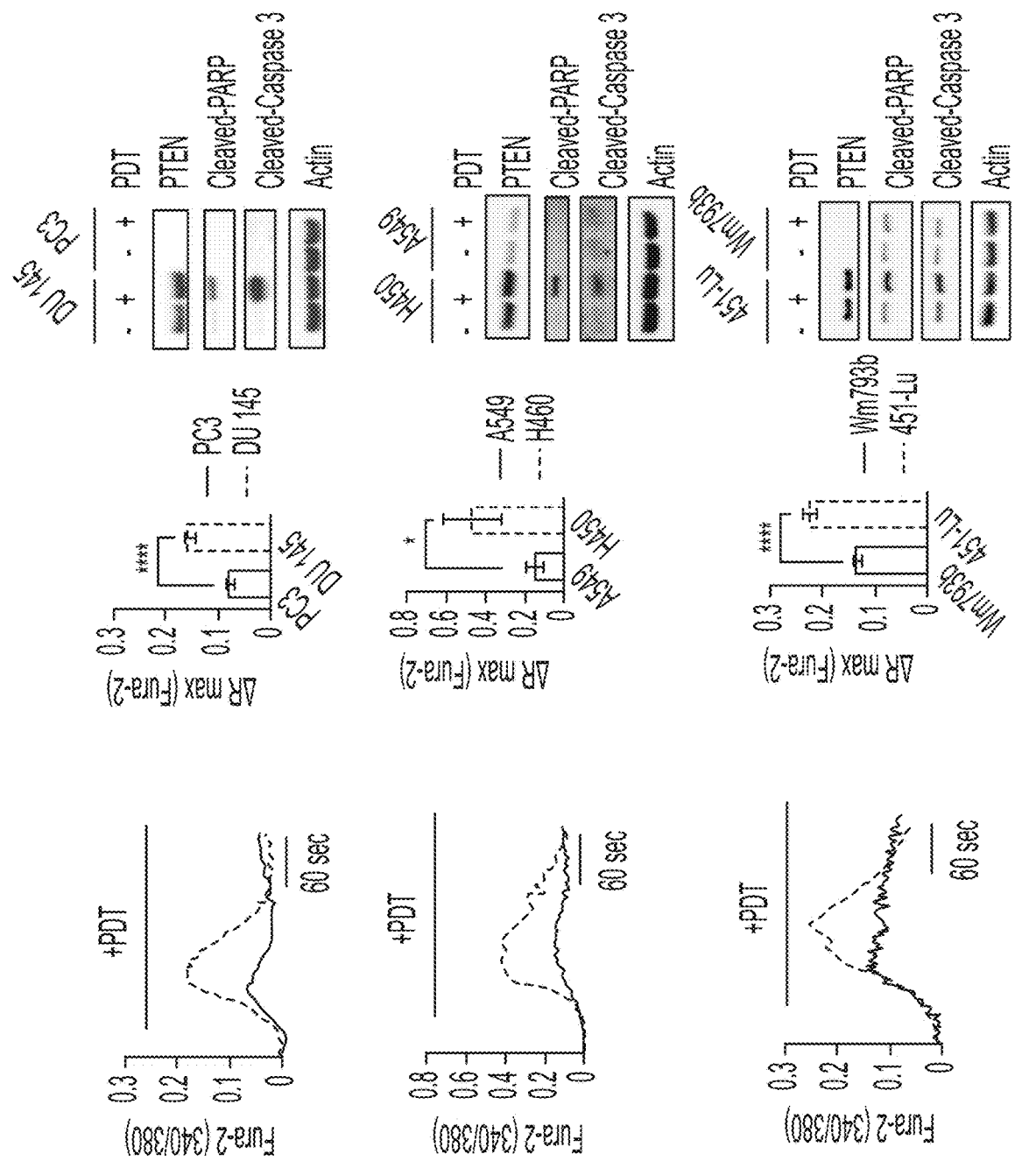
Figure 11C:
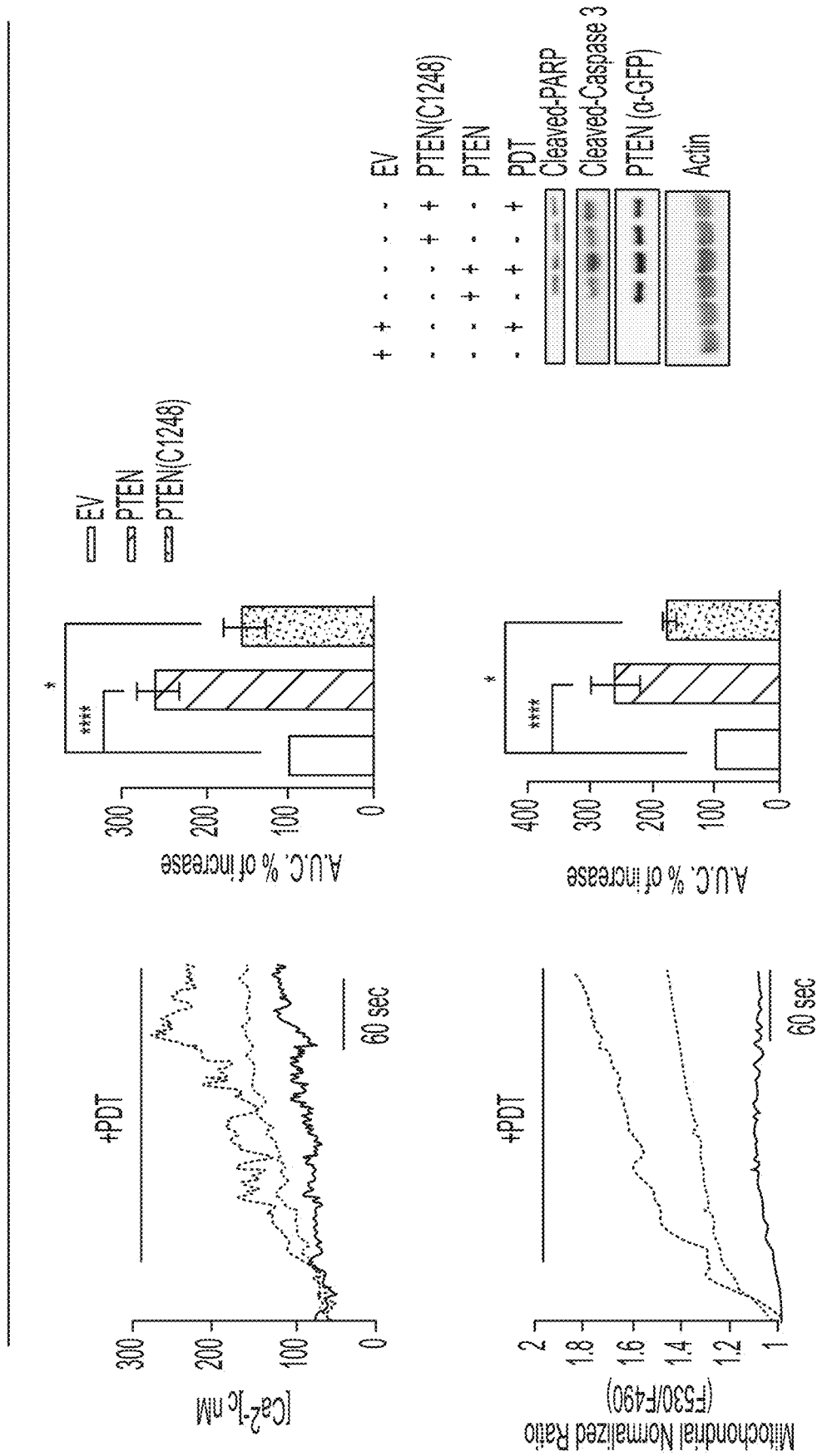
Figure 11D:
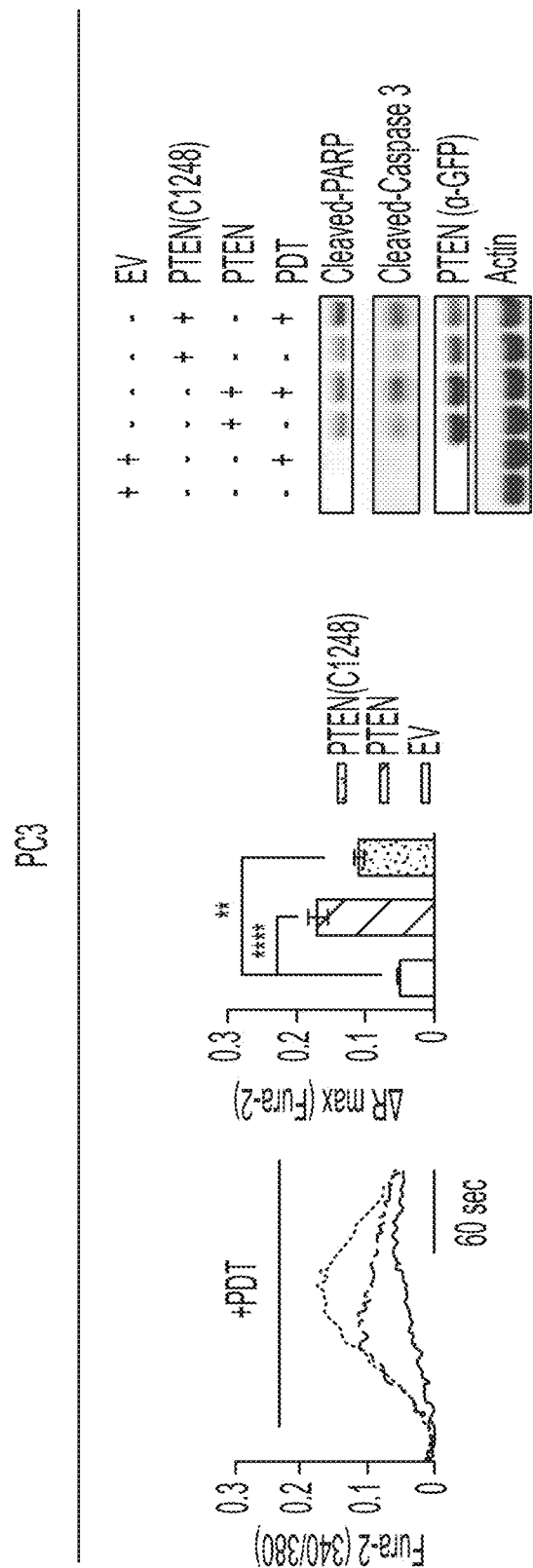
Figure 12A:
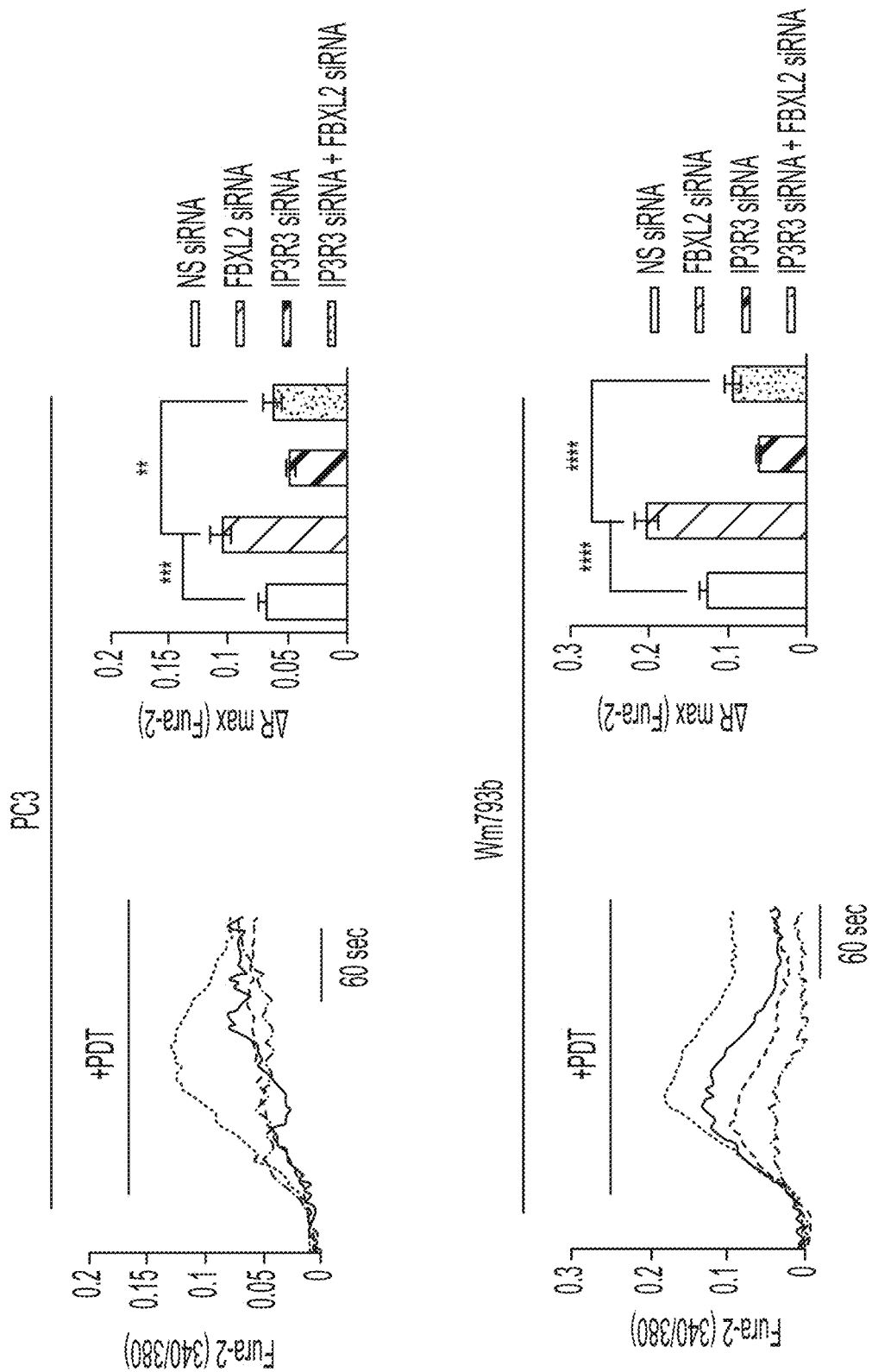
FIGS. 12A and 12B show stabilization of IP3R3 sensitizes cells to photodynamic therapy.
Figure 12B:
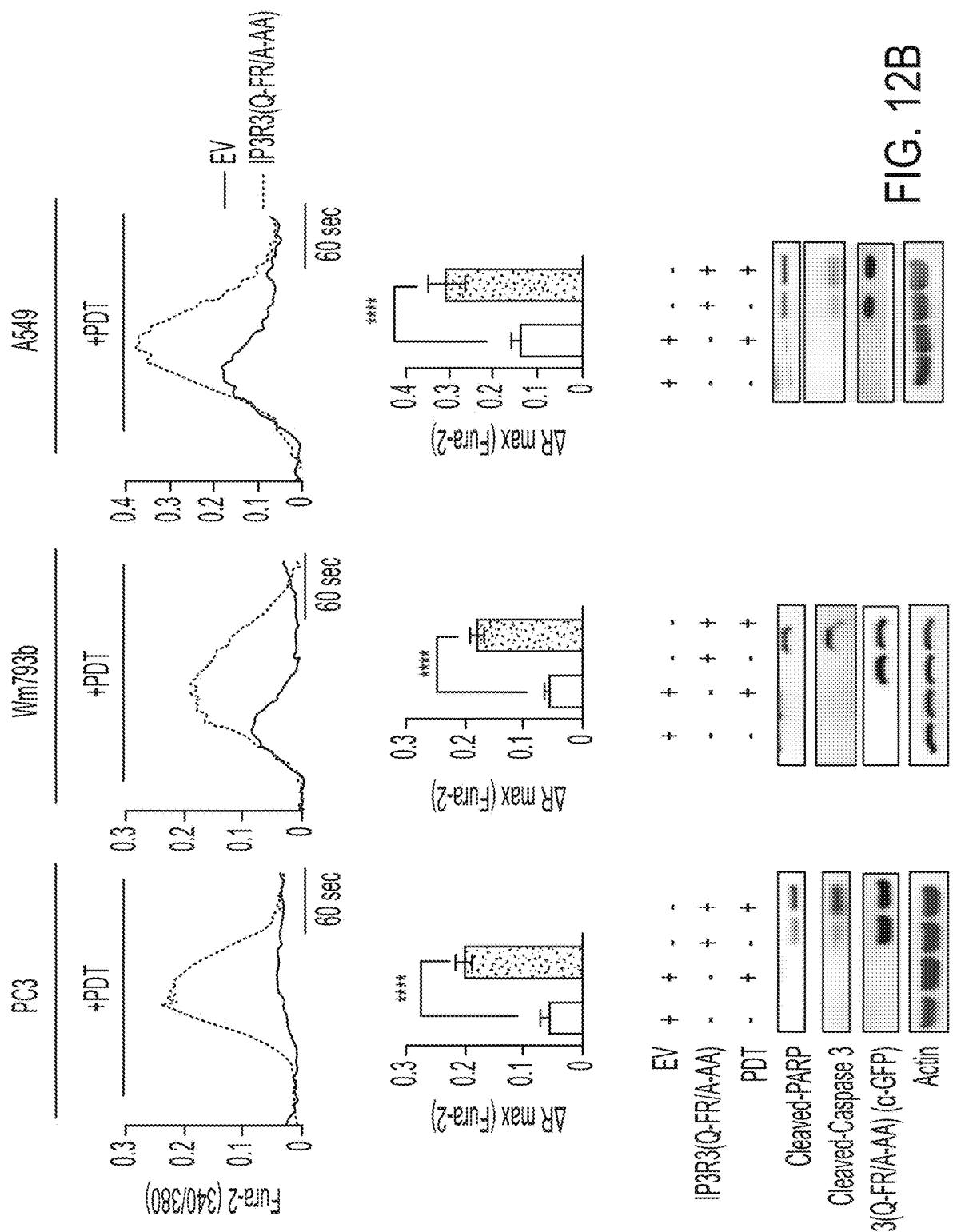
Figure 13B:
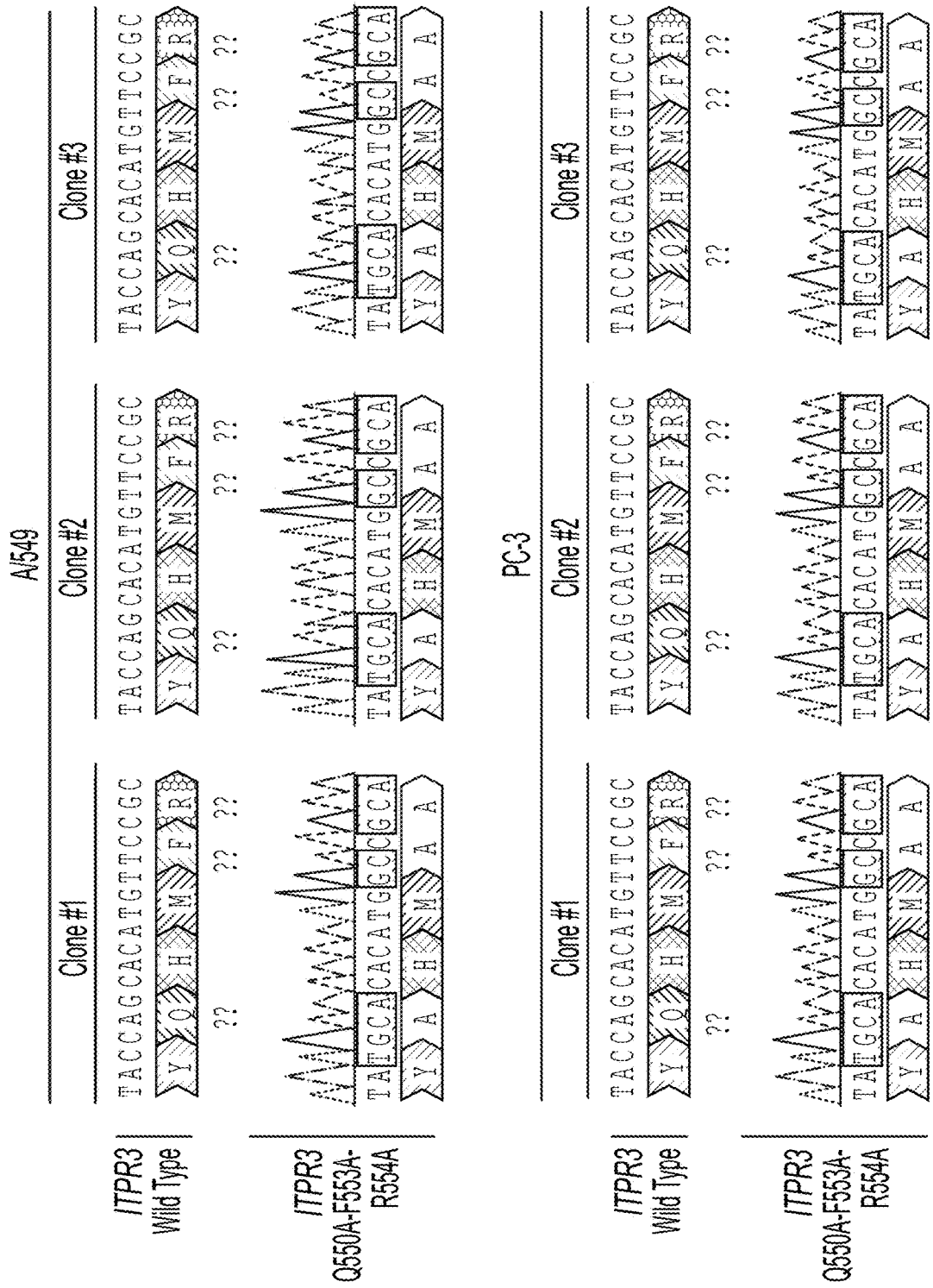
Figure 13E:
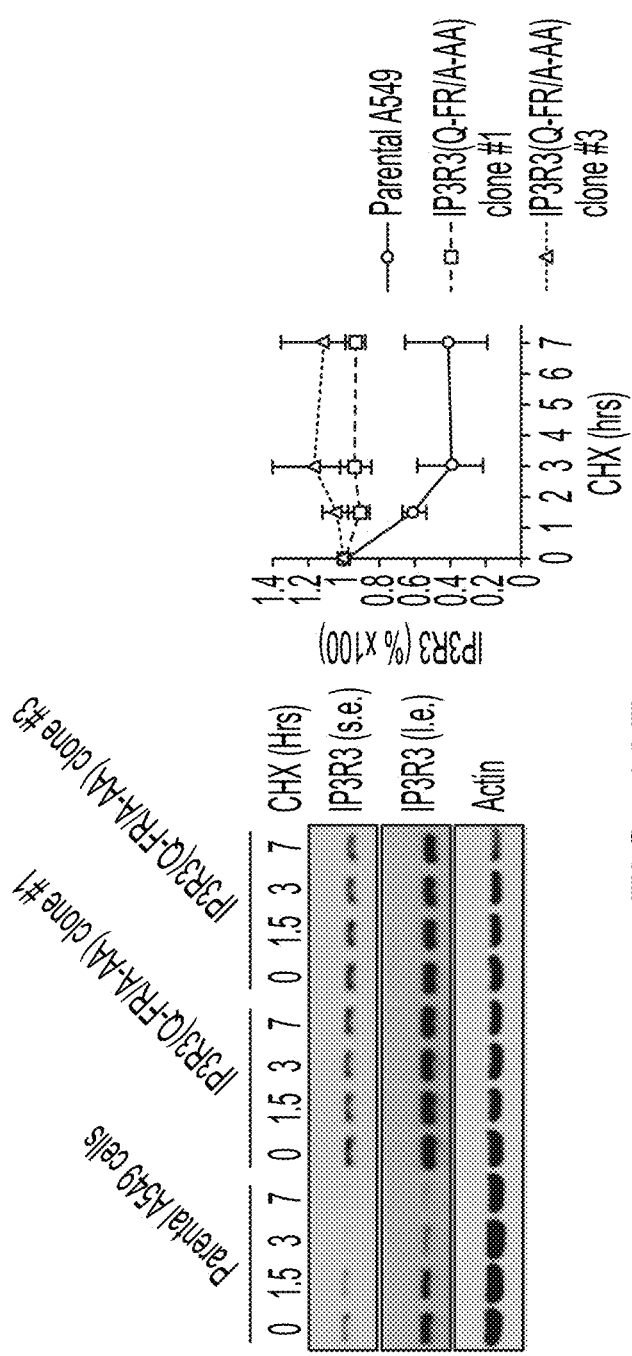
Figure 13D:
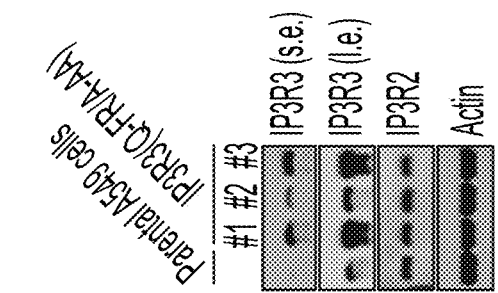
Figures 13F, 13G:
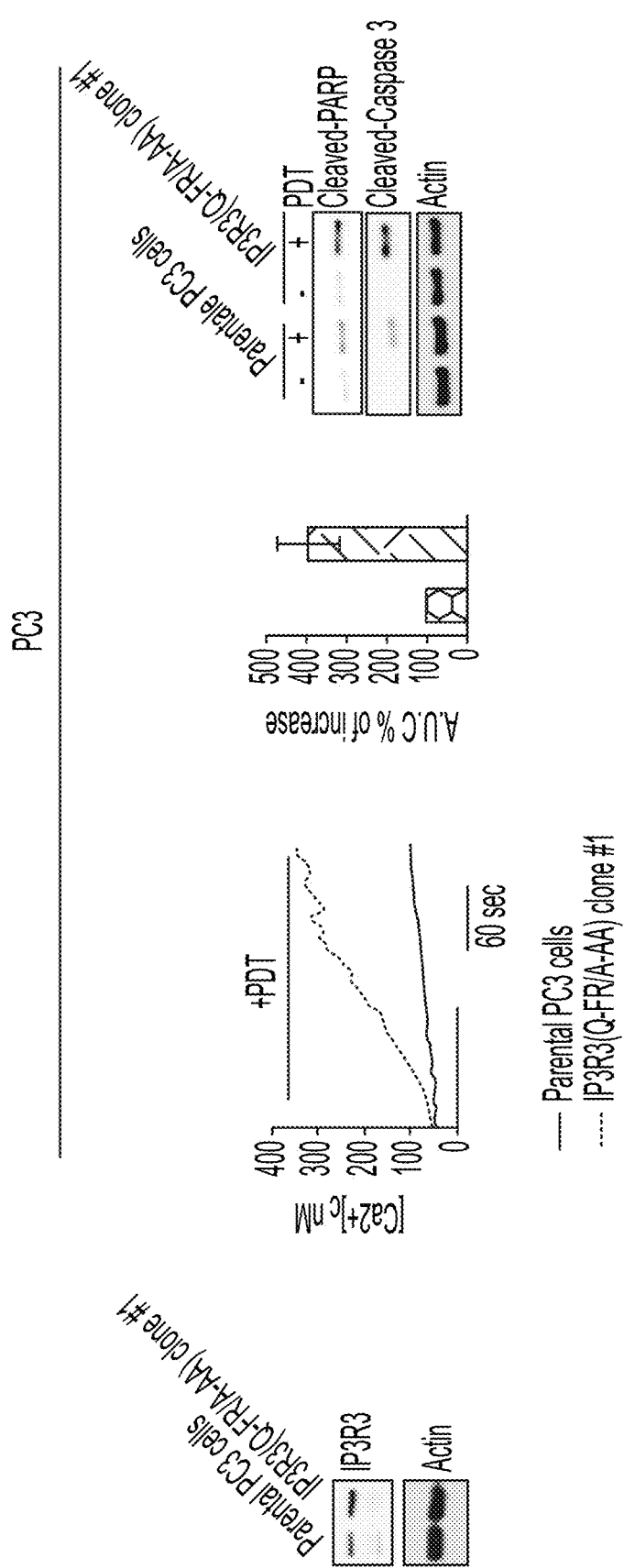
Figure 14A:
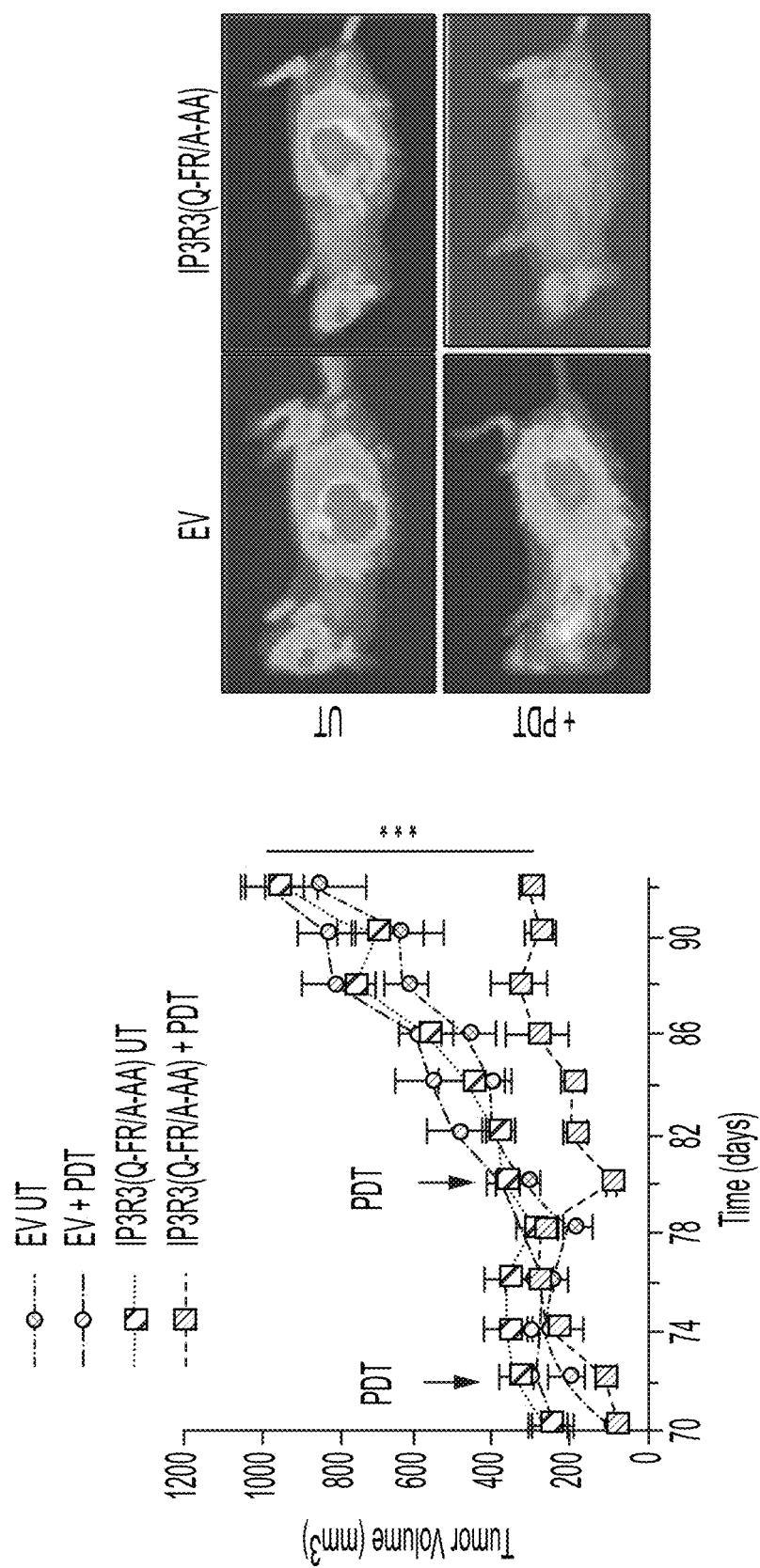
FIGS. 14A, 14B, 14C, 14D, 14E shows that a non-degradable IP3R3 mutant and GGTi-2418 sensitize tumours to photodynamic therapy.
Figure 14A:
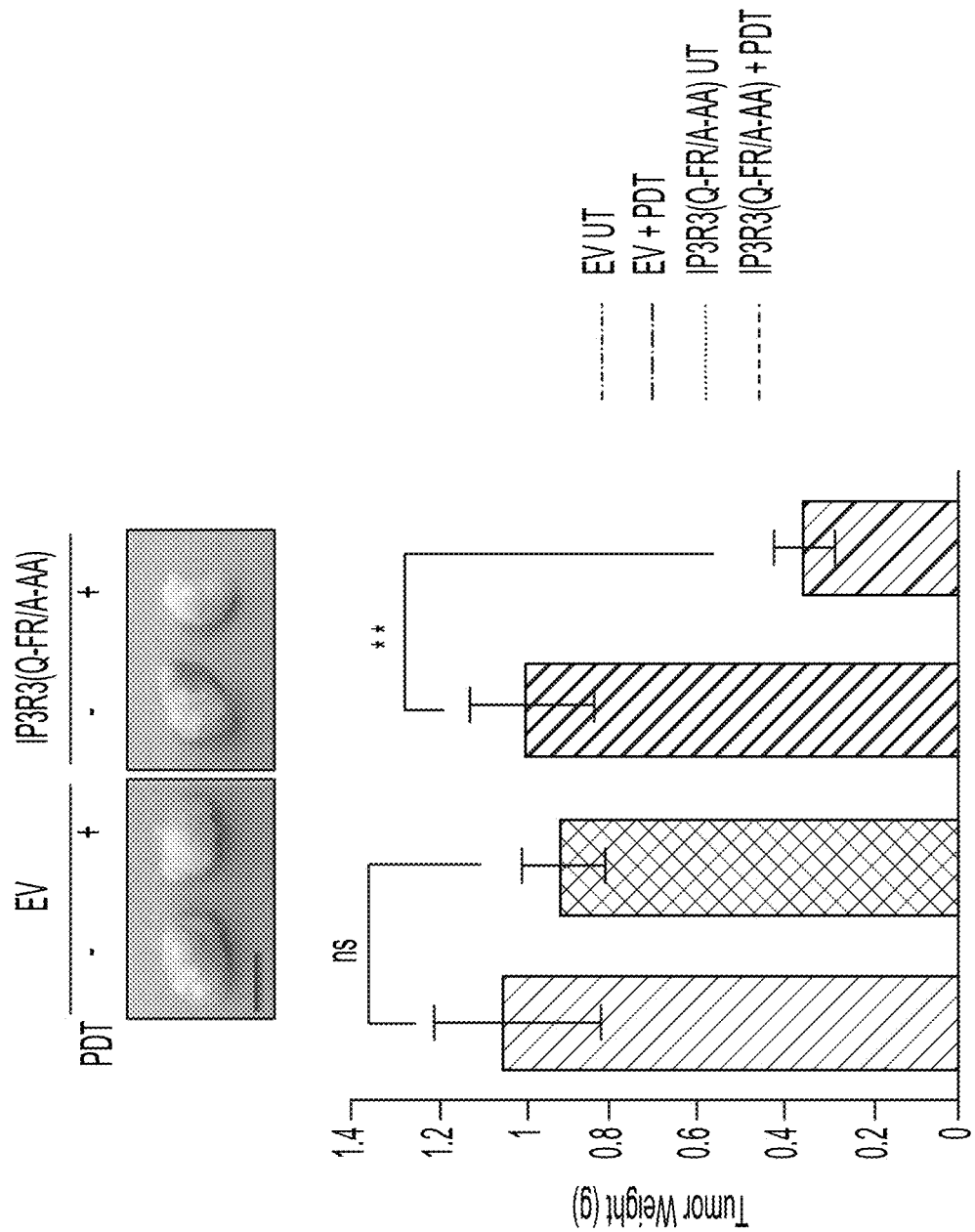
Figure 14B:
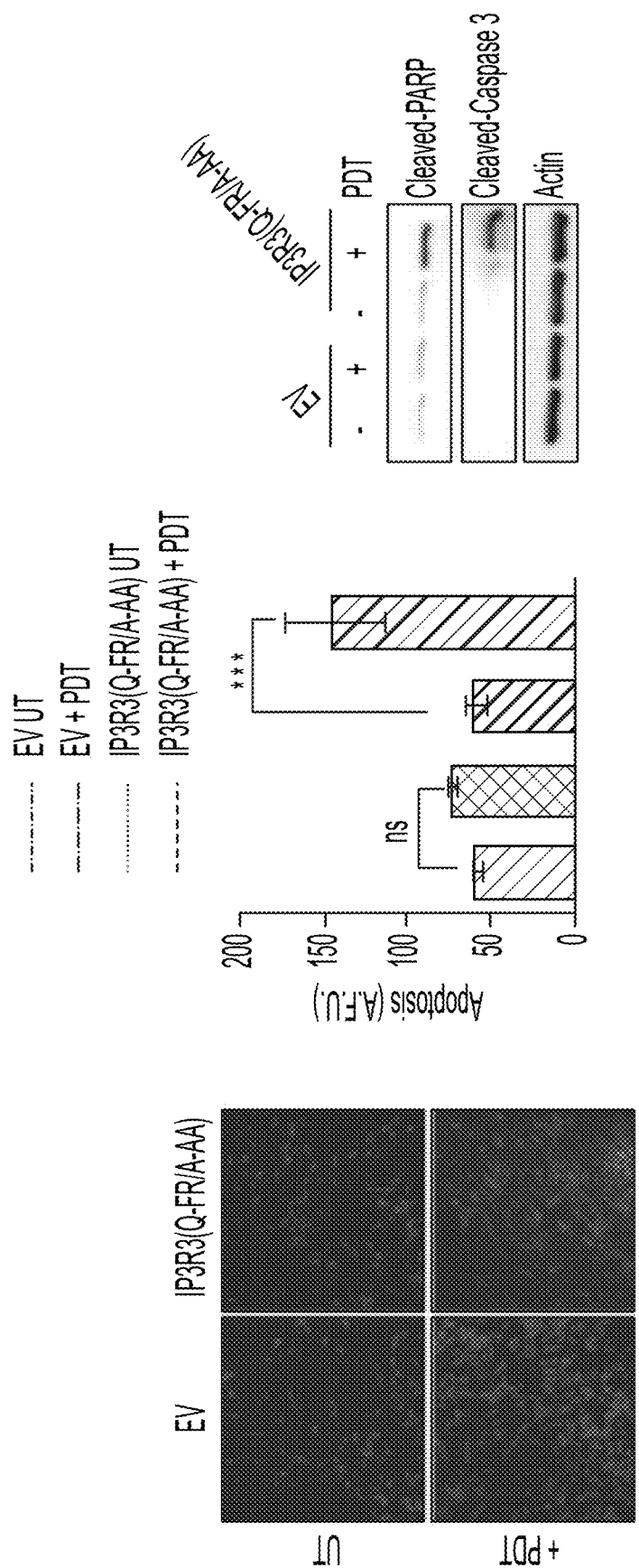
Figure 14C:
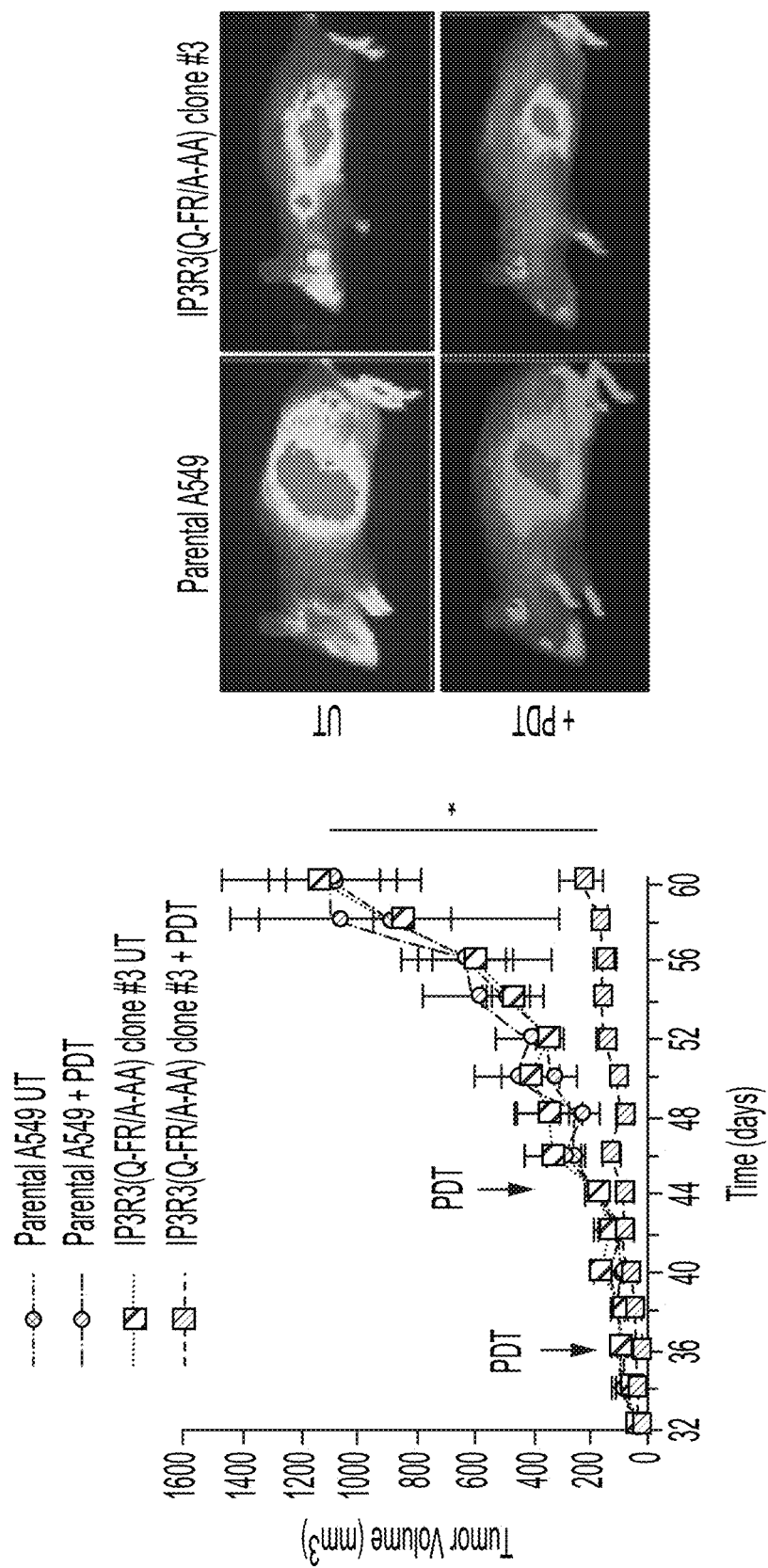
Figure 14C:
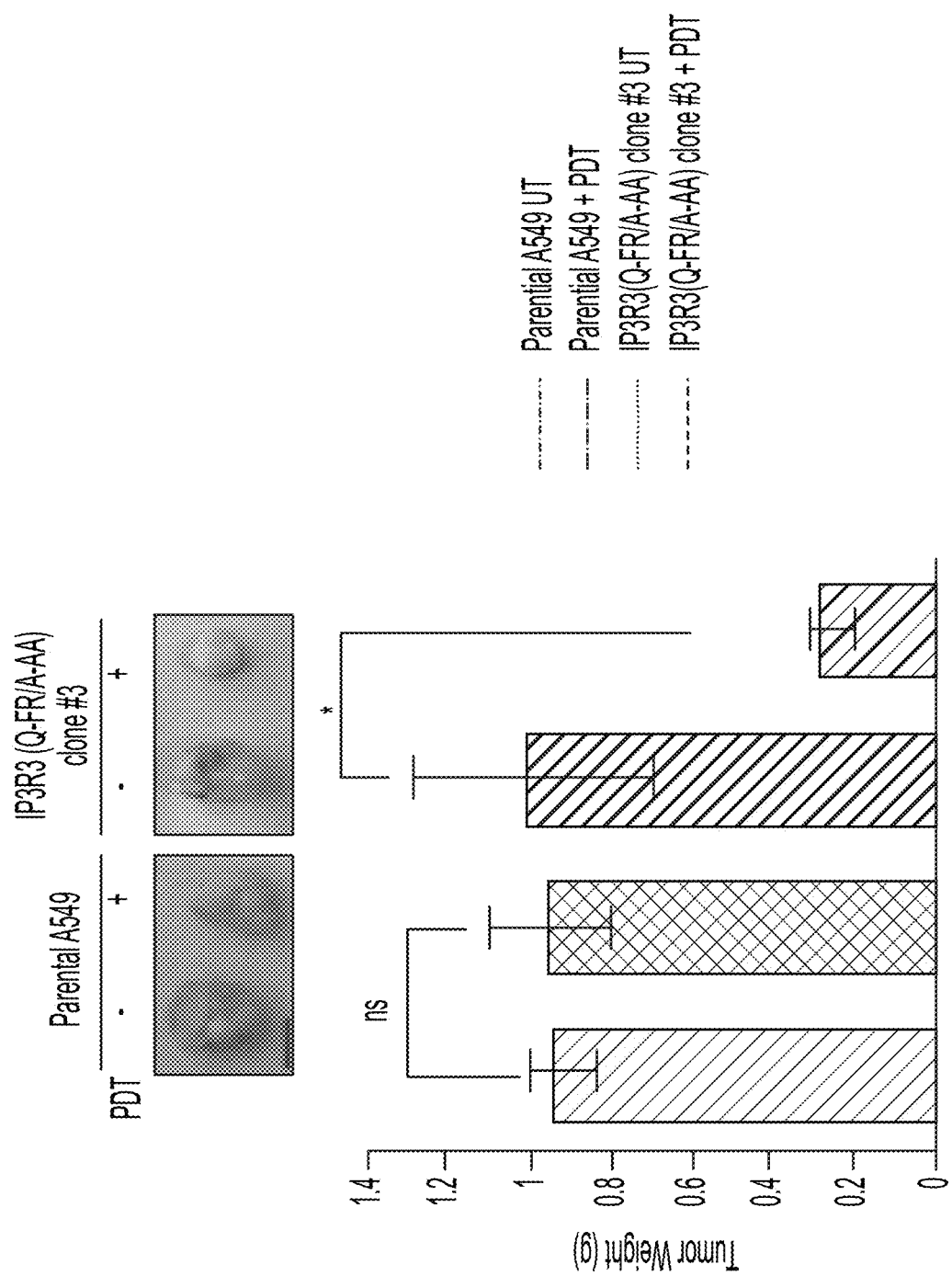
Figure 14D:
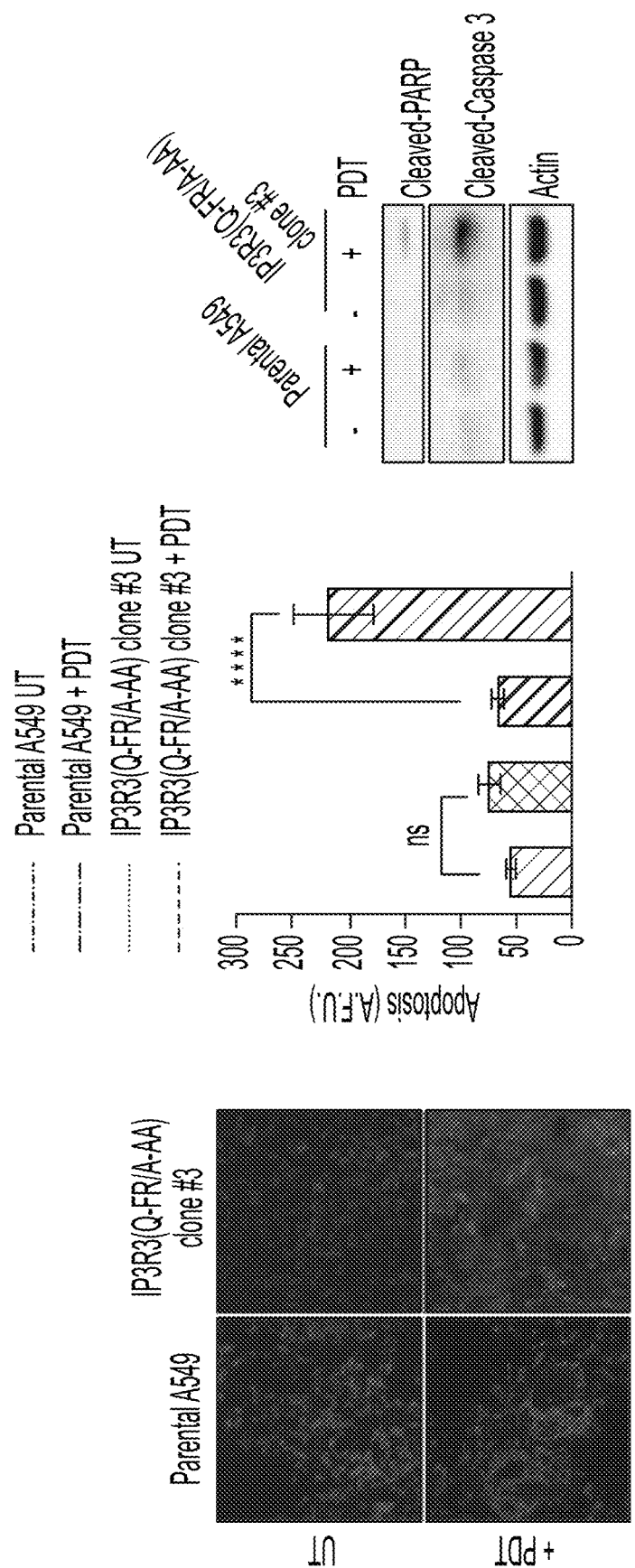
Figure 14E:
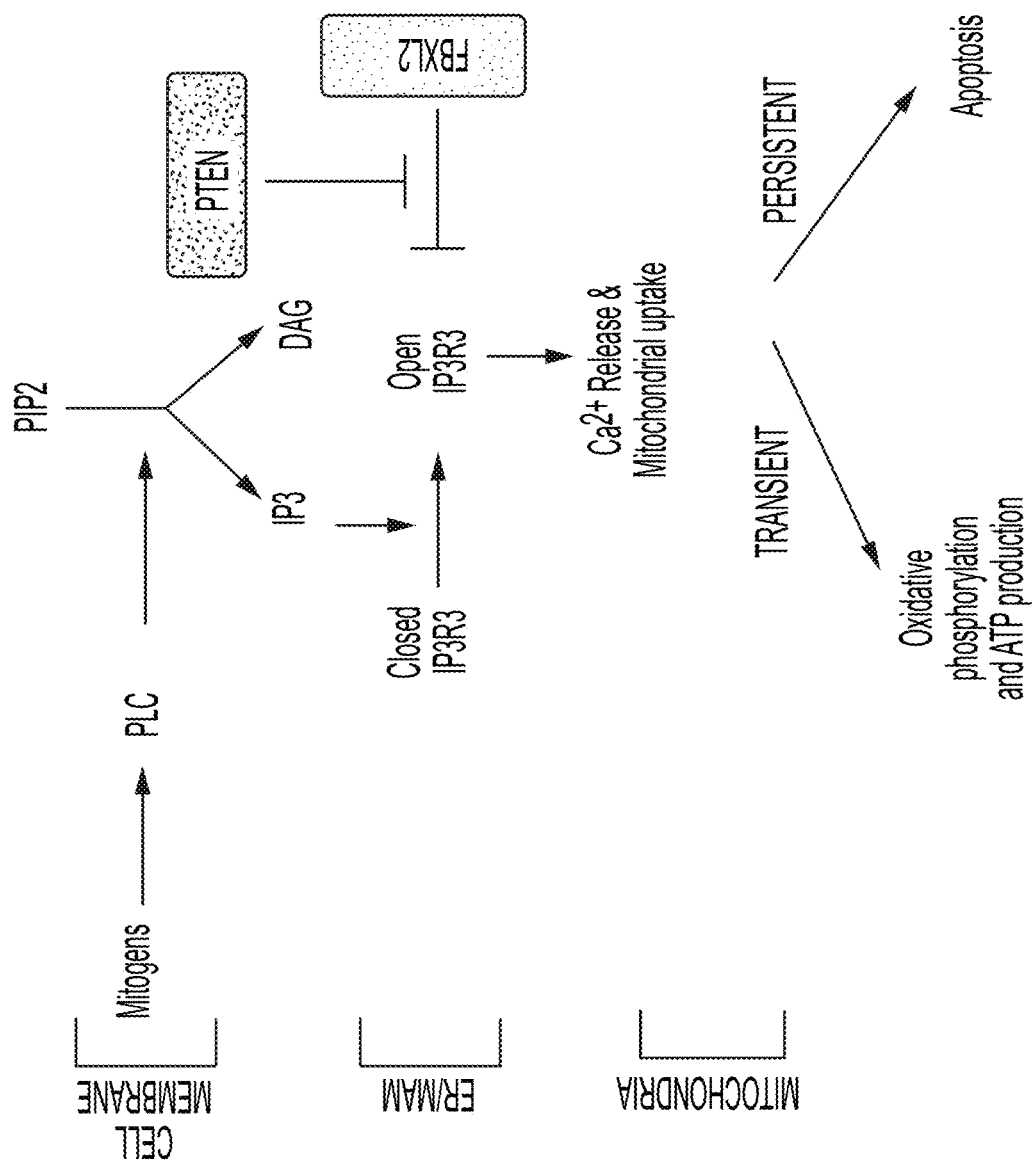

CRISPR genome editing. To generate ITPR3 Q550A; F553A;R554A, an optimal gRNA target sequence closest to the genomic target site and a 2 kb homologous recombination (HR) donor template were designed using the Benchling CRISPR Genome Engineering tool. The HR donor template was designed to introduce alanine substitutions at position Q550, F553 and R554, silent base-pair mutations to disrupt the PAM site, and an XhoI restriction site for bulk population screening, and was purchased as a synthetic gene from IDT. ITPR3 gRNA target sequence (see FIG. 11a) was cloned into pSpCas9(BB)-2A-GFP (PX458), a gift from F Zhang (Addgene plasmid no. 48138). Similarly, to generate FBXL2 deletions, two optimal gRNA target sequences (see FIG. 5f) closest to the genomic target sites in either exon 2 or exon 3 were designed using the Benchling CRISPR Genome Engineering tool and cloned into the pSpCas9(BB)2A-GFP (PX458) (ref. 25). RPE-1, A549 and PC3 cells were seeded into 10-cm dishes at approximately 70% confluency, and transfected with 5 μg of gRNAcontaining PX458 plasmid and HR donor template, using lipofectamine 3000 (Life Technologies). The transfection was performed according to the manufacturer's recommended protocol, using a 2:1 ratio of lipofectamine:DNA. Two days after transfection, GFP-positive cells were sorted using the Beckman Coulter MoFlo XDP cell sorter (100 μm nozzle), and 15,000 cells were plated on a 15 cm dish. For ITPR3 Q550A;F553A;R554A knock-in, a GFP-sorted population sample was also collected for subsequent bulk population genotyping by amplification of the target region and digestion with XhoI. 8-10 days later, single cell clones were picked, trypsinized in 0.25% Trypsin-EDTA for 5 min, and plated into individual wells of a 96-well plate for genotyping. Genomic DNA was collected using QuickExtract (Epicentre). Genotyping PCRs were performed with MangoTaq DNA Polymerase (Bioline), using primers surrounding the genomic target sites (see FIG. 5f and FIG. 11a). The resulting PCR products were then purified. For ITPR3 Q550A;F553A;R554A knock-in, PCR products were also digested with XhoI. Positive clones were sequenced to determine the presence of a indel event (FBXL2 knockout) or complete recombination event (ITPR3 Q550A;F553A;R554A knock-in). To further validate the mutational status of candidate clones, the PCR products were subjected to TOPO-TA Cloning (Invitrogen), and sequenced in order to distinguish the amplified products of distinct alleles. Fifty bacterial colonies for each TOPO-TA cloning reaction were sequenced and aligned to the corresponding wild-type template in Benchling to confirm that all alleles were correctly targeted.

Statistics analyses. All data were analysed by Prism 6 (GraphPad). Unless otherwise noted in figure legends, data are representative of at least three biologically independent experiments. Two-group datasets were analysed by Student's unpaired t-test. For three or more group analysis, one-way ANOVA Tukey's multiple comparison test was used. Linear regression analysis was performed with the GraphPad Prism 7.02 software $\chi2$ test. One asterisk was used for $P<0.05$, two asterisks for $P<0.01$, three asterisks for $P<0.001$, and four asterisks for $P<0.0001$. Statistical analyses from independent experiments are reported in the Source Data files and in Supplementary Table 1.

ADDITIONAL REFERENCES CITED IN METHODS

14. D'Angiolella, V. et al. Cyclin F-mediated degradation of ribonucleotide reductase M2 controls genome integrity and DNA repair. Cell 149, 1023-1034 (2012).

15. Duan, S. et al. mTOR generates an auto-amplifi loop by triggering the βTrCP-and CK1α-dependent degradation of DEPTOR. Mol. Cell 44, 317-324 (2011).

16. Duan, S. et al. FBXO11 targets BCL6 for degradation and is inactivated in diff large B-cell lymphomas. Nature 481, 90-93 (2012).

17. Dankert, J. F. et al. Cyclin F-mediated degradation of SLBP limits H2A.X accumulation and apoptosis upon genotoxic stress in G2. Mol. Cell 64, 507-519 (2016).

18. Yoshida, Y. et al. A comprehensive method for detecting ubiquitinated substrates using TR-TUBE. Proc. Natl Acad. Sci. USA 112, 4630-4635 (2015). 19. Grynkiewicz, G., Poenie, M. & Tsien, R. Y. A new generation of Ca2+ indicators with greatly improved fluorescence properties. J. Biol. Chem. 260, 3440-3450 (1985).

20. Marchi, S. et al. Akt kinase reducing endoplasmic reticulum Ca2+ release protects cells from Ca2+-dependent apoptotic stimuli. Biochem. Biophys. Res. Commun. 375, 501-505 (2008). 21. Joseph, S. K., Lin, C., Pierson, S., Thomas, A. P. & Maranto, A. R. Heteroligomers of type-I and type-III inositol trisphosphate receptors in WB rat liver epithelial cells. J. Biol. Chem. 270, 23310-23316 (1995).

22. Wieckowski, M. R., Giorgi, C., Lebiedzinska, M., Duszynski, J. & Pinton, P. Isolation of mitochondria-associated membranes and mitochondria from animal tissues and cells. Nat. Protocols 4, 1582-1590 (2009).

23. Barber, A. G. et al. Characterization of desmoglein expression in the normal prostatic gland. Desmoglein 2 is an independent prognostic factor for aggressive prostate cancer. PLoS One 9, e98786 (2014).

24. Castillo-Martin, M., Thin, T. H., Collazo Lorduy, A. & Cordon-Cardo, C. Immunopathologic assessment of PTEN expression. Methods Mol. Biol. 1388, 23-37 (2016).

25. Ran, F. A. et al. Genome engineering using the CRISPR-Cas9 system. Nat. Protocols 8, 2281-2308 (2013).

26. Bokkala, S. & Joseph, S. K. Angiotensin II-induced down-regulation of inositol trisphosphate receptors in WB rat liver epithelial cells. Evidence for involvement of the proteasome pathway. J. Biol. Chem. 272, 12454-12461 (1997).

27. Oberdorf, J., Webster, J. M., Zhu, C. C., Luo, S. G. & Wojcikiewicz, R. J. Down-regulation of types I, II and III inositol 1,4,5-trisphosphate receptors is mediated by the ubiquitin/proteasome pathway. Biochem. J. 339, 453-461 (1999).

28. Alzayady, K. J., Panning, M. M., Kelley, G. G. & Wojcikiewicz, R. J. Involvement of the p97-Ufd1-Np14 complex in the regulated endoplasmic reticulum-associated degradation of inositol 1,4,5-trisphosphate receptors. J. Biol. Chem. 280, 34530-34537 (2005).

29. Mikoshiba, K. IP3 receptor/Ca2+ channel: from discovery to new signaling concepts. J. Neurochem. 102, 1426-1446 (2007).

30. Lin, C. C., Baek, K. & Lu, Z. Apo and InsP3-bound crystal structures of the ligand-binding domain of an InsP3 receptor. Nat. Struct. Mol. Biol. 18, 1172-1174 (2011).

31. Seo, M. D. et al. Structural and functional conservation of key domains in InsP3 and ryanodine receptors. Nature 483, 108-112 (2012).

32. Fan, G. et al. Gating machinery of InsP3R channels revealed by electron cryomicroscopy. Nature 527, 336-341 (2015). 33. Giorgi, C. et al. PML regulates apoptosis at endoplasmic reticulum by modulating calcium release. Science 330, 1247-1251 (2010).

34. Marchi, S. et al. Selective modulation of subtype III IP3R by Akt regulates ER Ca2+ release and apoptosis. Cell Death Dis. 3, e304 (2012).

35. Giorgi, C., Bonora, M. & Pinton, P. Inside the tumor: p53 modulates calcium homeostasis. Cell Cycle 14, 933-934 (2015).

36. Oakes, S. A. et al. Proapoptotic BAX and BAK regulate the type 1 inositol trisphosphate receptor and calcium leak from the endoplasmic reticulum. Proc. Natl Acad. Sci. USA 102, 105-110 (2005).

37. Sung, P. J. et al. Phosphorylated K-Ras limits cell survival by blocking Bcl-xL sensitization of inositol trisphosphate receptors. Proc. Natl Acad. Sci. USA 110, 20593-20598 (2013).

38. Chen, R. et al. Bcl-2 functionally interacts with inositol 1,4,5-trisphosphate receptors to regulate calcium release from the ER in response to inositol 1,4,5-trisphosphate. J. Cell Biol. 166, 193-203 (2004). 39. Khan, M. T., Wagner, L., II, Yule, D. I., Bhanumathy, C. & Joseph, S. K. Akt kinase phosphorylation of inositol 1,4,5-trisphosphate receptors. J. Biol. Chem. 281, 3731-3737 (2006).

40. Bononi, A. et al. Identifi of PTEN at the ER and MAMs and its regulation of Ca(2+) signaling and apoptosis in a protein phosphatase-dependent manner Cell Death Diff. 20, 1631-1643 (2013).

41. Tan, M. K., Lim, H. J., Bennett, E. J., Shi, Y. & Harper, J. W. Parallel SCF adaptor capture proteomics reveals a role for SCFFBXL17 in NRF2 activation via BACH1 repressor turnover. Mol. Cell 52, 9-24 (2013).

42. Alzayady, K. J. et al. Functional inositol 1,4,5-trisphosphate receptors assembled from concatenated homo- and heteromeric subunits. J. Biol. Chem. 288, 29772-29784 (2013).

43. Wojcikiewicz, R. J. & He, Y. Type I, II and III inositol 1,4,5-trisphosphate receptor co-immunoprecipitation as evidence for the existence of heterotetrameric receptor complexes. Biochem. Biophys. Res. Commun. 213, 334-341 (1995).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A method of treating a cancer in a subject, the method comprising administering to the subject a therapeutically affective amount of a geranylgeranyltransferase I (GGTase I) inhibitor; wherein the cancer comprises a defective PTEN, a hyperactivated FBXL2, or a low level of IP3R3; wherein the cancer is selected from the group consisting of melanoma, prostate cancer, glioblastoma, lung cancer, and breast cancer.

2. The method of claim 1, wherein the GGTase inhibitor comprises the compound GGTI-2418, or a pharmaceutically acceptable salt or hydrate thereof.

3. The method of claim 1, wherein the cancer comprises a defective PTEN.

4. The method of claim 3, wherein the defective PTEN is a mutant PTEN.

5. The method of claim 3, wherein the defective PTEN is due to low levels of PTEN gene expression.

6. The method of claim 5, wherein the level of PTEN gene expression is zero.

7. The method of claim 1, wherein the cancer comprises a hyperactivated FBXL2.

8. The method of claim 1, wherein the cancer comprises a low level of IP3R3.

9. The method of claim 1, further comprising administering to the subject photodynamic therapy.

10. The method of claim 1, further comprising administering to the subject a pharmaceutically effective amount of an Akt inhibitor.

11. The method of claim 10, wherein the Akt inhibitor is TCN or TCN-P.

12. The method of claim 1, wherein the method further comprises detecting whether the cancer comprises a defective PTEN, hyperactivated FBXL2, or low level of IP3R3.

13. An assay for determining when to treat cancer with a geranylgeranyltransferase I (GGTase I) inhibitor comprising a microarray, SAGE, Northern blot, western blot, real-time PCR, enzyme-linked immunosorbent assay, immunoelectrophoresis, high-performance liquid chromatography, or liquid chromatography-mass spectrometry and primers, probes, or antibodies specific for the detection of PTEN, FBXL2 or IP3R3; wherein the cancer is selected from the group consisting of melanoma, prostate cancer, glioblastoma, lung cancer, and breast cancer.

* * * * *